(12) United States Patent
Chudzik et al.

(10) Patent No.: US 8,512,736 B2
(45) Date of Patent: *Aug. 20, 2013

(54) COATINGS INCLUDING NATURAL BIODEGRADABLE POLYSACCHARIDES AND USES THEREOF

(75) Inventors: Stephen J. Chudzik, St. Paul, MN (US); Joseph A. Chinn, Shakopee, MN (US); Dale G. Swan, St. Louis Park, MN (US); Michael J. Burkstrand, Richfield, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1303 days.

This patent is subject to a terminal disclaimer.

(21) Appl. No.: 11/271,213

(22) Filed: Nov. 11, 2005

(65) Prior Publication Data

US 2007/0065481 A1  Mar. 22, 2007

Related U.S. Application Data

(60) Provisional application No. 60/719,466, filed on Sep. 21, 2005.

(51) Int. Cl.
*A61K 47/36* (2006.01)
*A61K 47/40* (2006.01)
*A61F 9/007* (2006.01)

(52) U.S. Cl.
USPC ............................. 424/426; 424/428

(58) Field of Classification Search
USPC .................................... 424/426, 428
See application file for complete search history.

(56) References Cited

U.S. PATENT DOCUMENTS

| | | | |
|---|---|---|---|
| 4,079,025 A | 3/1978 | Young et al. | |
| 5,160,745 A | 11/1992 | De Luca et al. | |
| 5,668,193 A | 9/1997 | Gouda et al. | |
| 5,773,021 A * | 6/1998 | Gurtler et al. | 424/427 |
| 5,837,747 A | 11/1998 | Soon-Shiong et al. | |
| 6,007,833 A | 12/1999 | Chudzik et al. | |
| 6,083,524 A * | 7/2000 | Sawhney et al. | 424/426 |
| 6,140,313 A * | 10/2000 | Perbellini et al. | 514/54 |
| 6,156,345 A * | 12/2000 | Chudzik et al. | 424/484 |
| 6,197,757 B1 | 3/2001 | Perrier et al. | |
| 6,303,148 B1 | 10/2001 | Hennink | |
| 6,388,047 B1 | 5/2002 | Won et al. | |
| 6,514,286 B1 * | 2/2003 | Leatherbury et al. | 623/11.11 |
| 6,586,493 B1 | 7/2003 | Massia et al. | |
| 6,716,445 B2 | 4/2004 | Won et al. | |
| 2002/0086990 A1 * | 7/2002 | Kumar et al. | 536/63 |
| 2003/0077242 A1 | 4/2003 | Sawhney | |
| 2003/0105509 A1 | 6/2003 | Jang et al. | |
| 2003/0143274 A1 * | 7/2003 | Viegas et al. | 424/486 |
| 2003/0218130 A1 | 11/2003 | Boschetti et al. | |
| 2004/0037886 A1 * | 2/2004 | Hsu | 424/486 |
| 2004/0062778 A1 | 4/2004 | Shefer et al. | |
| 2004/0122165 A1 | 6/2004 | Won et al. | |
| 2004/0202719 A1 | 10/2004 | Zion et al. | |
| 2005/0136091 A1 | 6/2005 | Chudzik et al. | |
| 2005/0147758 A1 * | 7/2005 | Mao et al. | 427/372.2 |
| 2005/0255142 A1 | 11/2005 | Chudzik et al. | |
| 2007/0065482 A1 | 3/2007 | Chudzik et al. | |
| 2007/0065483 A1 | 3/2007 | Chudzik et al. | |
| 2007/0065484 A1 | 3/2007 | Chudzik et al. | |

FOREIGN PATENT DOCUMENTS

| | | |
|---|---|---|
| WO | WO9309176 A2 | 5/1993 |
| WO | WO9704011 A1 | 2/1997 |
| WO | WO2005034875 | 4/2005 |

OTHER PUBLICATIONS

International Search Report dated Sep. 26, 2006, for corresponding International Patent Application No. PCT/US2005/040927 (5 pgs).
R. Jantas, "Synthesis and characterization of acryloyloxystarch," Journal of Applied Polymer Science, vol. 65, Issue 11, 1997, pp. 2123-2129.

* cited by examiner

*Primary Examiner* — Shaojia Anna Jiang
*Assistant Examiner* — Jonathan S Lau
(74) *Attorney, Agent, or Firm* — Kagan Binder, PLLC

(57) ABSTRACT

Biodegradable coatings and articles that include natural biodegradable polysaccharides are described. The coatings and articles are formed from a plurality of natural biodegradable polysaccharides having pendent coupling groups.

20 Claims, 4 Drawing Sheets

US 8,512,736 B2

COATINGS INCLUDING NATURAL BIODEGRADABLE POLYSACCHARIDES AND USES THEREOF

CROSS-REFERENCE TO RELATED APPLICATIONS

The present non-provisional Application claims the benefit of commonly owned provisional Application having Ser. No. 60/719,466, filed on Sep. 21, 2005, and entitled ARTICLES AND COATINGS INCLUDING NATURAL BIODEGRADABLE POLYSACCHARIDES AND USES THEREOF.

TECHNICAL FIELD

The present invention relates to biodegradable coating compositions and methods for coating the surface of medical devices with a natural biodegradable polymeric material. Bioactive agents can be included in the biodegradable coatings to provide a therapeutic effect to a patient.

BACKGROUND

Recently, the use of drug-eluting stents (DES) in percutaneous coronary interventions has received much attention. DES are medical devices that present or release bioactive agent into their surroundings (for example, luminal walls of coronary arteries). Generally speaking, a bioactive agent can be coupled to the surface of a medical device by surface modification, embedded, and released from within polymeric materials (matrix-type), or surrounded by and released through a carrier (reservoir-type). The polymeric materials in such applications should optimally act as a biologically inert barrier and not induce further inflammation within the body. However, the molecular weight, porosity of the polymer, a greater percentage of coating exposed on the medical device, and the thickness of the polymer coating can contribute to adverse reactions to the medical device.

Another way to deliver bioactive agents from the surface of a medical device is by using a coating that has a biodegradable polymer, such as polylactic acid. As the coating degrades, the bioactive agent is released from the surface of the device. Although biodegradable coatings that include polylactic acid have been described in a number of documents, for example, U.S. Pat. No. 6,258,121, there remains a need for improved coatings and coating materials.

Some concerns exist that regard the use of biodegradable materials that degrade into materials that are not typically found in the body, or that are found at particularly low levels in the body. These types of biodegradable materials have the potential to degrade into products that cause unwanted side effects in the body by virtue of their presence or concentration in vivo. These unwanted side effects can include immune reactions, toxic buildup of the degradation products in the liver, or the initiation or provocation of other adverse effects on cells or tissue in the body.

Another problem is that preparations of some biodegradable materials may not be obtained at consistent purity due to variations inherent in natural materials. This is relevant at least with regard to biodegradable materials derived from animal sources. Inconsistencies in preparations of biodegradable materials can result in problematic coatings.

It is also desirable to provide biodegradable drug delivery coatings that are easy to prepare, cost effective, and that also offer a wide range of flexibility with regard to the type and amount of drug or drugs to be delivered from the biodegradable coating.

Other aspects of the present invention relate to the use of polymeric coatings for providing a sealant function to medical articles. Biodegradable sealant compositions have been used on articles having porous surfaces, such as fabrics associated with implantable medical articles. The sealant coating initially renders the porous surface impermeable to fluids for a period of time. However, as the sealant materials degrade and are resorbed by the body, cells involved in tissue repair infiltrate the porous material and replace the sealant materials. Thus, newly formed tissue replaces the original function of the coated sealant over a period of time.

Animal-derived sealant materials such as collagen and gelatin are commonly used to coat textile grafts. These materials can be resorbed in vivo. The blood clotting protein fibrin has also been utilized as a sealant material. Despite their uses, there are drawbacks and concerns with using these types of sealant materials. One particular problem is that it is difficult to produce consistent sealant compositions from these animal sources due to batch-to-batch variations inherent in their production.

In many cases the collagen used in sealant technologies is obtained from non-human animal sources, such as bovine sources. In these cases there is the possibility that bovine collagen preparations may contain unwanted contaminants that are undesirable for introduction into a human subject. One example of an unwanted contaminant is the prionic particles that cause Bovine Spongiform Encephalopathy (BSE).

BSE, also termed Mad Cow Disease, is one of a group of progressive neurological diseases called transmissible spongiform encephalopathies, or TSEs (named for deteriorated areas of the brain that look like sponges). Various forms of TSE have been reported, including scrapie in sheep and chronic wasting disease in elk and mule deer. It is generally believed that the use of recycled animal parts led to the cross-species contamination of scrapie in sheep to mad cow disease, and the ingestion of contaminated beef and bovine products led to the human variant of this disease, Creutzfeldt-Jakob Disease (CJD).

Additional concerns are that preparations from animal sources may provide other unwanted contaminants, such as antigenic factors. These antigenic factors may promote a localized immune response in the vicinity of the implanted article and foul its function. These factors may also cause infection as well as local inflammation.

While synthetic materials can be used in the preparation of sealant compositions, these synthetic materials have the potential of degrading into non-naturally occurring products. These non-naturally occurring products have the potential to be at least partially toxic to the organism or immunogenic and cause inflammation, as well as infection, at or around the site of implantation.

SUMMARY OF THE INVENTION

In one aspect, the present invention provides compositions and methods for preparing biodegradable coatings that are particularly useful for coating surfaces of implantable medical devices, such as stents and catheters, and are capable of releasing bioactive agents from the device surface. These coating compositions include a natural biodegradable polysaccharide as a component that can be crosslinked to form a matrix from which a therapeutic material such as a drug, a biomolecule, or cells (referred to herein as a "bioactive agents") can be released or retained. In some embodiments of the invention, a bioactive agent is present in and can be released from the biodegradable matrix; in other embodiments a bioactive agent is present in a biodegradable microparticle, the microparticle being immobilized within the matrix.

In other aspects of the invention, the natural biodegradable polysaccharide is used to prepare an article, such as an article that can be implanted or formed within the body (for example, by in situ formation). In some aspects, the article can be amorphous, such as a polymerized mass of natural biodegradable polysaccharides that is formed within or on a portion of the body, by using an in vivo matrix-forming composition.

In other aspects, the invention provides an article fabricated from natural biodegradable polysaccharide, wherein the article has a defined structure, and wherein the article can be implanted in the body (such as a filament). Such articles are referred to herein as "medical implants". A medical implants having a defined structure can be formed by any suitable process, including molding, extruding, shaping, cutting, casting, and the like.

The article can be used for one or more purposes, such as for releasing or retaining a bioactive agent at a location in the body. For example, the article can be a bioactive agent-containing medical implant or depot. The article can also provide one or more mechanical or physical properties to a portion the body. For example, the natural biodegradable polysaccharides can be included in a composition used for the formation of a biodegradable medical device such as a stent.

In some aspects, the article, such as an in vivo formed matrix, is used in methods for the treatment of any one or more of a variety of medical conditions or indications, including restoring, improving, and/or augmenting tissue growth or function, in particular those for orthopedic, dental, and bone graft applications. These functions can be provided by placing a polymerized matrix of biodegradable polysaccharides in contact with a host tissue. The matrix can restore or improve tissue growth or function by, for example, promoting or permitting formation of new tissue between and into the matrix. The effect on tissue can be caused by the biodegradable polysaccharide itself, or the biodegradable polysaccharide in combination with one or more bioactive agent(s) that can be present in and/or released from the matrix. Exemplary bioactive agents that can affect tissue function include peptides, such as peptides that are involved in tissue repair processes and belonging to the EGF, FGF, PDGF, TGF-$\beta$, VEGF, PD-ECGF or IGF families, and also peptides derived from bone morphogenetic protein 2, or BMP-2. The bioactive agent can also be a cell, such as a platelet.

In some aspects, the coating or article can include a radiopacifying agent.

In preparing the coatings or articles, a plurality of natural biodegradable polysaccharides are crosslinked to each other via coupling groups that are pendent from the natural biodegradable polysaccharide (i.e., one or more coupling groups are chemically bonded to the polysaccharide). In some aspects, the coupling group on the natural biodegradable polysaccharide is a polymerizable group. In a free radical polymerization reaction the polymerizable group can crosslink natural biodegradable polysaccharides together in the composition, thereby forming a natural biodegradable polysaccharide matrix, which can be a portion of a coating, an in-vivo formed matrix, or the body member of a medical implant.

The natural biodegradable polysaccharides described herein are non-synthetic polysaccharides that can be associated with each other to form a matrix, which can be used as a coating or as an article, for example, a medical implant or an in-vivo formed matrix. The natural biodegradable polysaccharides can also be enzymatically degraded, but offer the advantage of being generally non-enzymatically hydrolytically stable. This is particularly advantageous for bioactive agent delivery, as in some aspects the invention provides coatings or articles capable of releasing the bioactive agent under conditions of enzyme-mediated degradation, but not by diffusion. Therefore, the kinetics of bioactive agent release from the coatings or articles of the invention are fundamentally different than those of coatings prepared from synthetic biodegradable materials, such as poly(lactides).

Natural biodegradable polysaccharides include polysaccharide and/or polysaccharide derivatives that are obtained from natural sources, such as plants or animals. Exemplary natural biodegradable polysaccharides include amylose, maltodextrin, amylopectin, starch, dextran, hyaluronic acid, heparin, chondroitin sulfate, dermatan sulfate, heparan sulfate, keratan sulfate, dextran sulfate, pentosan polysulfate, and chitosan. Preferred polysaccharides are low molecular weight polymers that have little or no branching, such as those that are derived from and/or found in starch preparations, for example, amylose and maltodextrin.

Because of the particular utility of the amylose and maltodextrin polymers, in some aspects natural biodegradable polysaccharides are used that have an average molecular weight of 500,000 Da or less, 250,000 Da or less, 100,000 Da or less, or 50,000 Da or less. In some aspects the natural biodegradable polysaccharides have an average molecular weight of 500 Da or greater. In some aspects the natural biodegradable polysaccharides have an average molecular weight in the range of about 1000 Da to about 10,000 Da. Natural biodegradable polysaccharides of particular molecular weights can be obtained commercially or can be prepared, for example, by acid hydrolysis and/or enzymatic degradation of a natural biodegradable polysaccharide preparation, such as starch. The decision of using natural biodegradable polysaccharides of a particular size range may depend on factors such as the physical characteristics of the coating composition (e.g., viscosity), the desired rate of degradation of the coating, the presence of other optional moieties in the coating composition (for example, bioactive agents, etc.), etc.

The natural biodegradable polysaccharides that are used in accordance with the methods and compositions of the invention are readily available at a low cost and/or can be prepared easily using established techniques. This allows for a cost effective method of coating and fabricating medical articles.

The use of natural biodegradable polysaccharides, such as maltodextrin or amylose, provides many advantages when used in a coating composition applied to the surface of a medical device, or for the formation of an article, such as one that can be used in vivo. Degradation of a natural biodegradable polysaccharide-containing article, or coating from the surface of a medical device, can result in the release of, for example, naturally occurring mono- or disaccharides, such as glucose, which are common serum components. Furthermore, the use of natural biodegradable polysaccharides that degrade into common serum components, such as glucose, can be viewed as more acceptable than the use of synthetic biodegradable polysaccharides that degrade into non-natural compounds, or compounds that are found at very low concentrations in the body.

In some aspects of the invention, this advantageous feature is reflected in the use of natural biodegradable polysaccharides which are non-animal derived, such as amylose and maltodextrin, and that degrade into products that present little or no immunogenic or toxic risk to the individual. The invention provides improved, cost-efficient, natural biodegradable polysaccharide compositions for articles or coatings that can be used in a variety of medical treatments.

Another advantage of the invention is that the natural biodegradable polysaccharide-based coatings are more resistant to hydrolytic degradation than other biodegradable polymers, such as poly(lactides). Degradation of the natural biodegradable polysaccharides of the invention are primarily enzyme-mediated, with minimal or no hydrolysis of the natural biodegradable polysaccharide occurring when a natural biodegradable polysaccharide-containing coating is prepared under ambient conditions. This allows the natural biodegradable polysaccharide-based coatings to remain substantially stable (for example, resistant to degradation) prior to placing the coated-article in vivo. For example, a natural biodegradable polysaccharide coated article can be manipulated in a non-biological, aqueous-based-medium without risk that the coating will prematurely degrade due to non-enzyme-mediatated hydrolysis. Other coatings that are based on biodegradable polymers such as poly(lactide) or poly(lactide-co-glycolide) are subject to hydrolysis even at relatively neutral pH ranges (e.g., pH 6.5 to 7.5) and therefore do not offer this advantage.

Therefore, the invention includes natural biodegradable polysaccharide-containing compositions, coatings, articles, and methods of preparing such that have the advantage of providing stability in the presence of an aqueous environment.

In one aspect, the invention provides a shelf-stable composition for preparing a biodegradable coating, the shelf stable composition comprising a natural biodegradable polysaccharide comprising coupling groups. These compositions could be obtained or prepared, according to the details provided herein, and then stored for a period of time before the composition is used to form a biodegradable coating or article, without significant degradation of the natural biodegradable polysaccharide occurring during storage. Accordingly, the invention also provides methods for preparing a biodegradable coating comprising preparing a biodegradable coating composition comprising a natural biodegradable polysaccharide comprising coupling group; storing the coating composition for an amount of time; and then using the coating composition to prepare a biodegradable coating or a biodegradable article. In some aspects, the biodegradable article is formed in situ, for example, by promoting the polymerization of the natural biodegradable polysaccharide within the body. Optionally, one or more bioactive agents and/or microparticles can be added before or after storage of the coating composition.

In a related aspect, the invention also provides the advantage of being able to perform methods wherein the natural biodegradable polysaccharide is subject to exposure to an aqueous solution without risking significant degradation of the natural biodegradable polysaccharide. For example, the natural biodegradable polysaccharide may be contacted with an aqueous solution in a synthetic or post-synthetic step, including addition synthesis reactions and purification steps, or a coating that includes the natural biodegradable polysaccharide can be contacted with an aqueous solution in, for example, a sterilization step or a step that involves incorporation of a bioactive agent into the biodegradable coating.

In yet another aspect, the invention relates to the stability of an article or a coating that is formed on an article. The invention provides a method comprising obtaining an article formed from, or having a coating comprising, a natural biodegradable polysaccharide, and then contacting the article with an aqueous solution for a period of time wherein the article or coating remains predominantly stable in the solution. The aqueous solution can be, for example, a storage solution, a solution that is used to hydrate the surface of the coated device, or an aqueous sterilization solution.

Degradation of the natural biodegradable polysaccharide-containing coating or article may commence when placed in contact with a body fluid, which may include natural biodegradable polysaccharide-degrading enzymes, such as carbohydrases.

The invention also provides a useful way to deliver larger hydrophilic bioactive agents, such as polypeptides, nucleic acids, and polysaccharides, as well as viral particles and cells from the biodegradable article, or biodegradable coating on a surface, such as a medical device or a coating on a surface thereof. Comparatively, the use of non-degrading drug delivery matrices may not be useful for the delivery of these larger bioactive agents if they are too large to diffuse out of the matrix. However, according to some aspects of the invention, an article or a coating that includes a matrix of the natural biodegradable polysaccharide having a bioactive agent can be placed or formed in the body, and as the matrix degrades the bioactive agent is gradually released from the matrix. In one aspect of the invention, the bioactive agent has a molecular weight of about 10,000 Da or greater.

In some aspects, the invention provides a drug-releasing biodegradable article, coating, or composition comprising (i) a natural biodegradable polysaccharide, preferably selected from amylose and maltodextrin, comprising an ethylenically unsaturated group, (ii) an initiator, and (iii) a bioactive agent selected from the group of polypeptides, polynucleotides, and polysaccharides.

In another aspect, a coated surface is prepared on a medical device, such as a stent or catheter. The methods include disposing in one or more steps the following reagents on a surface: (a) an initiator, (b) a natural biodegradable polysaccharide, preferably selected from amylose and maltodextrin, comprising an ethylenically unsaturated group, and (c) a bioactive agent. After the components have been disposed on the surface, the initiator is activated to crosslink a plurality of natural biodegradable polysaccharides comprising ethylenically unsaturated groups that are present in the composition, thereby forming a coating on the surface that includes the bioactive agent.

Depending on the application, the initiator can be first disposed on the surface, followed by disposing the natural biodegradable polysaccharide and bioactive agent on the layer of initiator. Alternatively, the initiator, natural biodegradable polysaccharide, and bioactive agent are mixed and disposed together on the surface.

Therefore, in some aspects, the invention provides a method for delivery of a bioactive agent, or more than one bioactive agent, to a subject. The method comprises the steps of providing a coated article to a subject, the coated article having a biodegradable coating which comprises a plurality of natural biodegradable polysaccharides associated via coupling groups, and bioactive agent. The coated article is then exposed to a carbohydrase to promote the degradation of the coating and release of the bioactive agent. For example, a biodegradable coating or article including amylose and/or maltodextrin polymers can be exposed to an α-amylase to promote degradation of the coating and release of the bioactive agent. The step of exposing can be performed by placing the biodegradable coating or article in a patient. In the absence of the carbohydrase there is substantially no release of the bioactive agent. In some aspects the bioactive agent comprises a polypeptide, such as an antibody or an antibody fragment.

In some aspects, the methods of the invention can be used to prepare coatings wherein an amount of bioactive agent in the range of 1% to 17% of the total amount of bioactive agent present in the coating is released from the coating within a period of 2 days, and coatings wherein an amount of bioactive agent in the range of 1% to 20% of the total amount of bioactive agent present in the coating is released from the coating within a period of 8 days.

In other aspects, the bioactive agent is delivered from a medical implant having a biodegradable body member which comprises a plurality of natural biodegradable polysaccharide associated via pendent coupling groups, the body member also including a bioactive agent. The medical implant is then exposed to a carbohydrase to promote the degradation of the implant and release of the bioactive agent.

In some aspects, the methods of the invention can be used to prepare medical implants wherein an amount of bioactive agent in the range of 1% to 17% of the total amount of bioactive agent present in the medical implant is released within a period of 8 days, medical implants wherein an amount of bioactive agent in the range of 1% to 41% of the total amount of bioactive agent present in the medical implant is released within a period of 14 days, and medical implants wherein an amount of bioactive agent in the range of 1% to 60% of the total amount of bioactive agent present in the medical implant is released within a period of 21 days.

Alternatively a carbohydrase can be administered to a subject, or the carbohydrase can be provided to a portion of the article, wherein the carbohydrase is released from the portion and locally causes the degradation of the coating.

The coatings can also have favorable bioactive agent-releasing properties when the coated article has been placed in the body. In this regard, the present invention provides an overall improvement in terms of providing coatings for implantable medical articles. Articles that are fabricated from the biodegradable polysaccharides can have many of the same beneficial surface characteristics as provided by the biodegradable polysaccharide coatings.

In another aspect of the invention, the natural biodegradable polysaccharide is modified with a hydrophobic moiety in order to provide a biodegradable matrix having hydrophobic properties. Therefore, a biodegradable coating or article can be formed from natural biodegradable polysaccharide comprising one or more pendent coupling groups and one or more pendent hydrophobic moieties. Exemplary hydrophobic moieties include fatty acids and derivatives thereof, and $C_2$-$C_{18}$ alkyl chains.

Therefore, in some aspects of the invention, modification of the natural biodegradable polysaccharide allows for preparation of coatings or articles that are biodegradable and that can release a hydrophobic bioactive agent.

In other aspects, the hydrophobic moiety pendent from the natural biodegradable has properties of a bioactive agent. Upon degradation of the matrix, the hydrophobic moiety can be hydrolyzed from the natural biodegradable polymer and released to provide a therapeutic effect. One example of a therapeutically useful hydrophobic moiety is butyric acid.

In yet another aspect, the invention provides methods and articles for improving the stability of a bioactive agent that is delivered from a coating or an article by utilizing a natural biodegradable non-reducing polysaccharide. The non-reducing polysaccharide can provide an inert matrix and thereby improve the stability of sensitive bioactive agents, such as proteins and enzymes. The article or coating can include a matrix having a plurality of natural biodegradable non-reducing polysaccharides along with a bioactive agent, such as a polypeptide. An exemplary non-reducing polysaccharide comprises polyalditol. Biodegradable non-reducing polysaccharides can very useful for formulating coatings or articles that release the bioactive agent over a prolonged period of time.

While it is desirable to make coatings or articles that provide desired properties (for example, bioactive agent release, wettability, etc.), their actual preparation can be challenging. In particular, the use of some polysaccharides for preparing coatings or articles may result in products that are unsuitable for use. For example, some polysaccharide-based coatings, including those made from starch-based materials, have the potential to be overly brittle and inflexible. While these properties may be suitable for pharmaceutical capsules or tablets they are generally undesirable as properties for coatings or articles, such as bioactive agent releasing or sealant coatings, or medical implants.

Despite this, the present invention demonstrates the preparation of articles and coatings that include natural biodegradable polysaccharides that are suitable for in vivo use. These products display excellent physical characteristics and are suitable for use in applications wherein a particular function, such as bioactive agent delivery or a sealant function is desired. For example, coatings or articles can be prepared having viscoelastic properties. In one aspect of the invention, the coating or article has an elastic modulus value in the range of 27 kPa to 30 kPa.

The coatings of the present invention can have desirable surface properties that include elasticity and wettability, in addition to being biodegradable. Also, it has surprisingly been discovered that the coatings demonstrate excellent lubricity, which can provide distinct advantages for short term and single use devices. Therefore, in one aspect, the invention presents a method for providing lubricity to an article surface comprising the steps of disposing a composition comprising a plurality of natural biodegradable polysaccharides comprising pendent coupling groups and activating the coupling groups to promote association of the plurality of natural biodegradable polysaccharides and formation of a lubricious coating on the article surface.

The coatings can be formed on the surfaces of medical articles, including those designed for single use or for short-term use. For example, a lubricious coating can be formed on a catheter.

Coatings including natural biodegradable polysaccharides can be prepared to provide a lubricity of 20 g or less, and can also be prepared to provide a lubricity of 15 g or less, or 10 g or less, as based on friction testing. The coatings were also shown to be highly durable, as lubricity was maintained during multiple cycles of friction testing. Methods utilizing a photoinitiator have been shown to provide coatings with both excellent lubricity and durability.

In some embodiments of the invention, the methods of preparing the compositions for fabrication of articles and/or coated surfaces do not require the use of organic solvents. The use of organic solvents can be physically hazardous. Use of organic solvents can potentially destroy the activity of a bioactive agent that can be optionally included in the natural biodegradable polysaccharide-based composition.

Many of the advantageous features of the present natural biodegradable polysaccharide-containing coatings and articles are thought to be provided by the starting materials, in particular the natural biodegradable polysaccharides having pendent coupling groups. In some aspects the natural biodegradable polysaccharides have pendent polymerizable groups, such as ethylenically unsaturated groups. In a preferred aspect, the degradable polymerizable polymers (macromers) are formed by reacting a natural biodegradable polysaccharide with a compound comprising an ethylenically unsaturated group. For example, in some cases, a natural biodegradable polysaccharide is reacted with a compound including an ethylenically unsaturated group and an isocyanate group. In another example of synthesis, a natural biodegradable polysaccharide is treated with an oxidizing agent to form a reactive aldehyde species on the polysaccharide and then reacted with a compound comprising an ethylenically unsaturated group and an amine group. Polysaccharide macromers were shown to have excellent matrix forming capabilities.

Synthesis can be carried out to provide the natural biodegradable polysaccharide with a desired quantity of pendent coupling groups. It has been found that use of a natural biodegradable polysaccharide having a predetermined amount of the coupling groups allows for the formation of a coating or an article having desirable physical characteristics (for example, the coatings are not brittle). Therefore, in some aspects, the invention provides natural biodegradable polysaccharides having an amount of pendent coupling groups of about 0.7 µmoles of coupling group per milligram of natural biodegradable polysaccharide. Preferably the amount of coupling group per natural biodegradable polysaccharide is in the range of about 0.3 µmoles/mg to about 0.7 µmoles/mg. For example, amylose or maltodextrin can be subject to a synthesis reaction with a compound having an ethylenically unsaturated group to provide an amylose or maltodextrin macromer having a ethylenically unsaturated group load level in the range of about 0.3 µmoles/mg to about 0.7 µmoles/mg.

In some aspects of the invention an initiator is used to promote the formation of the natural biodegradable polysaccharide matrix for article or coating formation. The initiator can be an independent compound or a pendent chemical group used to activate the coupling group pendent from the natural biodegradable polymer and promote coupling of a plurality of natural biodegradable polymers. When the coupling group pendent from the natural biodegradable polysaccharide is a polymerizable group, the initiator can be used in a free radical polymerization reaction to promote crosslinking of the natural biodegradable polysaccharides together in the composition.

Therefore, in one aspect, the invention provides a biodegradable coating or article composition comprising (i) a natural biodegradable polysaccharide, preferably selected from amylose and maltodextrin, comprising a coupling group, (ii) an initiator, and (iii) a bioactive agent, wherein the coupling group is able to be activated by the initiator and promote crosslinking of a plurality of natural biodegradable polysaccharides. In some aspects of the invention the initiator is independent of the natural biodegradable polysaccharide and in other aspects the initiator is pendent from the natural biodegradable polysaccharide. Preferably, the natural biodegradable polysaccharide comprises an ethylenically unsaturated group. In some aspects a photoinitiator is used, such as a photoinitiator that is activated by light wavelengths having no or a minimal effect on the bioactive agent present in the composition.

In another aspect, the initiator includes an oxidizing agent/reducing agent pair, a "redox pair," to drive polymerization of the biodegradable polysaccharide. In preparing the biodegradable coating or article the oxidizing agent and reducing agent are combined in the presence of the biodegradable polysaccharide. One benefit of using a redox pair is that, when combined, the oxidizing agent and reducing agent can provide a particularly robust initiation system. This is advantageous as it can promote the formation of a matrix, for example, useful for coating or article preparation, from biodegradable polysaccharide compositions having a relatively low viscosity. This can be particularly useful in many applications, especially when the biodegradable polysaccharide composition is used for the formation of an in situ polymerized article. For example, a low viscosity composition can be passed through a small gauge delivery conduit with relative ease to provide the composition that can polymerize in situ.

In some aspects of the invention, the viscosity of the composition is above about 5 centi Poise (cP), or about 10 cP or greater. In other aspects of the invention the viscosity of the composition is between about 5 cP or 10 cP and about 700 cP, and in some aspects between about 5 cP or 10 cP and about 250 cP. In some aspects the viscosity of the composition is above about 5 cP or 10 cP and the biodegradable polysaccharides in the composition have an average molecular weight of 500,000 Da or less, 250,000 Da or less, 100,000 Da or less, or 50,000 Da or less.

A method for preparing a coating or article can include the steps of (a) providing a first composition that includes a natural biodegradable polysaccharide comprising a coupling group and a first member of a redox pair (for example, the oxidizing agent) and then (b) mixing the first composition with second composition that includes a second member of the redox pair (for example, the reducing agent). In some aspects the second composition includes a natural biodegradable polysaccharide. For example, the first composition can include (a) a natural biodegradable polysaccharide having a coupling group and an oxidizing agent and the second composition can include a (b) natural biodegradable polysaccharide having a coupling group and a reducing agent. In some aspects, when the first composition is combined with the second composition, the final composition can be about 5 cP or greater.

The oxidizing agent can be selected from inorganic or organic oxidizing agents, including enzymes; the reducing agent can be selected from inorganic or organic reducing agents, including enzymes. Exemplary oxidizing agents include peroxides, including hydrogen peroxide, metal oxides, and oxidases, such as glucose oxidase. Exemplary reducing agents include salts and derivatives of electropositive elemental metals such as Li, Na, Mg, Fe, Zn, Al, and reductases. In one aspect, the reducing agent is present in the composition at a concentration of 2.5 mM or greater when mixed with the oxidizing agent. Other reagents, such as metal or ammonium salts of persulfate, can be present in the composition to promote polymerization of the biodegradable polysaccharide.

A coating or article formed using redox polymerization can therefore comprise a plurality of natural biodegradable polysaccharides associated via polymerized groups, a reduced oxidizing agent, and an oxidized reducing agent. In one preferred aspect, the biodegradable coated layer is formed article having a first coated layer comprising a synthetic polymer.

The invention also provides alternative methods for preparing a coated surface or an article that is biodegradable and that can release a bioactive agent. For example, an alternative method for forming a coating includes disposing in two or more steps at least the following reagents on a surface: (a) a natural biodegradable polysaccharide comprising a first coupling group, (b) a natural biodegradable polysaccharide comprising a second coupling group that is reactive with the first coupling group, and (c) a bioactive agent. According to this method reagents (a) and (b) are reactive with each other and are disposed separately on the surface but can individually include reagent (c). For example, reagent (a) is first disposed on the surface and then a mixture comprising reagent (b) and (c) is then disposed on reagent (a). Reagent (a) reacts with (b) to link the natural biodegradable polysaccharides together to form a coating that includes reagent (c), the bioactive agent. An article can be formed in a similar manner, for example, by a method that includes combining (a) a natural biodegradable polysaccharide comprising a first coupling group with (b) a natural biodegradable polysaccharide comprising a second coupling group that is reactive with the first coupling group, and (c) a bioactive agent. The article can be partially or fully formed when reagent (a) reacts with (b) to link the natural biodegradable polysaccharides together to form the article, which includes reagent (c), the bioactive agent.

In some aspects, the present invention employs the use of biodegradable microparticles that include a bioactive agent and a natural biodegradable polysaccharide, such as amylose and maltodextrin that have pendent coupling groups. The microparticles are used in association with the natural biodegradable polysaccharides to prepare a biodegradable, bioactive agent-releasing coating for the surface of medical devices.

According to this aspect of the invention, a medical device having a coating that includes a crosslinked matrix of natural biodegradable polysaccharides and biodegradable microparticles having a bioactive agent can be placed in the body, and as the biodegradable microparticles degrade the bioactive agent is gradually released from the coating.

The natural biodegradable polysaccharide matrix provides the ability to associate the biodegradable microparticles with the surface of the coated device. In some arrangements, the biodegradable microparticles are dispersed in the natural biodegradable polysaccharide matrix. Such coatings can be formed by disposing a mixture of (a) biodegradable microparticles having a bioactive agent and (b) natural biodegradable polysaccharides having pendent coupling groups, disposing the mixture on a surface, and then treating the composition to form a coated layer wherein the biodegradable microparticles are dispersed within the matrix.

In other arrangements, the coating is formed by disposing the biodegradable microparticles independently of the natural biodegradable polysaccharide having pendent coupling groups. In these arrangements the biodegradable microparticles can be present predominantly one face of the layer that is formed from the natural biodegradable polysaccharide and a microparticle-matrix interface can be formed.

The methods include disposing in one or more steps the following components on a surface: (a) an initiator, (b) a natural biodegradable polysaccharide, preferably selected from amylose and maltodextrin, comprising a coupling group, and (c) biodegradable microparticles comprising a bioactive agent. After the components have been disposed on the surface, the initiator is activated to couple a plurality of natural biodegradable polysaccharide polymers that are present in the composition, thereby forming a natural biodegradable polysaccharide matrix on the surface that is associated with the biodegradable microparticles having the bioactive agent.

In these aspects, the method includes the steps of (i) disposing a composition comprising (a) a natural biodegradable polysaccharide having a coupling group, (b) an initiator, and (c) biodegradable microparticles comprising a bioactive agent on a surface; and (ii) activating the initiator to provide a coated composition having the natural biodegradable polysaccharide and the biodegradable microparticles having the bioactive agent on the surface. Alternatively, the initiator can be disposed independently of the natural biodegradable polysaccharide.

By including microparticles having a bioactive agent in the natural biodegradable polysaccharide-containing coating, the invention also provides a way to effectively and efficiently prepare a variety of drug-delivery coatings. The use of microparticles offers the ability to easily prepare coatings having one or more bioactive agents present in desired amounts in the coating. Such coatings can be prepared by obtaining biodegradable microparticles that have a bioactive agent and then forming a coating that includes the microspheres associated with the natural biodegradable polysaccharide matrix. In some aspects, different microparticles having different bioactive agents can be included in the coating in desired amounts to provide a bioactive agent-releasing coating that is able to release a desired combination of bioactive agents in desired amounts. This is a particular advantage when using bioactive agents that are typically not compatible in the same composition (for example, bioactive agents that have different physical properties).

Microparticles can also be included in articles formed from the natural biodegradable polysaccharide. For example, microparticles can be included in an implantable medical article formed from the natural biodegradable polysaccharides of the invention, or can be included in an article that is formed in situ. In these aspects, the presence of biodegradable microparticles in articles can offer many of the advantages that are offered by the presence of the microparticles in the coatings.

In another aspect, the present invention provides compositions and methods for preparing sealant materials that are particularly useful in connection with implantable medical articles having a porous surface, such as grafts, patches, and wound dressings. In preferred aspects, the inventive compositions can be used to prepare a sealant coating for implantable medical articles, particularly implantable medical articles that include a porous surface.

The sealant coating can provide a barrier to the movement of body fluids, such as blood, near the surface of the coated article. For example, the natural biodegradable polysaccharide-based sealant coating can provide hemostasis at the article surface by formation of a tight seal. Gradually, the natural biodegradable polysaccharide in the sealant coating degrades and a tissue layer is formed as the sealant coating is replaced by cells and other factors involved in tissue repair. During the process of degradation, natural biodegradable polysaccharide degradation products, such as naturally occurring mono- or disaccharides, for example, glucose, are released from the sealant coating, which can be considered an ideal in vivo degradation product because it is commonly found in the body and may also be utilized by the cells involved in tissue repair during the degradation/infiltration process. Gradually, infiltrated tissue growth replaces the function of the natural biodegradable polysaccharide-containing sealant coating.

Another particular advantage of the invention is that release of glucose reduces the likelihood that the process of natural biodegradable polysaccharide degradation and tissue infiltration will promote a strong inflammatory response. This is because the natural biodegradable polysaccharide-based sealant coating can degrade into materials that are non-antigenic or that have low antigenicity. Another advantage is that the degradation products are free of other materials that may cause disease, such as microbial, viral, or prionic materials potentially present in animal-derived preparations (such as bovine collagen preparations).

The sealant compositions of the invention, which include natural biodegradable polysaccharides, such as amylose or maltodextrin polymers, that can be coupled together to form a matrix (at least a portion of the sealant coating) on the medical article, can include a bioactive agent, which can be released as the sealant coating degrades.

In some aspects, the invention provides a biodegradable sealant composition comprising (i) a natural biodegradable polysaccharide comprising a coupling group, and (ii) an initiator, wherein the coupling group is able to be activated by the initiator and promote coupling of a plurality of natural biodegradable polysaccharides. Preferably the natural biodegradable polysaccharide is a polymer such as amylose or maltodextrin. In some aspects the sealant composition can also include a bioactive agent. The initiator can be independent of the natural biodegradable polysaccharide, pendent from the natural biodegradable polysaccharide polymer, or both pendent and independent of the natural biodegradable polysaccharide polymer.

Accordingly, the invention also provides methods for preparing a surface having a sealant coating. The sealant coated surface is prepared on a medical article or article having a porous surface. The methods include disposing in one or more steps the following reagents on a surface: (a) an initiator, and (b) a natural biodegradable polysaccharide comprising a coupling group. In some aspects a bioactive agent is also disposed on the surface. In one preferred aspect, the bioactive agent is a prothrombotic or procoagulant factor. In these aspects, after the components have been disposed on the surface, the initiator is activated to couple the natural biodegradable polysaccharides that are present in the composition, thereby forming a natural biodegradable polysaccharide coating on the surface that includes the bioactive agent.

During the step of activating, the natural biodegradable polysaccharide is contacted with the initiator and the initiator is activated to promote the coupling of two or more natural biodegradable polysaccharides via their coupling groups. In preferred aspects, the natural biodegradable polysaccharide includes a polymerizable group, such as an ethylenically unsaturated group, and initiator is capable of initiating free radical polymerization of the polymerizable groups.

The invention also provides alternative methods for preparing a sealant coating on the surface of an article. The methods include disposing at least the following reagents on a surface: (a) a natural biodegradable polysaccharide comprising a first coupling group and (b) a natural biodegradable polysaccharide comprising a second coupling group, where in the second coupling group is reactive with the first coupling group. According to this method, reagents (a) and (b) are reactive with each other to couple the natural biodegradable polysaccharide, or (a) and/or (b) can be treated to be made reactive with each other. In some aspects (a) and (b) are disposed separately on the surface to form the sealant coating. The natural biodegradable polysaccharide can be the same types of polymers of different types of polymers.

The first coupling group and second coupling group can be a pair of chemical groups that are reactive with one another, preferably specifically reactive. The groups can also become reactive with each other upon addition of a particular agent to the mixture of natural biodegradable polysaccharide having different reactive groups.

DETAILED DESCRIPTION

Figure 1:
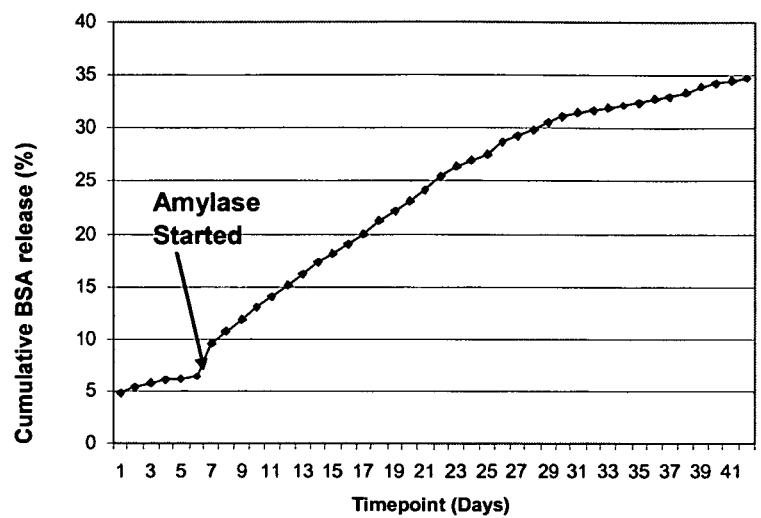
FIG. 1 is a graph of cumulative BSA release from maltodextrin-acrylate filaments treated with amylase, over a period of time.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

In one aspect, the invention provides methods of preparing biodegradable coatings that release bioactive agents from the surface of medical devices. The compositions and methods of the present invention are particularly useful for coating surfaces of implantable medical devices, such as stents and catheters, and that are capable of releasing drugs from the device.

In another aspect, the invention provides methods of preparing biodegradable articles, such as medical implants or in vivo formed matrices. The biodegradable articles can also be used for the release of bioactive agents, and in this manner can function as bioactive agent-releasing implants or depots. In some aspects, the biodegradable articles of the invention biodegrade within a period that is acceptable for the desired application.

In some aspects, the biodegradable article is a medical implant that provides mechanical properties at the implantation site and maintains these mechanical properties until they are no longer needed. After this period of time has elapsed, the medical implant is degraded to an extent that the properties are no longer provided by the medical implant, and the biodegradable components can be absorbed and/or excreted by the body. In some embodiments, the medical implant slowly degrades and transfers stress at the appropriate rate to surrounding tissues as these tissues heal and can accommodate the stress once borne by the medical device.

The biodegradable coating or article includes a natural biodegradable polysaccharide having a coupling group. Exemplary natural biodegradable polysaccharides include amylose and maltodextrin. In some aspects, the present invention provides biodegradable coatings having excellent surface characteristics and that can provide a suitable vehicle for the delivery of bioactive agents. These biodegradable coatings can be disposed on medical devices having a variety of biomaterial surfaces.

In some embodiments of the invention, a coating is formed on a device that includes a biodegradable matrix and biodegradable microparticles, the biodegradable microparticles including one or more bioactive agents. The biodegradable material used to form the matrix includes a natural biodegradable polysaccharide as a component. In the matrix, natural biodegradable polysaccharides such as amylose and maltodextrin are coupled to each other and the biodegradable microparticles are associated with the matrix.

In yet other embodiments of the invention, a sealant coating is formed on a device. The sealant coating includes a biodegradable matrix and optionally one or more bioactive agents, such as prothrombotic agents.

The sealant coating of the invention can, at least initially, provide a barrier on the porous surface that is not permeable to fluids within the body. Gradually, the sealant coating degrades and its function is replaced by tissue that infiltrates the porous surface. Therefore, the sealant coating has particular properties, such as biodegradability and relative impermeability (i.e., relative to the degradation of the sealant coating). The sealant coating can also be compliant and/or conformal, and can have properties such as flexibility, elasticity, and bendability.

As used herein, impermeable, used in relation to the function of the sealant coating, refers to a significant reduction in the transmission of bulk liquid or fluids through the substrate which the sealant coating is associated with. For example, the sealant coating can be impermeable to the transmission of blood. The impermeability can be maintained as the natural biodegradable polysaccharide-based sealant coating degrades, and is replaced by tissue.

As referred to herein, a "natural biodegradable polysaccharide" refers to a non-synthetic polysaccharide that is capable of being enzymatically degraded but that is generally non-enzymatically hydrolytically stable. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include hyaluronic acid, starch, dextran, heparin, chondroitin sulfate, dermatan sulfate, heparan sulfate, keratan sulfate, dextran sulfate, pentosan polysulfate, and chitosan. Preferred polysaccharides are low molecular weight polymers that have little or no branching, such as those that are derived from and/or found in starch preparations, for example, amylose and maltodextrin. Therefore, the natural biodegradable polysaccharide can be a substantially non-branched or non-branched poly(glucopyranose) polymer.

Because of the particular utility of the amylose and maltodextrin polymers, it is preferred that natural biodegradable polysaccharides having an average molecular weight of 500,000 Da or less, 250,000 Da or less, 100,000 Da or less, or 50,000 Da or less. It is also preferred that the natural biodegradable polysaccharides have an average molecular weight of 500 Da or greater. A particularly preferred size range for the natural biodegradable polysaccharides is in the range of about 1000 Da to about 10,000 Da. Natural biodegradable polysaccharides of particular molecular weights can be obtained commercially or can be prepared. The decision of using natural biodegradable polysaccharides of a particular size range may depend on factors such as the physical characteristics of the coating composition (e.g., viscosity), the desired rate of degradation of the coating, the presence of other optional moieties in the coating composition, for example, bioactive agents, etc.

As used herein, "amylose" or "amylose polymer" refers to a linear polymer having repeating glucopyranose units that are joined by $\alpha$-1,4 linkages. Some amylose polymers can have a very small amount of branching via $\alpha$-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by $\alpha$-1,4 linkages to form linear portions and the linear portions are linked together via $\alpha$-1,6 linkages. The branch point linkages are generally greater than 1% of the total linkages and typically 4%-5% of the total linkages. Generally amylopectin derived from plant sources have molecular weights of $1 \times 10^7$ Da or greater.

Amylose can be obtained from, or is present in, a variety of sources. Typically, amylose is obtained from non-animal sources, such as plant sources. In some aspects, a purified preparation of amylose is used as starting material for the preparation of the amylose polymer having coupling groups. In other aspects, as starting material, amylose can be used in a mixture that includes other polysaccharides.

For example, in some aspects, starch preparations having a high amylose content, purified amylose, synthetically prepared amylose, or enriched amylose preparations can be used in the preparation of amylose having the coupling groups. In starch sources, amylose is typically present along with amylopectin, which is a branched polysaccharide. According to the invention, it is preferred to use coating compositions that include amylose, wherein the amylose is present in the composition in an amount greater than amylopectin, if present in the composition. For example, in some aspects, starch preparations having high amylose content, purified amylose, synthetically prepared amylose, or enriched amylose preparations can be used in the preparation of amylose polymer having the coupling groups. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less. In some cases it may be desirable to use non-retrograding starches, such as waxy starch, in the current invention. The amount of amylopectin present in a starch may also be reduced by treating the starch with amylopectinase, which cleaves $\alpha$-1,6 linkages resulting in the debranching of amylopectin into amylose.

In some cases a synthesis reaction can be carried out to prepare an amylose polymer having pendent coupling groups (for example, amylose with pendent ethylenically unsaturated groups) and steps may be performed before, during, and/or after the synthesis to enrich the amount of amylose, or purify the amylose.

Amylose of a particular size, or a combination of particular sizes can be used. The choice of amylose in a particular size range may depend on the application, for example, the type of surface coated or the porosity of the surface. In some embodiments amylose having an average molecular weight of 500, 000 Da or less, 250,000 Da or less, 100,000 Da or less, 50,000 Da or less, preferably greater than 500 Da, or preferably in the range of about 1000 Da to about 10,000 Da is used. Amylose of particular molecular weights can be obtained commercially or can be prepared. For example, synthetic amyloses with average molecular masses of 70, 110, 320, and 1,000 kDa can be obtained from Nakano Vinegar Co., Ltd. (Aichi, Japan). The decision of using amylose of a particular size range may depend on factors such as the physical characteristics of the coating composition (e.g., viscosity), the desired rate of degradation of the coating, the presence of other optional moieties in the coating composition (for example, bioactive agents, etc.), etc.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate×100.

A starch preparation that has been totally hydrolyzed to dextrose (glucose) has a DE of 100, where as starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500-5000 Da are commercially available (for example, from CarboMer, San Diego, Calif.).

Another contemplated class of natural biodegradable polysaccharides is natural biodegradable non-reducing polysaccharides. A non-reducing polysaccharide can provide an inert matrix thereby improving the stability of sensitive bioactive agents, such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide comprises polyalditol which is available from GPC (Muscatine, Iowa). In another aspect, the polysaccharide is a glucopyranosyl polymer, such as a polymer that includes repeating (1→3)O-β-D-glucopyranosyl units.

In some aspects, the coating compositions can include natural biodegradable polysaccharides that include chemical modifications other than the pendent coupling group. To exemplify this aspect, modified amylose having esterified hydroxyl groups can be prepared and used in sealant coating compositions in association with the methods of the invention. Other natural biodegradable polysaccharides having hydroxyl groups may be modified in the same manner. These types of modifications can change or improve the properties of the natural biodegradable polysaccharide making for a coating composition that is particularly suitable for a desired application. Many chemically modified amylose polymers, such as chemically modified starch, have at least been considered acceptable food additives.

As used herein, "modified natural biodegradable polysaccharides" refers to chemical modifications to the natural biodegradable polysaccharide that are different than those provided by the coupling group or the initiator group. Modified amylose polymers having a coupling group (and/or initiator group) can be used in the compositions and methods of the invention.

To exemplify this aspect, modified amylose is described. By chemically modifying the hydroxyl groups of the amylose, the physical properties of the amylose can be altered. The hydroxyl groups of amylose allow for extensive hydrogen bonding between amylose polymers in solution and can result in viscous solutions that are observed upon heating and then cooling amylose-containing compositions such as starch in solution (retrograding). The hydroxyl groups of amylose can be modified to reduce or eliminate hydrogen bonding between molecules thereby changing the physical properties of amylose in solution.

Therefore, in some embodiments the natural biodegradable polysaccharides, such as amylose, can include one or more modifications to the hydroxyl groups wherein the modifications are different than those provided by coupling group. Modifications include esterification with acetic anhydride (and adipic acid), succinic anhydride, 1-octenylsuccinic anhydride, phosphoryl chloride, sodium trimetaphosphate, sodium tripolyphosphate, and sodium monophosphate; etherification with propylene oxide, acid modification with hydrochloric acid and sulfuric acids; and bleaching or oxidation with hydrogen peroxide, peracetic acid, potassium permanganate, and sodium hypochlorite.

Examples of modified amylose polymers include carboxymethyl amylose, carboxyethyl amylose, ethyl amylose, methyl amylose, hydroxyethyl amylose, hydroxypropyl amylose, acetyl amylose, amino alkyl amylose, allyl amylose, and oxidized amylose. Other modified amylose polymers include succinate amylose and oxtenyl succinate amylose.

In another aspect of the invention, the natural biodegradable polysaccharide is modified with a hydrophobic moiety in order to provide a biodegradable matrix having hydrophobic properties. Exemplary hydrophobic moieties include those previously listed, fatty acids and derivatives thereof, and $C_2$-$C_{18}$ alkyl chains. A polysaccharide, such as amylose or maltodextrin, can be modified with a compound having a hydrophobic moiety, such as a fatty acid anhydride. The hydroxyl group of a polysaccharide can also cause the ring opening of lactones to provide pendent open-chain hydroxy esters.

In some aspects, the hydrophilic moiety pendent from the natural biodegradable has properties of a bioactive agent. The hydrophilic moiety can be hydrolyzed from the natural biodegradable polymer and released from the matrix to provide a therapeutic effect. One example of a therapeutically useful hydrophilic moiety is butyric acid, which has been shown to elicit tumor cell differentiation and apoptosis, and is thought to be useful for the treatment of cancer and other blood diseases. The hydrophilic moiety that provides a therapeutic effect can also be a natural compound (such as butyric acid). Therefore, degradation of the matrix having a coupled therapeutic agent can result in all natural degradation products.

According to the invention, a natural biodegradable polysaccharide that includes a coupling group is used to form an article or a coating on the surface of a medical article. Other polysaccharides can also be present in the coating composition. For example, the two or more natural biodegradable polysaccharides are used to form an article or a coating on the surface of a medical article. Examples include amylose and one or more other natural biodegradable polysaccharide(s), and maltodextrin and one or more other natural biodegradable polysaccharide(s); in one aspect the composition includes a mixture of amylose and maltodextrin, optionally with another natural biodegradable polysaccharide.

In one preferred embodiment, amylose or maltodextrin is the primary polysaccharide. In some embodiments, the composition includes a mixture of polysaccharides including amylose or maltodextrin and the amylose or maltodextrin content in the mixture of polysaccharides is 50% or greater, 60% or greater, 70% or greater, 80% or greater, or 85% or greater by weight.

Purified or enriched amylose preparations can be obtained commercially or can be prepared using standard biochemical techniques such as chromatography. In some aspects, high-amylose cornstarch can be used.

As used herein, "coupling group" can include (1) a chemical group that is able to form a reactive species that can react with the same or similar chemical group to form a bond that is able to couple the natural biodegradable polysaccharides together (for example, wherein the formation of a reactive species can be promoted by an initiator); or (2) a pair of two different chemical groups that are able to specifically react to form a bond that is able to couple the natural biodegradable polysaccharides together. The coupling group can be attached to any suitable natural biodegradable polysaccharide, including the amylose and maltodextrin polymers as exemplified herein.

Contemplated reactive pairs include Reactive Group A and corresponding Reactive Group B as shown in the Table 1 below. For the preparation of a coating composition, a reactive group from group A can be selected and coupled to a first set of natural biodegradable polysaccharides and a corresponding reactive group B can be selected and coupled to a second set of natural biodegradable polysaccharides. Reactive groups A and B can represent first and second coupling groups, respectively. At least one and preferably two, or more than two reactive groups are coupled to an individual natural biodegradable polysaccharide polymer. The first and second sets of natural biodegradable polysaccharides can be combined and reacted, for example, thermochemically, if necessary, to promote the coupling of natural biodegradable polysaccharides and the formation of a natural biodegradable polysaccharide matrix.

TABLE 1

| Reactive group A | Reactive group B |
| --- | --- |
| amine, hydroxyl, sulfhydryl | N-oxysuccinimide ("NOS") |
| amine | Aldehyde |
| amine | Isothiocyanate |
| amine, sulfhydryl | Bromoacetyl |
| amine, sulfhydryl | Chloroacetyl |
| amine, sulfhydryl | Iodoacetyl |
| amine, hydroxyl | Anhydride |
| aldehyde | Hydrazide |
| amine, hydroxyl, carboxylic acid | Isocyanate |
| amine, sulfhydryl | Maleimide |
| sulfhydryl | Vinylsulfone |

Amine also includes hydrazide (R—NH—NH$_2$)

For example, a suitable coupling pair would be a natural biodegradable polysaccharide having an electrophilic group and a natural biodegradable polysaccharide having a nucleophilic group. An example of a suitable electrophilic-nucleophilic pair is N-hydroxysuccinimide-amine pair, respectively. Another suitable pair would be an oxirane-amine pair.

In some aspects, the natural biodegradable polysaccharides of the invention include at least one, and more typically more than one, coupling group per natural biodegradable polysaccharide, allowing for a plurality of natural biodegradable polysaccharides to be coupled in linear and/or branched manner. In some preferred embodiments, the natural biodegradable polysaccharide includes two or more pendent coupling groups.

In some aspects, the coupling group on the natural biodegradable polysaccharide is a polymerizable group. In a free radical polymerization reaction the polymerizable group can couple natural biodegradable polysaccharides together in the composition, thereby forming a biodegradable natural biodegradable polysaccharide matrix.

A preferred polymerizable group is an ethylenically unsaturated group. Suitable ethylenically unsaturated groups include vinyl groups, acrylate groups, methacrylate groups, ethacrylate groups, 2-phenyl acrylate groups, acrylamide groups, methacrylamide groups, itaconate groups, and styrene groups. Combinations of different ethylenically unsaturated groups can be present on a natural biodegradable polysaccharide, such as amylose or maltodextrin.

In preparing the natural biodegradable polysaccharide having pendent coupling groups any suitable synthesis procedure can be used. Suitable synthetic schemes typically involve reaction of, for example, hydroxyl groups on the natural biodegradable polysaccharide, such as amylose or maltodextrin. Synthetic procedures can be modified to produce a desired number of coupling groups pendent from the natural biodegradable polysaccharide backbone. For example, the hydroxyl groups can be reacted with a coupling group-containing compound or can be modified to be reactive with a coupling group-containing compound. The number and/or density of acrylate groups can be controlled using the present method, for example, by controlling the relative concentration of reactive moiety to saccharide group content.

In some modes of practice, the biodegradable polysaccharides have an amount of pendent coupling groups of about 0.7 μmoles of coupling group per milligram of natural biodegradable polysaccharide. In a preferred aspect, the amount of coupling group per natural biodegradable polysaccharide is in the range of about 0.3 μmoles/mg to about 0.7 μmoles/mg. For example, amylose or maltodextrin can be reacted with an acrylate groups-containing compound to provide an amylose or maltodextrin macromer having a acrylate group load level in the range of about 0.3 μmoles/mg to about 0.7 μmoles/mg.

As used herein, an "initiator" refers to a compound, or more than one compound, that is capable of promoting the formation of a reactive species from the coupling group. For example, the initiator can promote a free radical reaction of natural biodegradable polysaccharide having a coupling group. In one embodiment the initiator is a photoreactive group (photoinitiator) that is activated by radiation. In some embodiments, the initiator can be an "initiator polymer" that includes a polymer having a backbone and one or more initiator groups pendent from the backbone of the polymer.

In some aspects the initiator is a compound that is light sensitive and that can be activated to promote the coupling of the amylose polymer via a free radical polymerization reaction. These types of initiators are referred to herein as "photoinitiators." In some aspects it is preferred to use photoinitiators that are activated by light wavelengths that have no or a minimal effect on a bioactive agent if present in the composition. A photoinitiator can be present in a sealant composition independent of the amylose polymer or pendent from the amylose polymer.

In some embodiments, photoinitiation occurs using groups that promote an intra- or intermolecular hydrogen abstraction reaction. This initiation system can be used without additional energy transfer acceptor molecules and utilizing nonspecific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, and camphorquinone.

In some preferred embodiments the photoinitiator includes one or more charged groups. The presence of charged groups can increase the solubility of the photoinitiator (which can contain photoreactive groups such as aryl ketones) in an aqueous system and therefore provide for an improved coating composition. Suitable charged groups include, for example, salts of organic acids, such as sulfonate, phosphonate, carboxylate, and the like, and onium groups, such as quaternary ammonium, sulfonium, phosphonium, protonated amine, and the like. According to this embodiment, a suitable photoinitiator can include, for example, one or more aryl ketone photogroups selected from acetophenone, benzophenone, anthraquinone, anthrone, anthrone-like heterocycles, and derivatives thereof; and one or more charged groups, for example, as described herein. Examples of these types of water-soluble photoinitiators have been described in U.S. Pat. No. 6,077,698.

In some aspects the photoinitiator is a compound that is activated by long-wavelength ultraviolet (UV) and visible light wavelengths. For example, the initiator includes a photoreducible or photo-oxidizable dye. Photoreducible dyes can also be used in conjunction with a compound such as a tertiary amine. The tertiary amine intercepts the induced triplet producing the radical anion of the dye and the radical cation of the tertiary amine. Examples of molecules exhibiting photosensitization reactivity and useful as an initiator include acridine orange, camphorquinone, ethyl eosin, eosin Y, erythrosine, fluorescein, methylene green, methylene blue, phloxime, riboflavin, rose bengal, thionine, and xanthine dyes. Use of these types of photoinitiators can be particularly advantageous when a light-sensitive bioactive agent is included in the sealant coating.

Therefore, in yet another aspect, the invention provides a coating composition comprising (i) a natural biodegradable polysaccharide comprising an ethylenically unsaturated group (ii) a photoinitiator selected from the group consisting of acridine orange, camphorquinone, ethyl eosin, eosin Y, erythrosine, fluorescein, methylene green, methylene blue, phloxime, riboflavin, rose bengal, thionine, and xanthine dyes, and (iii) a bioactive agent.

Thermally reactive initiators can also be used to promote the polymerization of natural biodegradable polymers having pendent coupling groups. Examples of thermally reactive initiators include 4,4' azobis(4-cyanopentanoic acid), 2,2-azobis[2-(2-imidazolin-2-yl)propane]dihydrochloride, and analogs of benzoyl peroxide. Redox initiators can also be used to promote the polymerization of the natural biodegradable polymers having pendent coupling groups. In general, combinations of organic and inorganic oxidizers, and organic and inorganic reducing agents are used to generate radicals for polymerization. A description of redox initiation can be found in *Principles of Polymerization*, 2$^{nd}$ Edition, Odian G., John Wiley and Sons, pgs 201-204, (1981).

In some cases, the initiator can be included in a base coating and the natural biodegradable polysaccharide or composition that includes the natural biodegradable polysaccharide can be disposed on the base coating. For example, a coated layer that includes the natural biodegradable polysaccharide can be formed on a coated layer that includes a synthetic polymer. The synthetic polymer can be a hydrophilic polymer such as poly(vinylpyrrolidone), poly(acrylamide), or copolymers thereof. In some aspects the synthetic polymer is formed using photoreactive groups, such as photoreactive groups that are pendent from the synthetic polymer, which can be used to covalently bond the synthetic polymer to a surface of the article.

In some aspects the polymerization initiator is a polymer that includes an initiator group (herein referred to as an "initiator polymer"). The polymeric portion of the initiator polymer can be obtained or prepared to have particular properties or features that are desirable for use with a coating composition, such as a sealant coating composition. For example, the polymeric portion of the initiator polymer can have hydrophilic or amphoteric properties, it can include pendent charged groups, or it can have groups that allow it to interact with a particular surface (this can depend on the type of surface to be coated). Optionally, or additionally, the polymer can change or improve the properties of the coating that is formed by the amylose polymer having coupling groups. For example, the initiator polymer can change the elasticity, flexibility, wettability, or softness (or combinations thereof) of the coating formed on the surface. Certain polymers, as described herein, are useful as plasticizing agents for coatings that include natural biodegradable polysaccharides. Initiator groups can be added to these plasticizing polymers and used in the compositions and methods of the invention.

For example, in some aspects an initiator can be pendent from a natural biodegradable polysaccharide. Therefore, the natural biodegradable polysaccharide is able to promote activation of polymerizable groups that are pendent from other natural biodegradable polysaccharides and promote the formation of a natural biodegradable polysaccharide matrix.

In other cases, the polymeric portion of the initiator polymer can include, for example, acrylamide and methacrylamide monomeric units, or derivatives thereof. In some embodiments, the coating composition includes an initiator polymer having a photoreactive group and a polymeric portion selected from the group of acrylamide and methacrylamide polymers and copolymers.

In some aspects, the initiator includes an oxidizing agent/reducing agent pair, a "redox pair," to drive polymerization of the biodegradable polysaccharide. In this case, polymerization of the biodegradable polysaccharide is carried out upon combining one or more oxidizing agents with one or more reducing agents. Other compounds can be included in the composition to promote polymerization of the biodegradable polysaccharides.

When combined, the oxidizing agent and reducing agent can provide a particularly robust initiation system and can drive the formation of a polymerized matrix of polysaccharides from a composition having a low viscosity. A polysaccharide composition with a low viscosity may be due to a low concentration of polysaccharide in the composition, a polysaccharide having a low average molecular weight, or combinations thereof. Matrix formation from a polysaccharide composition having a low viscosity is particularly advantageous in many applications, especially for in situ polymerization. In some aspects of the invention, a low viscosity polysaccharide composition is passed through a small gauge delivery conduit, such as a needle, wherein the redox pair causes the polymerization of the polysaccharides in situ.

In some aspects of the invention, the viscosity of the composition is above about 5 cP, or about 10 cP or greater. In other aspects of the invention the viscosity of the composition is between about 5 cP or 10 cP and about 700 cP, or between about 5 cP or 10 cP and about 250 cP.

In order to promote polymerization of the biodegradable polysaccharides in a composition to form a matrix, the oxidizing agent is added to the reducing agent in the presence of the one or more biodegradable polysaccharides. For example, a composition including a biodegradable polysaccharide and a reducing agent is added to a composition including an oxidizing agent, or a composition including a biodegradable polysaccharide and an oxidizing agent is added to a composition containing a reducing agent. One desirable method of preparing a matrix is to combine a composition including a biodegradable polysaccharide and an oxidizing agent with a composition including a biodegradable polysaccharide and a reducing agent. For purposes of describing this method, the terms "first composition" and "second composition" can be used.

The viscosities of biodegradable polysaccharide in the first and second compositions can be the same or can be different. Generally, though, it has been observed that good mixing and subsequent matrix formation is obtained when the compositions have the same or similar viscosities. In this regard, if the same biodegradable polymer is used in the first and second compositions, the concentration of the biodegradable polymer may be the same or different.

The oxidizing agent can be selected from inorganic or organic oxidizing agents, including enzymes; the reducing agent can be selected from inorganic or organic reducing agents, including enzymes. Exemplary oxidizing agents include peroxides, including hydrogen peroxide, metal oxides, and oxidases, including glucose oxidase. Exemplary reducing agents include salts and derivatives of electropositive elemental metals such as Li, Na, Mg, Fe, Zn, Al, and reductases. In one mode of practice, the reducing agent is present at a concentration of about 2.5 mM or greater when the reducing agent is mixed with the oxidizing agent. Prior to mixing, the reducing agent can be present in a composition at a concentration of, for example, 5 mM or greater.

Other reagents can be present in the composition to promote polymerization of the biodegradable polysaccharide. Other polymerization promoting compounds can be included in the composition, such as metal or ammonium salts of persulfate.

Optionally, the compositions and methods of the invention can include polymerization accelerants that can improve the efficiency of polymerization. Examples of useful accelerants include N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the coating composition.

In some aspects, an aqueous composition that includes the natural biodegradable polysaccharide, such as amylose or maltodextrin having pendent coupling groups, and a bioactive agent is obtained and used in the method of coating a surface. In another aspect, an aqueous composition is used to form an article. This composition can be prepared by mixing a bioactive agent, such as a water-soluble small molecule, a protein, or a nucleic acid, with the natural biodegradable polysaccharide.

According to the invention, the natural biodegradable polysaccharide that includes a coupling group is used to form a coating on the surface of a medical device or to form an article. Other polysaccharides can also be present in the coating composition. For example, the coating can include two different natural biodegradable polysaccharides, or more than two different natural biodegradable polysaccharides. For example, in some cases the natural biodegradable polysaccharide (such as amylose or maltodextrin) can be present in the coating or article composition along with another biodegradable polymer (i.e., a secondary polymer), or more than one other biodegradable polymer. An additional polymer or polymers can be used to alter the properties of the matrix, or serve as bulk polymers to alter the volume of the matrix. For example, other biodegradable polysaccharides can be used in combination with the amylose polymer. These include hyaluronic acid, dextran, starch, amylose (for example, non-derivitized), amylopectin, cellulose, xanthan, pullulan, chitosan, pectin, inulin, alginates, and heparin.

In some aspects of the invention, a composition is disposed on a surface that includes at least the natural biodegradable polysaccharide, such as amylose or maltodextrin having a coupling group and a bioactive agent. In some embodiments the composition includes the natural biodegradable polysaccharide, a bioactive agent, and an initiator. In other embodiments, a coating is formed by disposing the natural biodegradable polysaccharide and disposing the biodegradable microparticles on a surface. In some embodiments a composition containing both the natural biodegradable polysaccharide and the biodegradable microparticles having the bioactive agent are disposed on a surface. In yet other embodiments of the invention, a sealant composition that includes at least the natural biodegradable polysaccharide having a coupling group is disposed on a porous surface.

The concentration of the natural biodegradable polysaccharide in the composition can be chosen to provide a coating or an article having a desired density of crosslinked natural biodegradable polysaccharide. In some embodiments, the concentration of natural biodegradable polysaccharide in the composition can depend on the type or nature of the bioactive agent that is included in the composition. In some embodiments the natural biodegradable polysaccharide having the coupling groups is present in the coating composition at a concentration in the range of 5-100% (w/v), and 5-50%, and in more specific embodiments in the range of 10-20% and in other embodiments in the range of 20-50% (w/v).

For example, in forming a medical implant, the concentration of the natural biodegradable polysaccharide may be higher to provide a more structurally rigid implant.

Other polymers or non-polymeric compounds can be included in the composition that can change or improve the properties of the coating or article that is formed by the natural biodegradable coating having coupling groups in order to change the elasticity, flexibility, wettability, or adherent properties, (or combinations thereof) of the coating formed on the surface.

For example, in order to improve the properties of a coating, such as a sealant coating when formed, it is possible to include in the mixture one or a combination of plasticizing agents. Suitable plasticizing agents include glycerol, diethylene glycol, sorbitol, sorbitol esters, maltitol, sucrose, fructose, invert sugars, corn syrup, and mixtures thereof. The amount and type of plasticizing agents can be readily determined using known standards and techniques.

Compositions of this invention can be used to coat the surface of a variety of implantable devices. The coating of natural biodegradable polysaccharide (with or without bioactive agent) can be applied to a medical device using standard techniques to cover the entire surface of the device, or a portion of the device surface.

The medical articles on which the biodegradable coating can be formed can be fabricated from any suitable biomaterial or combinations of biomaterials. Preferred biomaterials include those formed of synthetic polymers, including oligomers, homopolymers, and copolymers resulting from either addition or condensation polymerizations.

Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride.

Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Other suitable biomaterials include metals, metal alloys, and ceramics. The metals and metal alloys include, but are not limited to, titanium, Nitinol, stainless steel, tantalum, and cobalt chromium. A second class of metals includes the noble metals such as gold, silver, copper, and platinum uridium. The ceramics include, but are not limited to, silicon nitride, silicon carbide, zirconia, and alumina, as well as glass, silica, and sapphire. Combinations of ceramics and metals are another class of biomaterials.

Certain natural materials are also suitable biomaterials, including human tissue such as bone, cartilage, skin and teeth; and other organic materials such as wood, cellulose, compressed carbon, and rubber.

The surface of such biomaterials can be pretreated (for example, with a Parylene coating composition) in order to alter the surface properties of the biomaterial, when desired.

The biomaterials as described herein can be used to fabricate a variety of implantable devices on which the biodegradable coating can be formed. The medical device can be any device that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles or atria of the heart. The device can be a biostable device, a partially degradable device, or a completely degradable device (for example, stents can be fabricated from biodegradable polymeric materials).

The natural biodegradable polysaccharide coating (in some embodiments including biodegradable microparticles) can be formed on the surface of virtually any implantable device. Exemplary implantable devices include but are not limited to drug-delivering vascular stents; other vascular devices (e.g., grafts, catheters, valves, artificial hearts, heart assist devices); implantable defibrillators; blood oxygenator devices; surgical devices; tissue-related materials; membranes; cell culture devices; chromatographic support materials; biosensors; shunts for hydrocephalus; wound management devices; endoscopic devices; infection control devices; orthopedic devices; dental devices, urological devices; colostomy bag attachment devices; ophthalmic devices; glaucoma drain shunts; synthetic prostheses; intraocular lenses; respiratory, peripheral cardiovascular, spinal, neurological, dental, and ear/nose/throat devices (e.g., ear drainage tubes); renal devices; and dialysis articles (e.g., tubing, membranes, grafts).

Other contemplated devices include self-expanding stents (e.g., made from nitinol), balloon-expanded stents (e.g., prepared from stainless steel), degradable coronary stents, non-degradable coronary stents, peripheral coronary stents, urinary catheters (e.g., surface-coated with antimicrobial agents), penile implants, sphincter devices, urethral devices, bladder devices, renal devices, vascular implants and grafts, intravenous catheters (e.g., treated with antithrombotic agents), small diameter grafts, artificial lung catheters, electrophysiology catheters, anastomosis devices, vertebral disks, bone pins, suture anchors, hemostatic barriers, clamps, surgical staples/sutures/screws/plates/clips, atrial septal defect closures, electro-stimulation leads for cardiac rhythm management (e.g., pacer leads), glucose sensors (long-term and short-term), blood pressure and stent graft catheters, blood oxygenator tubing, blood oxygenator membranes, blood bags, birth control devices, breast implants, benign prostatic hyperplasia and prostate cancer implants, bone repair/augmentation devices, breast implants, cartilage repair devices, orthopedic joint implants, orthopedic fracture repairs, tissue adhesives, tissue sealants, tissue scaffolds, cerebral spinal fluid (CSF) shunts, dental implants, dental fracture repair devices, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, central venous access catheters, hemodialysis devices, catheter cuffs, anastomotic closures, vascular access catheters, cardiac sensors, uterine bleeding patches, urological catheters/stents/implants, in vitro diagnostics, aneurysm exclusion devices, neuropatches, Vena cava filters, urinary dialators, endoscopic surgical tissue extractors, atherectomy catheters, clot extraction catheters, percutaneous transluminal angioplasty (PTA) catheters, percutaneous transluminal coronary angioplasty (PTCA) catheters, stylets (vascular and non-vascular), coronary guidewires, drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

The compositions are particularly useful for forming biodegradable coatings on the surface of devices that will come in contact with aqueous systems. The body fluids typically have enzymes that allow for the degradation of the natural biodegradable polysaccharide-based coating. The aqueous system (such as bodily fluids) allows for the degradation of the biodegradable coating and release of the bioactive agent from the device. In some cases, depending on the bioactive agent and the matrix, the bioactive agent can diffuse out of the matrix. For example, it has been demostrated that a loosely formed matrix may allow some diffusion of bioactive agents, particularly smaller bioactive agents. More desirably, well-formed matrices having signification polysaccharide association via coupling groups are able to retain bioactive agents. Release of bioactive agents from these matrices is mediated by enzymatic degradation.

The coatings can also be formed on a biological article. A "biological article" refers to any sort of non-synthetic biologically-based article such as a cell or a portion of a cell, a group of cells, tissue, or an organ or a portion of a organ. The present reagents can be used in methods for encapsulating cellular material.

In some aspects of the invention, a sealant coating is provided on a porous surface of a medical article. The medical article can be any article that is introduced into a mammal for the prophylaxis or treatment of a medical condition, wherein the medical article include a sealant coating (at least initially) and has a sealant function. The medical article having the sealant coating can provide one or more functions, including providing a barrier to the movement of body fluids, such as blood.

The sealant coatings can be formed on the surface of articles that have a porous structure wherein it is desired to seal the porous structure, providing a barrier to the movement of body fluids. In many cases it is desirable to form these artificial barriers to ensure that the implanted article functions as it is intended to in the body. Gradually, however, it is desired to allow the body to maintain the function of the sealant coating by replacing the sealant barrier materials with natural materials from the body.

The sealant composition can be prepared and/or applied in such a manner as to fill the pores on the surface of the article with the sealant material. This can be achieved by, for example, controlling factors such as the viscosity of the coating composition and the coupling of the natural biodegradable polysaccharides during formation of the coating.

An article having a "porous surface" refers to any article having a surface with pores on which a natural biodegradable polysaccharide-based sealant coating can be formed. The pores are preferably of a physical dimension that permits in-growth of tissue into the pores as the sealant coating degrades. The porous surface can be associated with a non-porous surface, such as a scaffold that can provide support to the porous surface.

The medical article can include porous surfaces that can be provided with a sealant coating and non-porous surfaces that are not coated with the sealant coating, optionally coated with the sealant coating, or coated with a material that is different than the sealant coating. All or a portion of the porous surfaces can be coated with the sealant coating. In some cases a sealant material that is different than the natural biodegradable polysaccharide-based sealant material can be used in conjunction with the natural biodegradable polysaccharide-based sealant material.

For articles that have interior and exterior porous surfaces, either the interior or the exterior portions can be coated, or portions of the interior and/or exterior can be coated. The portion or portions of the article that are coated can depend on a particular desired application or function of the coated article. For example, in some cases it may be desirable to have a difference in the flow of fluids, such as blood, through porous portions of the medical article. Also, tissue in-growth on selected portions of the article can also be promoted by depositing the sealant coating at desired locations.

The porous surface of the article can also include a material that is thrombogenic and/or presents surface stasis areas (regions of minimized or no blood flow). Depending on the application, a surface having a desired degree of porosity is obtained. The surface will have a degree of porosity sufficient for proper in-growth of cells and tissue forming factors. Upon tissue in-growth, the surface can provide a barrier that is fluid impermeable.

In many cases the porous surface of the article is a fabric or has fabric-like qualities. The porous surface can be formed from textiles, which include woven materials, knitted materials, and braided materials. Particularly useful textile materials are woven materials which can be formed using any suitable weave pattern known in the art.

The porous surface can be that of a graft, sheath, cover, patch, sleeve, wrap, casing, and the like. These types of articles can function as the medical article itself or be used in conjunction with another part of a medical article (examples of which are described herein).

The porous surface can include any suitable type of biomaterial. Useful biomaterials can be woven into fibers for the preparation of fabrics as described herein. Useful materials include synthetic addition or condensation polymers such as polyesters, polypropylenes, polyethylenes, polyurethanes, and polytetrafluoroethylenes. Polyethylene terephthalate (PET) is a commonly used polymer in fabrics. Blends of these polymers can also be utilized in the preparation of fibers, such as monofilament or multi-filament fibers, for the construction of fabrics. Commonly used fabrics include those such as nylon, velour, and DACRON™.

The fabrics can optionally include stiffening materials to improve the physical properties of the article, for example, to improve the strength of a graft. Such materials can improve the function of an implanted article. For example, strengthening materials can improve the patency of the graft.

Porous surfaces can also be formed by dipping mandrels in these types of polymers.

Other particular contemplated porous surfaces include those of cardiac patches. These can be used to decrease suture line bleeding associated with cardiovascular reconstructions. The patches can be used to seal around the penetrating suture. Common materials used in cardiac patches include PTFE and DACRON™.

The thickness of the material used as the porous surface can be chosen depending on the application. However, it is common that these thicknesses are about 1.0 mm or less on average, and typically in the range of about 0.10 mm to about 1.0 mm.

Other particular contemplated porous surfaces include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. No. 4,047,252; U.S. Pat. No. 5,178,630; U.S. Pat. No. 5,282,848; and U.S. Pat. No. 5,800,514.

The natural biodegradable polysaccharide can be used to provide a sealant coating to a wide variety of articles. As used herein, "article" is used in its broadest sense and includes objects such as devices. Such articles include, but are not limited to vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parental feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; birth control devices; breast implants; cardiac sensors; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, the polymeric compositions can be utilized in connection with an ophthalmic article. The ophthalmic article can be configured for placement at an external or internal site of the eye. Suitable ophthalmic articles in accordance with these aspects can provide bioactive agent to any desired area of the eye. In some aspects, the articles can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired. The biodegradable polysaccharide compositions can be used either for the formation of a coating on the surface of an ophthalmic article, or in the construction of an ophthalmic article.

Suitable external articles can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Articles configured for placement at an internal site of the eye can reside within any desired area of the eye. In some aspects, the ophthalmic article can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and U.S. application Ser. No. 11/204,195 (filed Aug. 15, 2005, Anderson et al.), Ser. No. 11/204,271 (filed Aug. 15, 2005, Anderson et al.), Ser. No. 11/203,981 (filed Aug. 15, 2005, Anderson et al.), Ser. No. 11/203,879 (filed Aug. 15, 2005, Anderson et al.), Ser. No. 11/203,931 (filed Aug. 15, 2005, Anderson et al.); and related applications.

In some aspects of the invention, the biodegradable polysaccharide coating is included on a non-linear intraocular device. In some aspects of the invention, the biodegradable polysaccharide coating includes a bioactive agent, such as a high molecular weight bioactive agent useful for treating an ocular condition.

In some aspects, the ophthalmic article can be configured for placement, or can be formed, at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

In some aspects, the invention provides a biodegradable implant that is formed from the biodegradable polysaccharide and that includes a bioactive agent, such as a high molecular weight bioactive agent useful for treating an ocular condition.

In some aspects, the invention provides a method for forming an article from the biodegradable polysaccharide, wherein the method includes polymerizing a composition that includes the biodegradable polysaccharide within the eye, such as in a subretinal area or within the vitreous. For example, a low viscosity composition including a natural biodegradable polysaccharide and a redox pair to promote polymerization for in situ matrix formation.

Ophthalmic articles can also be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

A medical article having a biodegradable coating can also be prepared by assembling an article having two or more "parts" (for example, pieces of a medical article that can be put together to form the article) wherein at least one of the parts has a biodegradable coating. All or a portion of the part of the medical article can have a biodegradable coating. In this regard, the invention also contemplates parts of medical article (for example, not the fully assembled article) that have a natural biodegradable polysaccharide-based coating.

In some aspects of the invention the natural biodegradable polymer is used to form the body member of a medical implant, wherein the body member has a wet weight of about 10 g or less, or a dry weight of about 2.5 g or less.

The device can also have a base coating of material. The base coating can serve one or more functions, for example, it can provide an improved surface for the natural biodegradable polysaccharide or composition that includes the natural biodegradable polysaccharide. The base coating can include a polymeric material, such as a natural or synthetic polymer. Examples of suitable compounds that can be used to pretreat a surface to provide a base coat include Parylene and organosilane compounds. Suitable base coatings can include, for example, methacrylate, acrylate, alkylacrylate, acrylamide, vinylpyrrolidinone, vinylacetamide, and vinyl formamide based polymers and copolymers. These polymers can also include latent reactive groups such as photoreactive groups.

Base coatings can be useful in various coating processes. For example, in some aspects, biodegradable microparticles can be first disposed on a base coat and then the natural biodegradable polysaccharide having coupling groups can be disposed on the microparticles. The surface can then be treated to form a coating wherein the microparticles are predominantly located between the base layer and the layer formed from the natural biodegradable polysaccharide having coupling groups. If desired, an initiator can be included in a base coating and the natural biodegradable polysaccharide polymer or composition that includes the natural biodegradable polysaccharide polymer can be disposed on the base coating. The base coating can serve one or more functions, for example, it can provide an improved surface for the natural biodegradable polysaccharide or composition that includes the natural biodegradable polysaccharide.

In many aspects of the invention, the natural biodegradable polysaccharide coating or the biodegradable article includes one or more bioactive agents. The bioactive agent can be dispersed within the natural biodegradable polysaccharide coating or biodegradable article itself. Alternatively, the bioactive agent can be present in microparticles that are associated with the natural biodegradable polysaccharide coating. The bioactive agent can be delivered from the coated surface upon degradation of the natural biodegradable polysaccharide and/or biodegradable microparticles.

The term "bioactive agent" refers to a peptide, protein, carbohydrate, nucleic acid, lipid, polysaccharide, synthetic inorganic or organic molecule, viral particle, cell, or combinations thereof, that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include (a) therapeutic nucleic acids, including antisense DNA, antisense RNA, and interference RNA, and (b) nucleic acids encoding therapeutic gene products, including plasmid DNA and viral fragments, along with associated promoters and excipients. Examples of other molecules that can be incorporated include nucleosides, nucleotides, vitamins, minerals, and steroids.

Although not limited to such, the coatings of the invention are particularly useful for delivering bioactive agents that are large hydrophilic molecules, such as polypeptides (including proteins and peptides), nucleic acids (including DNA and RNA), polysaccharides (including heparin), as well as particles, such as viral particles, and cells. In one aspect, the bioactive agent has a molecular weight of about 10,000 or greater.

Classes of bioactive agents which can be incorporated into biodegradable coatings (both the natural biodegradable matrix and/or the biodegradable microparticles) of this invention include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, opioids, photodynamic therapy agents, prostaglandins, remodeling inhibitors, statins, steroids, thrombolytic agents, tranquilizers, vasodilators, and vasospasm inhibitors.

Antibiotics are art recognized and are substances which inhibit the growth of or kill microorganisms. Examples of antibiotics include penicillin, tetracycline, chloramphenicol, minocycline, doxycycline, vancomycin, bacitracin, kanamycin, neomycin, gentamycin, erythromycin, cephalosporins, geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigrnine, neostigmine bromide, physostigmine sulfate, tacrine HCl, tacrine, 1-hydroxy-maleate, iodotubercidin, p-bromotetramisole, 10-α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−) alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rousvastatin, and superstatin.

Imaging agents are agents capable of imaging a desired site, e.g., tumor, in vivo, can also be included in the coating composition. Examples of imaging agents include substances having a label which is detectable in vivo, e.g., antibodies attached to fluorescent labels. The term antibody includes whole antibodies or fragments thereof.

Exemplary ligands or receptors include antibodies, antigens, avidin, streptavidin, biotin, heparin, type IV collagen, protein A, and protein G.

Exemplary antibiotics include antibiotic peptides.

In some aspects the bioactive agent can be selected to improve the compatibility (for example, with blood and/or surrounding tissues) of medical device surfaces. These agents, referred to herein as "biocompatible agents," when associated with the medical device surface, can serve to shield the blood from the underlying medical device material. Suitable biocompatible agents preferably reduce the likelihood for blood components to adhere to the medical device, thus reducing the formation of thrombus or emboli (blood clots that release and travel downstream).

The bioactive agent can improve the biocompatibility of the medical article having a coating that includes the natural biodegradable polymer and the biodegradable microparticle. The bioactive agent can provide antirestenotic effects, such as antiproliferative, anti-platelet, and/or antithrombotic effects. In some embodiments, the bioactive agent can include anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-ph-pr-arg-chloromethylketone (synthetic antithrombin), dipyridamole, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, everolimus, mycophenolic acid, sirolimus, tacrolimus, and the like.

Other exemplary therapeutic antibodies include trastuzumab (Herceptin™), a humanized anti-HER2 monoclonal antibody (moAb); alemtuzumab (Campath™), a humanized anti-CD52 moAb; gemtuzumab (Mylotarg™), a humanized anti-CD33 moAb; rituximab (Rituxan™), a chimeric anti-CD20 moAb; ibritumomab (Zevalim™), a murine moAb conjugated to a beta-emitting radioisotope; tositumomab (Bexxar™), a murine anti-CD20 moAb; edrecolomab (Panorex™), a murine anti-epithelial cell adhesion molecule moAb; cetuximab (Erbitux™), a chimeric anti-EGFR moAb; and bevacizumab (Avastin™), a humanized anti-VEGF moAb.

Additionally, the bioactive agent can be a surface adhesion molecule or cell-cell adhesion molecule. Exemplary cell adhesion molecules or attachment proteins (such as extracellular matrix proteins including fibronectin, laminin, collagen, elastin, vitronectin, tenascin, fibrinogen, thrombospondin, osteopontin, von Willibrand Factor, bone sialoprotein (and active domains thereof), or a hydrophilic polymer such as hyaluronic acid, chitosan or methyl cellulose, and other proteins, carbohydrates, and fatty acids. Exemplary cell-cell adhesion molecules include N-cadherin and P-cadherin and active domains thereof.

Exemplary growth factors include fibroblastic growth factors, epidermal growth factor, platelet-derived growth factors, transforming growth factors, vascular endothelial growth factor, bone morphogenic proteins and other bone growth factors, and neural growth factors.

The bioactive agent can be also be selected from mono-2-(carboxymethyl) hexadecanamidopoly (ethylene glycol)$_{200}$ mono-4-benzoylbenzyl ether, mono-3-carboxyheptadecanamidopoly (ethylene glycol)$_{200}$ mono-4-benzoylbenzyl ether, mono-2-(carboxymethyl)hexadecanamidotetra (ethylene glycol)mono-4-benzoylbenzyl ether, mono-3-carboxyheptadecanamidotetra (ethylene glycol)mono-4-benzoylbenzyl ether, N-[2-(4-benzoylbenzyloxy)ethyl]-2-(carboxymethyl) hexadecanamide, N-[2-(4-benzoylbenzyloxy)ethyl]-3-carboxyheptadecanamide, N-[12-(benzoylbenzyloxy)dodecyl]-2-(carboxymethyl)hexadecanamide, N-[12-(benzoylbenzyloxy)dodecyl]-3-carboxy-heptadecanamide, N-[3-(4-benzoylbenzamido)propyl]-2-(carboxymethyl) hexadecanamide, N-[3-(4-benzoylbenzamido)propyl]-3-carboxyheptadecanamide, N-(3-benzoylphenyl)-2-(carboxymethyl)hexadecanamide, N-(3-benzoylphenyl)-3-carboxyheptadecanamide, N-(4-benzoylphenyl)-2-(carboxymethyl)hexadecanamide, poly(ethylene glycol)$_{200}$ mono-15-carboxypentadecyl mono-4-benzoylbenzyl ether, and mono-15-carboxypentadecanamidopoly (ethylene glycol)$_{200}$ mono-4-benzoylbenzyl ether.

Additional examples of contemplated bioactive agents and/or bioactive agent include analogues of rapamycin ("rapalogs"), ABT-578 from Abbott, dexamethasone, betamethasone, vinblastine, vincristine, vinorelbine, poside, teniposide, daunorubicin, doxorubicin, idarubicin, anthracyclines, mitoxantrone, bleomycins, plicamycin (mithramycin), mitomycin, mechlorethamine, cyclophosphamide and its analogs, melphalan, chlorambucil, ethylenimines and methylmelamines, alkyl sulfonates-busulfan, nitrosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, estrogen, ticlopidine, clopidogrel, abciximab, breveldin, cortisol, cortisone, fludrocortisone, prednisone, prednisolone, 6U-methylprednisolone, triamcinolone, acetaminophen, etodalac, tolmetin, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, azathioprine, mycophenolate mofetil; angiotensin receptor blockers; nitric oxide donors; and mTOR inhibitors.

Viral particles and viruses include those that may be therapeutically useful, such as those used for gene therapy, and also attenuated viral particles and viruses which can promote an immune response and generation of immunity. Useful viral particles include both natural and synthetic types. Viral particles include, but are not limited to, adenoviruses, baculoviruses, parvoviruses, herpesviruses, poxviruses, adeno-associated viruses, vaccinia viruses, and retroviruses.

Other bioactive agents that can be used for altering gene function include plasmids, phages, cosmids, episomes, and integratable DNA fragments, antisense oligonucleotides, antisense DNA and RNA, modified DNA and RNA, iRNA, ribozymes, siRNA, and shRNA.

Other bioactive agents include cells such as platelets, stem cells, T lymphocytes, B lymphocytes, acidophils, adipocytes, astrocytes, basophils, hepatocytes, neurons, cardiac muscle cells, chondrocytes, epithelial cells, dendrites, endrocrine cells, endothelial cells, eosinophils, erythrocytes, fibroblasts, follicular cells, ganglion cells, hepatocytes, endothelial cells, Leydig cells, parenchymal cells, lymphocytes, lysozyme-secreting cells, macrophages, mast cells, megakaryocytes, melanocytes, monocytes, myoid cells, neck nerve cells, neutrophils, oligodendrocytes, oocytes, osteoblasts, osteochondroclasts, osteoclasts, osteocytes, plasma cells, spermatocytes, reticulocytes, Schwann cells, Sertoli cells, skeletal muscle cells, and smooth muscle cells. Bioactive agents can also include genetically modified, recombinant, hybrid, mutated cells, and cells with other alterations.

Additives such as inorganic salts, BSA (bovine serum albumin), and inert organic compounds can be used to alter the profile of bioactive agent release, as known to those skilled in the art.

The concentration of the bioactive agent or agents dissolved or suspended in the coating mixture can range from about 0.01 to about 90 percent, by weight, based on the weight of the final coated composition.

The particular bioactive agent, or combination of bioactive agents, can be selected depending upon one or more of the following factors: the application of the controlled delivery device, the medical condition to be treated, the anticipated duration of treatment, characteristics of the implantation site, the number and type of bioactive agents to be utilized, and the like.

Any of the polymer compositions described herein can be provided to the surface of the medical article and can include any number of desired bioactive agents, depending upon the final application of the medical device.

A comprehensive listing of bioactive agents can be found in *The Merck Index*, Thirteenth Edition, Merck & Co. (2001). Bioactive agents are commercially available from Sigma Aldrich Fine Chemicals, Milwaukee, Wis.

In some aspects of the invention, the bioactive agent can be used to promote thrombosis in association with the natural biodegradable polysaccharide-based coating, which can be of particular use when a coating having a sealant function is desired. A sealant coating including a thrombogenic agent can promote the in-growth of tissue upon degradation of the sealant coating material. The degree of thrombosis can be controlled by various factors, including, for example, the presence of one or more thrombosis-promoting bioactive agents on or within the coating. Suitable thrombotic agents are described herein.

In some aspects the thrombotic agent can be selected to have an affect on the blood and/or surrounding tissues that are in contact with the article surface. In some cases the thrombotic agent is chosen for the ability to affect the ability of blood components to adhere to the medical article. The thrombotic agent can, in some cases, be chosen to promote thrombus formation at the surface of the coated article. Therefore, in some embodiments, the sealant coating can include a thrombotic agent, such as thrombin, collagen (for example, (synthetic) recombinant human collagen (FibroGen, South San Francisco, Calif.)), ADP, or convulxin to promote thrombosis at the coated surface of the article.

Other prothrombotic or procoagulant factors include platelet factors 1-4, platelet activating factor (acetyl glyceryl ether phosphoryl choline); P-selectin and von Willebrand Factor (vWF); tissue factor; plasminogen activator initiator-1; thromboxane; procoagulant thrombin-like enzymes including cerastotin and afaacytin; phospholipase $A_2$; $Ca^{2+}$-dependent lectins (C-type lectin); factors that bind glycoprotein receptors and induce aggregation including aggretin, rhodocytin, aggregoserpentin, triwaglerin, and equinatoxin; glycoprotein Ib agonists including mamushigin and alboaggregin; vWF interacting factors including botrocetin, bitiscetin, cerastotin, and ecarin.

Other factors, including protein factors, that are involved in the clotting cascade include coagulation factors I-XIII (for example, fibrinogen, prothrombin, tissue thromboplastin, calcium, proaccelerin (accelerator globulin), proconvertin (serum prothrombin conversion accelerator), antihemophilic factor, plasma thromboplastin component, Stuart factor (autoprothrombin C), plasma thromboplastin antecedent (PTA), Hageman factor, and fibrin-stabilizing factor (FSF, fibrinase, protransglutaminase)).

Some surface adhesion molecule or cell-cell adhesion molecules may also function to promote coagulation or thrombosis. Exemplary cell adhesion molecules or attachment proteins (such as extracellular matrix proteins) include fibronectin, laminin, collagen, elastin, vitronectin, tenascin, fibrinogen, thrombospondin, osteopontin, von Willebrand Factor, bone sialoprotein (and active domains thereof), or a hydrophilic polymer such as hyaluronic acid, chitosan or methyl cellulose, and other proteins, carbohydrates, and fatty acids. Exemplary cell-cell adhesion molecules include N-cadherin and P-cadherin and active domains thereof.

The particular thrombotic agent, or a combination of thrombotic agents with other bioactive agents, can be selected depending upon one or more of the following factors: the application of the medical article, the medical condition to be treated, the anticipated duration of treatment, characteristics of the implantation site, the number and type of thrombogenic/bioactive agents to be utilized, the chemical composition of the sealant coating (such as amylose, selected additives, and the like), the extent of coupling in the formed sealant coating, and the like.

Any of the sealant compositions described herein can be provided to the surface of the medical article. In some embodiments the sealant coating can include any number of desired thrombogenic/bioactive agents, depending upon the final application of the medical article. The coating of sealant material (with or without thrombogenic/bioactive agents) can be applied to the medical article using standard techniques to cover the entire surface of the article, or a portion of the article surface. Further, the sealant composition material can be provided as a single coated layer (with or without thrombogenic/bioactive agents), or as multiple coated layers (with or without thrombogenic/bioactive agents). When multiple coated layers are provided on the surface, the materials of each coated layer can be chosen to provide a desired effect.

In some aspects of the invention, a microparticle is used to deliver the bioactive agent from the natural biodegradable polysaccharide-based coating. The microparticles of the invention can comprise any three-dimensional structure that can be immobilized on a substrate in association with the matrix formed by the amylose polymer. The term "microparticle" is intended to reflect that the three-dimensional structure is very small but not limited to a particular size range, or not limited to a structure that has a particular shape. According to the invention, microparticles typically have a size in the range of 5 nm to 100 μm in diameter. Generally microparticles are spherical or somewhat spherical in shape, but can have other shapes as well. In preferred embodiments of the invention, the biodegradable microparticles have a size in the range of 100 nm to 20 μm in diameter, and even more preferable in the range of 400 nm to 20 μm in diameter.

The microparticle being "biodegradable" refers to the presence of one or more biodegradable materials in the microparticle. The biodegradable microparticles include at least a biodegradable material (such as a biodegradable polymer) and a bioactive agent. The biodegradable microparticles can gradually decompose and release bioactive agent upon exposure to an aqueous environment, such as body fluids.

The biodegradable microparticle can also include one or more biodegradable polymers. Examples of biodegradable polymers that can be included in the biodegradable microparticle include, for example, polylactic acid, poly(lactide-co-glycolide), polycaprolactone, polyphosphazine, polymethylidenemalonate, polyorthoesters, polyhydroxybutyrate, polyalkeneanhydrides, polypeptides, polyanhydrides, and polyesters, and the like.

Biodegradable polyetherester copolymers can be used. Generally speaking, the polyetherester copolymers are amphiphilic block copolymers that include hydrophilic (for example, a polyalkylene glycol, such as polyethylene glycol) and hydrophobic blocks (for example, polyethylene terephthalate). Examples of block copolymers include poly(ethylene glycol)-based and poly(butylene terephthalate)-based blocks (PEG/PBT polymer). Examples of these types of multiblock copolymers are described in, for example, U.S. Pat. No. 5,980,948. PEG/PBT polymers are commercially available from Octoplus BV, under the trade designation PolyActive™.

Biodegradable copolymers having a biodegradable, segmented molecular architecture that includes at least two different ester linkages can also be used. The biodegradable polymers can be block copolymers (of the AB or ABA type) or segmented (also known as multiblock or random-block) copolymers of the $(AB)_n$ type. These copolymers are formed in a two (or more) stage ring opening copolymerization using two (or more) cyclic ester monomers that form linkages in the copolymer with greatly different susceptibilities to transesterification. Examples of these polymers are described in, for example, in U.S. Pat. No. 5,252,701 (Jarrett et al., "Segmented Absorbable Copolymer").

Other suitable biodegradable polymer materials include biodegradable terephthalate copolymers that include a phosphorus-containing linkage. Polymers having phosphoester linkages, called poly(phosphates), poly(phosphonates) and poly(phosphites), are known. See, for example, Penczek et al., Handbook of Polymer Synthesis, Chapter 17: "Phosphorus-Containing Polymers," 1077-1132 (Hans R. Kricheldorf ed., 1992), as well as U.S. Pat. Nos. 6,153,212, 6,485,737, 6,322,797, 6,600,010, 6,419,709. Biodegradable terephthalate polyesters can also be used that include a phosphoester linkage that is a phosphite. Suitable terephthalate polyester-polyphosphite copolymers are described, for example, in U.S. Pat. No. 6,419,709 (Mao et al., "Biodegradable Terephthalate Polyester-Poly(Phosphite) Compositions, Articles, and Methods of Using the Same). Biodegradable terephthalate polyester can also be used that include a phosphoester linkage that is a phosphonate. Suitable terephthalate polyester-poly(phosphonate) copolymers are described, for example, in U.S. Pat. Nos. 6,485,737 and 6,153,212 (Mao et al., "Biodegradable Terephthalate Polyester-Poly(Phosphonate) Compositions, Articles and Methods of Using the Same). Biodegradable terephthalate polyesters can be used that include a phosphoester linkage that is a phosphate. Suitable terephthalate polyester-poly(phosphate) copolymers are described, for example, in U.S. Pat. Nos. 6,322,797 and 6,600,010 (Mao et al., "Biodegradable Terephthalate Polyester-Poly(Phosphate) Polymers, Compositions, Articles, and Methods for Making and Using the Same).

Biodegradable polyhydric alcohol esters can also be used (See U.S. Pat. No. 6,592,895). This patent describes biodegradable star-shaped polymers that are made by esterifying polyhydric alcohols to provide acyl moieties originating from aliphatic homopolymer or copolymer polyesters. The biodegradable polymer can be a three-dimensional crosslinked polymer network containing hydrophobic and hydrophilic components which forms a hydrogel with a crosslinked polymer structure, such as that described in U.S. Pat. No. 6,583,219. The hydrophobic component is a hydrophobic macromer with unsaturated group terminated ends, and the hydrophilic polymer is a polysaccharide containing hydroxy groups that are reacted with unsaturated group introducing compounds. The components are convertible into a one-phase crosslinked polymer network structure by free radical polymerization. In yet further embodiments, the biodegradable polymer can comprise a polymer based upon α-amino acids (such as elastomeric copolyester amides or copolyester urethanes, as described in U.S. Pat. No. 6,503,538).

The biodegradable microparticle can include one or more biodegradable polymers obtained from natural sources. In some preferred aspects the biodegradable polymer is selected from hyaluronic acid, dextran, starch, amylose, amylopectin, cellulose, xanthan, pullulan, chitosan, pectin, inulin, alginates, and heparin. One, or combinations of more than one of these biodegradable polymers, can be used. A particular biodegradable polymer can also be selected based on the type of bioactive agent that is present in the microparticle. Therefore, in some aspects of the invention, the biodegradable coating can include a natural biodegradable polysaccharide matrix and a natural biodegradable polysaccharide-containing microparticle.

Therefore, in some embodiments, the microparticles include a natural biodegradable polysaccharide such as amylose or maltodextrin. In some embodiments the natural biodegradable polysaccharide can be the primary biodegradable component in the microparticle. In some embodiments, both the coating matrix and the microparticle include amylose and/or maltodextrin as components.

Dextran-based microparticles can be particularly useful for the incorporation of bioactive agents such as proteins, peptides, and nucleic acids. Examples of the preparation of dextran-based microparticles are described in U.S. Pat. No. 6,303,148.

The preparation of amylose and other starch-based microparticles have been described in various references, including, for example, U.S. Pat. No. 4,713,249; U.S. Pat. No. 6,692,770; and U.S. Pat. No. 6,703,048. Biodegradable polymers and their synthesis have been also been described in various references including Mayer, J. M., and Kaplan, D. L. (1994) Trends in Polymer Science 2:pages 227-235; and Jagur-Grodzinski, J., (1999) Reactive and Functional Polymers: Biomedical Application of Functional Polymers, Vol. 39, pages 99-138.

In some aspects of the invention, the biodegradable microparticle contains a biologically active agent (a "bioactive agent"), such as a pharmaceutical or a prodrug. Microparticles can be prepared incorporating various bioactive agents by established techniques, for example, by solvent evaporation (see, for example, Wichert, B. and Rohdewald, P. J Microencapsul. (1993) 10:195). The bioactive agent can be released from the biodegradable microparticle (the microparticle being present in the natural biodegradable polysaccharide coating) upon degradation of the biodegradable microparticle in vivo. Microparticles having bioactive agent can be formulated to release a desired amount of the agent over a predetermined period of time. It is understood that factors affecting the release of the bioactive agent and the amount released can be altered by the size of the microparticle, the amount of bioactive agent incorporated into the microparticle, the type of degradable material used in fabricating the microparticle, the amount of biodegradable microparticles immobilized per unit area on the substrate, etc.

The microparticles can also be treated with a porogen, such as salt, sucrose, PEG, or an alcohol, to create pores of a desired size for incorporation of the bioactive agent.

The quantity of bioactive agents provided in the biodegradable microparticle can be adjusted by the user to achieve the desired effect. For example, a particular amount of anti-coagulant drug can be incorporated into the microparticle to provide a certain level of anti-coagulant activity from the biodegradable coating. Biologically active compounds can be provided by the microparticles in a range suitable for the application. In another example, protein molecules can be provided by biodegradable microparticles. For example, the amount of protein molecules present can be in the range of 1-250,000 molecules per 1 µm diameter microparticle.

Generally, the concentration of the bioactive agent present in the biodegradable microparticles can be chosen based on any one or a combination of a number of factors, including, but not limited to, the release rate from the coating, the type of bioactive agent(s) in the coating, the desired local or systemic concentration of the bioactive agent following release, and the half life of the bioactive agent. In some cases the concentration of bioactive agent in the microparticle can be about 0.001% or greater, or in the range of about 0.001% to about 50 percent, or greater, by weight, based on the weight of the microparticle.

The particular bioactive agent to be included in the biodegradable microparticle, or combination of bioactive agents in microparticles, can be selected depending upon factors such as the application of the coated device, the medical condition to be treated, the anticipated duration of treatment, characteristics of the implantation site, the number and type of bioactive agents to be utilized, the chemical composition of the microparticle, size of the microparticle, crosslinking, and the like.

In one embodiment, the invention advantageously allows for preparation of surfaces having two, or more than two, different bioactive agents, wherein the bioactive agents are mutually incompatible in a particular environment, for example, as hydrophobic and hydrophilic drugs are incompatible in either a polar or non-polar solvent. Different bioactive agents may also demonstrate incompatibility based on protic/aprotic solvents or ionic/non-ionic solvents. For example, the invention allows for the preparation of one set of biodegradable microparticles containing a hydrophobic drug and the preparation of another set of biodegradable microparticles containing a hydrophilic drug; the mixing of the two different sets of microparticles into a polymeric material used to form the matrix; and the disposing of the mixture on the surface of a substrate. Both hydrophobic and hydrophilic drugs can be released from the surface of the coated substrate at the same time as the biodegradable microparticles degrade, or the composition of the biodegradable microparticles or the natural biodegradable polysaccharide matrix can be altered so that one bioactive agent is released at a different rate or time than the other one.

Biodegradable microparticles can be prepared having compositions that are suitable for either hydrophobic or hydrophilic drugs. For example, polymers such as polylactide or polycaprolactone can be useful for preparing biodegradable microparticles that include hydrophobic drugs; whereas polymers such as amylose or glycolide can be useful for preparing microparticles that include hydrophilic drugs.

Traditional coating procedures directed at disposing at least two different types of bioactive agents have often required that the bioactive agents be put down separately. Traditional approaches may include the steps of solubilizing a hydrophobic drug in a non-polar solvent, coating the surface of the substrate with the non-polar mixture, drying the non-polar mixture, solubilizing the hydrophilic drug in a polar solvent, coating the layer of the dried non-polar mixture with the polar mixture, and then drying the polar mixture. This type of traditional coating process can be inefficient and can also result in undesirable surface properties (e.g., the layering of the drugs will cause one drug to be released before the other one is released). According to this aspect of the invention, the method of preparing surfaces having two, or more than two, different bioactive agents, in particular when the two different bioactive agents are released from the surface of the substrate, is a significant improvement over traditional methods of coating substrates and delivering bioactive agents from the surface of the substrates.

Components of the biodegradable coating can be applied to the medical device using standard techniques to cover the entire surface of the device, or a portion of the device surface. As indicated, the components can be applied to the medical device independently or together, for example, in a composition. The coating formed on the device can be a single layer coating, or a multiple layer coating.

Various factors can influence the delivery of bioactive agents from the coating. These include the concentration of the natural biodegradable polysaccharide and the extent of natural biodegradable polysaccharide coupling in the coating, the amount and location of biodegradable microparticles associated with the coating, the concentration of bioactive agent in the microparticles, and the presence of other coated layers, if included in the overall coating and the like. For example, the rate of delivery of the drug can be decreased by increasing the concentration of polymeric material or the relative amount of coupling or crosslinking of the polymeric material in the polymeric matrix or in the microparticle. Based on the description provided herein and the general knowledge in this technical area, one can alter properties of the coating to provide a desired release rate for one or more particular bioactive agents from the coating.

Portions of the coating can be prepared to degrade at the same or different rates. For example, the biodegradable microparticles can be prepared or obtained to have a faster rate of degradation than the natural biodegradable polysaccharide matrix. In this case, the bioactive agent can be released into the natural biodegradable polysaccharide matrix and/or diffuse out of the natural biodegradable polysaccharide matrix.

A natural biodegradable polysaccharide-based coating can be prepared by any one of a variety of methods. A "coating" as used herein can include one or more "coated layers", each coated layer including one or more coating materials. In many cases, the coating consists of a single layer of material that includes the natural biodegradable polysaccharide, such as amylose or maltodextrin. In other cases, the coating includes more than one coated layer, at least one of the coated layers including the natural biodegradable polysaccharide. If more than one layer is present in the coating, the layers can be composed of the same or different materials. If multiple polymeric layers are provided on the surface, each individual layer of polymer can be chosen to provide a desired effect. Additionally, multiple layers of various bioactive agents can be deposited onto the medical device surface so that a particular bioactive agent can be presented to or released from the medical device at one time, one or more bioactive agents in each layer, which can be separated by polymeric material.

If more than one coated layer is applied to a surface, it is typically applied successively. For example, a natural biodegradable polysaccharide coated layer can be formed by, for example, dipping, spraying, bushing, or swabbing the coating material on the article to form a layer, and then drying the coated layer. The process can be repeated to provide a coating having multiple coated layers, wherein at least one layer includes the natural biodegradable polysaccharide.

Thus, in some embodiments wherein multiple coated layers are prepared, each coated layer is composed of the same materials. Alternatively, one or more of the coated layers is composed of materials that are different from one or more of the other layers. Additionally, multiple layers of various bioactive agents can be deposited onto the medical article surface so that a particular bioactive agent can be presented to or released from the medical article at one time, one or more bioactive agents in each layer, which can be separated by polymeric material.

The invention also provides the advantage of maintaining excellent control over the formation of a coating on the surface of an article. To exemplify this aspect of the invention, an initiator is disposed on a surface of a medical article along with the natural biodegradable polysaccharide having pendent coupling groups. A bioactive agent can be disposed if desired. The initiator can be disposed in a mixture with the natural biodegradable polysaccharide together, or the initiator can be disposed independently. These compounds are generally disposed in a fluid state (for example, suspended or dissolved in an aqueous liquid) and can be disposed on an article surface using any one of number of techniques as described herein. After the initiator and natural biodegradable polysaccharide are both disposed, the initiator is activated, resulting in the activation of the pendent coupling groups, the coupling of natural biodegradable polysaccharide molecules, and the formation of the coating. The steps of disposing and activating can be performed in ways (as described herein and/or known in the art) to precisely control the formation of a coating. For example, the thickness and the location of the coating on the article surface can be controlled using techniques described herein and/or known in the art.

In preferred aspects of the following methods, the natural biodegradable polysaccharide is selected from the group of amylose and maltodextrin. In other preferred aspects of the following methods, the natural biodegradable polysaccharide has a molecular weight of 500,000 Da or less, 250,000 Da or less, 100,000 Da or less, or 50,000 Da or less. It is also preferred that the natural biodegradable polysaccharides have an average molecular weight of 500 Da or greater. A particularly preferred size range for the natural biodegradable polysaccharides is in the range of about 1000 Da to about 10,000 Da.

For example, in some aspects the method includes the steps of (i) disposing a composition comprising (a) a natural biodegradable polysaccharide having a coupling group, (b) an initiator, and (c) a bioactive agent on a surface; and (ii) activating the initiator to provide a coated composition having the natural biodegradable polysaccharide and the bioactive agent on the surface. This method can also be used to form a medical implant wherein the composition is disposed to form an implant of a desired configuration. For example, the composition can be disposed in a mold. This method can also be used to form an in situ formed matrix wherein the composition is disposed within a portion of a subject.

In other aspects, the method includes the steps of (i) disposing an initiator on a surface, (ii) disposing a composition comprising (a) a natural biodegradable polysaccharide having a coupling group and (b) a bioactive agent on the surface; and (iii) activating the initiator to provide a coated composition having the natural biodegradable polysaccharide and the bioactive agent.

During the step of activating, a composition including the natural biodegradable polysaccharide and the bioactive agent are contacted with the initiator and the initiator is activated to promote the crosslinking of two or more natural biodegradable polysaccharides via their coupling groups. In preferred aspects the natural biodegradable polysaccharide includes a polymerizable group, such as an ethylenically unsaturated group, and initiator is capable of initiating free radical polymerization of the polymerizable groups. Therefore, in another embodiment, the invention provides a method for coating a surface, including the steps of (i) disposing a composition comprising (a) a natural biodegradable polysaccharide having a ethylenically unsaturated group, (b) a polymerization initiator, and (c) a bioactive agent on a surface; and (ii) activating the polymerization initiator to cause the polymerization of the amylose compound thereby providing a coated composition having the natural biodegradable polysaccharide and the bioactive agent on the surface. These methods can also be used to form medical implants and in situ-formed matrices, wherein the composition is disposed in a mold or in a subject, respectively, rather than on a surface.

In yet another aspect the invention provides a medical device having a coated composition comprising a plurality of coupled natural biodegradable polysaccharide and a bioactive agent.

In some embodiments, the invention provides methods for preparing biodegradable coatings that include (a) a natural biodegradable polysaccharide having a coupling group and (b) biodegradable microparticles having a bioactive agent.

In some embodiments the coupling group can be activated by an initiator. Therefore, the method can include the steps of (i) disposing an initiator on a surface, (ii) disposing a composition comprising (a) a natural biodegradable polysaccharide having a coupling group and (b) biodegradable microparticles comprising a bioactive agent; and (iii) activating the initiator to provide a biodegradable bioactive agent-releasing coated composition having the natural biodegradable polysaccharide and the biodegradable microparticles having the bioactive agent.

In preferred aspects the natural biodegradable polysaccharide includes a polymerizable group, such as an ethylenically unsaturated group, and initiator is capable of initiating free radical polymerization of the polymerizable groups. Therefore, in another embodiment, the invention provides a method for coating a surface, including the steps of (i) disposing a composition comprising (a) a natural biodegradable polysaccharide having an ethylenically unsaturated group, (b) a polymerization initiator, and (c) biodegradable microparticles having a bioactive agent on a surface; and (ii) activating the polymerization initiator to cause the polymerization of the natural biodegradable polysaccharide thereby providing a coated composition that includes biodegradable microparticles in a natural biodegradable polysaccharide matrix. The invention also provides alternative methods for preparing a coated surface that is biodegradable and having microparticles that can release a bioactive agent. The methods include disposing in two or more steps at least the following reagents on a surface: (a) a natural biodegradable polysaccharide comprising a first coupling group (b) a natural biodegradable polysaccharide comprising a second coupling group that is reactive with the first coupling group, and (c) biodegradable microparticles that include a bioactive agent. According to this method reagents (a) and (b) are reactive with each other and are disposed separately on the surface but can individually include (c). For example, reagent (a) is first disposed on the surface and then a mixture comprising reagent (b) and (c) is then disposed on reagent (a). Reagent (a) reacts with (b) to link the natural biodegradable polysaccharide together to form a coating that includes (c), the biodegradable microparticles.

The invention also provides methods for preparing biodegradable sealant coatings that include a natural biodegradable polysaccharide having a coupling group; optionally a bioactive agent can be included in the sealant coating.

In some embodiments, the method includes the steps of (i) disposing a sealant composition comprising (a) a natural biodegradable polysaccharide having a coupling group, and (b) an initiator, and (ii) activating the initiator to form a sealant coating. This aspect of the invention includes coating methods where a bulk polymerization approach is performed. For example, in some embodiments, a composition including a polymerization initiator and natural biodegradable polysaccharides having a polymerizable group is disposed on a surface. The initiator is then activated to promote bulk polymerization and coupling of the natural biodegradable polysaccharides in association with the surface.

In other aspects, the method includes the steps of (i) disposing an initiator on a surface, (ii) disposing a natural biodegradable polysaccharide having a coupling group; and (iii) activating the initiator to provide a coated composition having the amylose polymer. The natural biodegradable polysaccharides can be disposed on the surface along with other reagents if desired. This aspect of the invention includes coating methods where a graft polymerization approach is performed. For example, in some embodiments, a polymerization initiator is first disposed on a surface and then a natural biodegradable polysaccharide having a polymerizable group is disposed on the surface having the initiator. The initiator is activated to promote free radical polymerization, and coupling of the natural biodegradable polysaccharides from the surface. In other embodiments of the invention, an aqueous composition that includes the natural biodegradable polysaccharide having the coupling group and a bioactive agent is obtained and used in the method of providing a sealant coating to a surface. This composition can be prepared by mixing the natural biodegradable polysaccharide with a bioactive agent, for example, a water-soluble small molecule, a protein, or a nucleic acid. In one preferred aspect of the invention, the bioactive agent is a procoagulant or prothrombotic factor. For example, the bioactive agent can be a protein such as recombinant collagen, or other proteins that associate with receptors on platelets to induce platelet aggregation.

In some aspects of the invention, the coating is placed in contact with an aqueous solution, or the materials of the coating composition. The coating or coating materials are designed to be stable in the presence of the aqueous solution provided that an enzyme that causes the degradation of the natural biodegradable polysaccharide (or another degrading agent) is not present in an amount sufficient to cause substantial degradation of the materials.

For example, the invention provides a shelf stable composition comprising a natural biodegradable polysaccharide comprising coupling groups. These compositions could be obtained or prepared, according to the details provided herein, and then stored for a period of time before the composition is used to form a biodegradable coating, without the significant degradation of the natural biodegradable polysaccharide occurring during storage.

Accordingly, the invention also provides methods for preparing a biodegradable coating comprising preparing a biodegradable coating composition comprising a natural biodegradable polysaccharide comprising coupling group; storing the coating composition for an amount of time; and then using the coating composition to prepare a biodegradable coating. Optionally, one or more bioactive agents and/or microparticles can be added before or after storage of the coating composition.

In a related aspect, the invention also provides the advantage of being able to perform synthetic and post-synthetic procedures wherein the natural biodegradable polysaccharide is contacted with an aqueous composition, and there is minimal risk of degradation of the polysaccharide. For example, the natural biodegradable polysaccharide may be contacted with an aqueous solution for purification without risking significant degradation of the natural biodegradable polysaccharide.

In yet another aspect, the invention relates to the stability of the coatings that are formed on an article. The invention provides a method comprising obtaining an article having a coating comprising a natural biodegradable polysaccharide, and then contacting the article with an aqueous solution. The aqueous solution can be, for example, a storage solution, a solution that is used to hydrate the surface of the coated device, or an aqueous sterilization solution.

In some aspects the coating can be contacted with an aqueous sterilization solution. Medical articles, or parts of medical articles, can be prepared having a coating and these articles can be treated to sterilize one or more parts of the article, or the entire medical article. Sterilization can take place prior to using the medical article and/or, in some cases, during implantation of the medical article.

In some aspects, the invention provides a method for delivering a bioactive agent from a biodegradable coating or a biodegradable article by exposing the coating or article to an enzyme that causes the degradation of the coating. In performing this method a coated article, such as an implantable medical device is provided to a subject. The coated article has a biodegradable coating comprising a natural biodegradable polysaccharide having pendent coupling groups, wherein the coating is formed on a surface of the article by reaction of the coupling groups to form a crosslinked matrix of a plurality of natural biodegradable polysaccharides, and wherein the coating includes a bioactive agent. The coating or article is then exposed to a carbohydrase that can promote the degradation of the biodegradable coating.

The carbohydrase that contacts the coating or article can specifically degrade the natural biodegradable polysaccharide causing release of the bioactive agent. Examples of carbohydrases that can specifically degrade natural biodegradable polysaccharide coatings include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 Upper liter, and vitreal concentrations also fall within this range (Varela, R. A., and Bossart, G. D. (2005) *J Am Vet Med Assoc* 226:88-92).

In some aspects, the carbohydrase can be administered to a subject to increase the local concentration, for example in the serum or the tissue surrounding the implanted device, so that the carbohydrase may promote the degradation of the coating. Exemplary routes for introducing a carbohydrase include local injection, intravenous (IV) routes, and the like. Alternatively, degradation can be promoted by indirectly increasing the concentration of a carbohydrase in the vicinity of the coated article, for example, by a dietary process, or by ingesting or administering a compound that increases the systemic levels of a carbohydrase.

In other cases, the carbohydrase can be provided on a portion of the coated article. For example the carbohydrase may be eluted from a portion of the article that does not have the natural biodegradable polymer coating. In this aspect, as the carbohydrase is released it locally acts upon the coating to cause its degradation and promote the release of the bioactive agent. Alternatively, the carbohydrase can be present in a microparticle in one or more portions the coating. As the carbohydrase is released from the microparticle, it causes coating degradation and promote the release of the bioactive agent.

In another aspect, the invention sets forth methods for providing lubricity to an article surface. The matrix of biodegradable polysaccharides as described herein can provide a surprisingly lubricious and durable surface when formed, for example, on the surface of a device.

As used herein, the term "lubricity" refers to a characterization of the frictional force associated with a coating. A lubricious coating can reduce the frictional forces present on the surface of the device when another surface is moved against the device surface. For example, a catheter having a coating that provides improved lubricity will encounter less frictional resistance when moved within a portion of the body, as compared to an uncoated substrate, or a coating that is not lubricious. Lubricity can also be important for devices with inner moving parts in addition to devices that function along with another device, for example, a coronary catheter which guides the insertion of a PTCA catheter. The methods can be used to prepare lubricious coatings for short term use and/or single use devices.

Improved lubricity can be shown by one or more methods. One method of testing lubricity of a coating is by the horizontal sled style friction test method (such as ASTM D-1894; a modified test is described herein). The lubricity measurements described herein refer to the kinetic coefficient of friction, which is equal to the average force reading obtained during uniform sliding of the surfaces divided by the sled weight. The measurements are in grams.

As shown herein, the biodegradable polysaccharide coatings generally show a lubricity of 20 g or less, and coatings having a lubricity of 15 g or less, or 10 g or less can be prepared by the methods described herein. In one desirable method for preparing the coating, a biodegradable polysaccharide matrix is formed using a photoinitiator to promote association of the biodegradable polysaccharides and matrix formation.

Another method which can be used to demonstrate an improvement in lubricity is the water contact angle measurement method. Reduction of water contact angle is indicative of increased wettability, which associates with an improvement in lubricity.

Also, in many aspects, the biodegradable coating of the invention demonstrates excellent durability. As used herein, the term "durability" refers to the wear resistance of the biodegradable polysaccharide coating. A more durable coating is less easily removed from a substrate by abrasion. Durability of a coating can be assessed by subjecting the device to conditions that simulate use conditions. The durability of the coating compositions is demonstrated by the ability to adhere to the device surface sufficiently to withstand the effect of shear forces encountered during insertion and/or removal of the device, which could otherwise result in delamination of the coating from the body member.

Improved durability can be shown by one or more methods. One preferred method of testing durability, as well as lubricity, is by the horizontal sled style friction test method described herein. In the method multiple push-pull cycles are performed and friction measurements are taken during the measurements. If minimal increase in friction values is seen after multiple push pull cycles, the coating is though to have good durability.

The biodegradable coatings of the present invention showed excellent durability. For example, the lubricity of the fifth push and pull cycle generally was not greater than 10% or more typically not greater than 5% of the lubricity of the first push and pull cycle. At later points, for example, at the fortieth push and pull cycle, the lubricity generally was not greater than 20% or more typically not greater than 10% of the lubricity of the first push and pull cycle.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Example 1

Synthesis of Acrylated-Amylose

Amylose having polymerizable vinyl groups was prepared by mixing 0.75 g of amylose (A0512; Aldrich) with 100 mL of methylsulfoxide (JT Baker) in a 250 mL amber vial, with stirring. After one hour, 2 mL of triethylamine (TEA; Aldrich) was added and the mixture was allowed to stir for 5 minutes at room temperature. Subsequently, 2 mL of glycidyl acrylate (Polysciences) was added and the amylose and glycidyl acrylate were allowed to react by stirring overnight at room temperature. The mixture containing the amylose-glycidyl acrylate reaction product was dialyzed for 3 days against DI water using continuous flow dialysis. The resultant acrylated-amylose (0.50 g; 71.4% yield) was then lyophilized and stored desiccated at room temperature with protection from light.

Example 2

Synthesis of MTA-PAAm

A polymerization initiator was prepared by copolymerizing a methacrylamide having a photoreactive group with acrylamide.

A methacrylamide-oxothioxanthene monomer (N-[3-(7-Methyl-9-oxothioxanthene-3-carboxamido)propyl]methacrylamide (MTA-APMA)) was first prepared. N-(3-aminopropyl)methacrylamide hydrochloride (APMA), 4.53 g (25.4 mmol), prepared as described in U.S. Pat. No. 5,858,653, Example 2, was suspended in 100 mL of anhydrous chloroform in a 250 mL round bottom flask equipped with a drying tube. 7-methyl-9-oxothioxanthene-3-carboxylic acid (MTA) was prepared as described in U.S. Pat. No. 4,506,083, Example D. MTA-chloride (MTA-Cl) was made as described in U.S. Pat. No. 6,007,833, Example 1. After cooling the slurry in an ice bath, MTA-Cl (7.69 g; 26.6 mmol) was added as a solid with stirring to the APMA-chloroform suspension.

A solution of 7.42 mL (53.2 mmol) of TEA in 20 mL of chloroform was then added over a 1.5 hour time period, followed by a slow warming to room temperature. The mixture was allowed to stir 16 hours at room temperature under a drying tube. After this time, the reaction was washed with 0.1N HCl and the solvent was removed under vacuum after adding a small amount of phenothiazine as an inhibitor. The resulting product was recrystallized from tetrahydrofuran (THF)/toluene (3/1) and gave 8.87 g (88.7% yield) of product after air drying. The structure of MTA-APMA was confirmed by NMR analysis.

MTA-APMA was then copolymerized with acrylamide in DMSO in the presence of 2-mercaptoethanol (a chain transfer agent), N,N,N',N'-tetramethyl-ethylenediamine (a co-catalyst), and 2,2'-azobis(2-methyl-propionitrile) (a free radical initiator) at room temperature. The solution was sparged with nitrogen for 20 minutes, sealed tightly, and incubated at 55° C. for 20 hours. The solution was dialyzed for 3 days against DI water using continuous flow dialysis. The resultant MTA-PAAm was lyophilized, stored desiccated, and protected from light at room temperature.

Example 3

Formation of an Amylose Coating 100 mg of acrylated-amylose as prepared in Example 1 was placed in an 8 mL amber vial. To the acrylated-amylose was added 3 mg of MTA-PAAm (lyophilized), 2 µL of 2-NVP (N-vinyl-2-pyrrolidone; accelerant (Bimax)) and 1 mL of 1× phosphate-buffered saline (1×PBS). The reagents were then mixed for one hour on a shaker at 37° C. The mixture in an amount of 50 µL was placed onto a glass slide (2991FI; Esco) and illuminated for 50 seconds with an EFOS 100 SS illumination system equipped with a 400-500 nm filter (50 mW/cm$^2$). After illumination the polymer was found to form a semi-firm gel having elastomeric properties.

Example 4

Preparation of 4-bromomethylbenzophenone (BMBP)

4-Methylbenzophenone (750 g; 3.82 moles) was added to a 5 liter Morton flask equipped with an overhead stirrer and dissolved in 2850 mL of benzene. The solution was then heated to reflux, followed by the dropwise addition of 610 g (3.82 moles) of bromine in 330 mL of benzene. The addition rate was approximately 1.5 mL/min and the flask was illuminated with a 90 watt (90 joule/sec) halogen spotlight to initiate the reaction. A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired 4-bromomethylbenzophenone, 8% of the dibromo product, and 20% unreacted 4-methylbenzophenone. After cooling, the reaction mixture was washed with 10 g of sodium bisulfite in 100 mL of water, followed by washing with 3×200 mL of water. The product was dried over sodium sulfate and recrystallized twice from 1:3 toluene:hexane. After drying under vacuum, 635 g of 4-bromomethylbenzophenone was isolated, providing a yield of 60%, having a melting point of 112° C.-114° C. Nuclear magnetic resonance ("NMR") analysis ($^1$H NMR (CDCl$_3$)) was consistent with the desired product: aromatic protons 7.20-7.80 (m, 9H) and methylene protons 4.48 (s, 2H). All chemical shift values are in ppm downfield from a tetramethylsilane internal standard.

Example 5

Preparation of ethylenebis(4-benzoylbenzyldimethylammonium) dibromide

N,N,N',N'-Tetramethylethylenediamine (6 g; 51.7 mmol) was dissolved in 225 mL of chloroform with stirring. BMBP (29.15 g; 106.0 mmol), as described in Example 4, was added as a solid and the reaction mixture was stirred at room temperature for 72 hours. After this time, the resulting solid was isolated by filtration and the white solid was rinsed with cold chloroform. The residual solvent was removed under vacuum and 34.4 g of solid was isolated for a 99.7% yield, melting point 218° C.-220° C. Analysis on an NMR spectrometer was consistent with the desired product: $^1$H NMR (DMSO-d$_6$) aromatic protons 7.20-7.80 (m, 18H), benzylic methylenes 4.80 (br. s, 4H), amine methylenes 4.15 (br. s, 4H), and methyls 3.15 (br. s, 12H).

Example 6

Formation of an Amylose Matrix on Pet Mesh

Acrylated-amylose (100 mg), as described in Example 1, was placed in an 8 mL amber vial. Ethylenebis(4-benzoylbenzyldimethylammonium)dibromide (3 mg), as described in Example 5, 2 µl of 2-NVP, and 1 mL of 1× phosphate buffered saline (1×PBS) was added to the acrylated-amylose and mixed for two hours on a shaker at 37° C. The mixture (250 µl) was spread onto a 3 cm×2 cm polyethylene terephthalate (PET) mesh substrate (41 µm monofil diameter; Goodfellow Cambridge Ltd., UK). The PET substrate with the applied amylose mixture was placed in a Dymax Lightweld PC-2 illumination system (Dymax Corp.; light intensity 6.5 mW/cm$^2$), 15 cm from the light source, and illuminated for 60 seconds. After illumination, the applied amylose mixture was found to form a semi-firm gel on the PET substrate, with elastomeric properties evident.

Example 7

Preparation of 1-(6-oxo-6-hydroxyhexyl)maleimide (Mal-EACA)

A maleimide functional acid was prepared in the following manner, and was used in Example 8. EACA (6-aminocaproic acid), (100 g; 0.762 moles), was dissolved in 300 mL of acetic acid in a three-neck, three liter flask equipped with an overhead stirrer and drying tube. Maleic anhydride, (78.5 g; 0.801 moles), was dissolved in 200 mL of acetic acid and added to the EACA solution. The mixture was stirred one hour while heating on a boiling water bath, resulting in the formation of a white solid. After cooling overnight at room temperature, the solid was collected by filtration and rinsed two times with 50 mL of hexane each rinse. After drying, the yield of the (z)-4-oxo-5-aza-undec-2-endioic acid (Compound 1) was in the range of 158-165 g (90-95%) with a melting point of 160-165° C. Analysis on an NMR spectrometer was consistent with the desired product: $^1$H NMR (DMSO-d$_6$, 400 MHz) δ 6.41, 6.24 (d, 2H, J=12.6 Hz; vinyl protons), 3.6-3.2 (b, 1H; amide proton), 3.20-3.14 (m, 2H: methylene adjacent to nitrogen), 2.20 (t, 2H, J=7.3; methylene adjacent to carbonyl), 1.53-1.44 (m, 4H; methylenes adjacent to the central methylene), and 1.32-1.26 (m, 2H; the central methylene).

(z)-4-oxo-5-aza-undec-2-endioic acid, (160 g; 0.698 moles), zinc chloride, 280 g (2.05 moles), and phenothiazine, 0.15 g were added to a two liter round bottom flask fitted with an overhead stirrer, condenser, thermocouple, addition funnel, an inert gas inlet, and heating mantle. Chloroform ($CHCl_3$), 320 mL was added to the 2 liter reaction flask, and stirring of the mixture was started. Triethylamine (480 mL; 348 g, 3.44 moles (TEA)) was added over one hour. Chlorotrimethyl silane (600 mL; 510 g, 4.69 moles) was then added over two hours. The reaction was brought to reflux and was refluxed overnight (16 hours). The reaction was cooled and added to a mixture of $CHCl_3$ (500 mL), water (1.0 liters), ice (300 g), and 12 N hydrochloric acid (240 mL) in a 20 liter container over 15 minutes. After 15 minutes of stirring, the aqueous layer was tested to make sure the pH was less than 5. The organic layer was separated, and the aqueous layer was extracted three times with $CHCl_3$ (700 mL) each extraction. The organic layers were combined and evaporated on a rotary evaporator. The residue was then placed in a 20 liter container. A solution of sodium bicarbonate (192 g) in water (2.4 liters) was added to the residue. The bicarbonate solution was stirred until the solids were dissolved. The bicarbonate solution was treated with a solution of hydrochloric acid, (26 liters of 1.1 N) over 5 minutes to a pH of below 2. The acidified mixture was then extracted with two portions of $CHCl_3$, (1.2 liters and 0.8 liters) each extraction. The combined extracts were dried over sodium sulfate and evaporated. The residue was recrystallized from toluene and hexane. The crystalline product was then isolated by filtration and dried which produced 85.6 g of white N-(6-oxo-6-hydroxyhexyl)maleimide (Mal-EACA; Compound 2). Analysis on an NMR spectrometer was consistent with the desired product: $^1H$ NMR ($CDCl_3$, 400 MHz) δ 6.72 (s, 2H; maleimide protons), 3.52 (t, 2H, J=7.2 Hz; methylene next to maleimide), 2.35 (t, 2H, J=7.4; methylene next to carbonyl), 1.69-1.57 (m, 4H; methylenes adjacent to central methylene), and 1.39-1.30 (m, 2H; the central methylene). The product had a DSC (differential scanning calorimator) melting point peak at 89.9° C.,

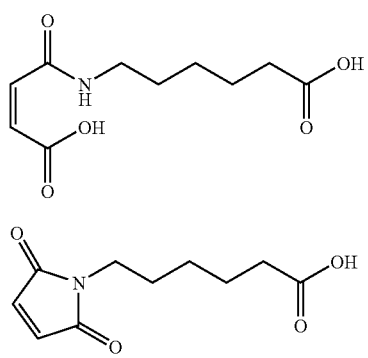

Compound 1

Compound 2

Example 8

Preparation of N-(5-isocyanatopentyl)maleimide (Mal-C5-NCO)

Mal-EACA from Example 7 (5.0 g; 23.5 mmole) and $CHCl_3$ (25 mL) were placed in a 100 mL round bottom flask and stirred using a magnetic bar with cooling in an ice bath. Oxalyl chloride (10.3 mL; ~15 g; 118 mmole) was added and the reaction was brought to room temperature with stirring overnight. The volatiles were removed on a rotary evaporator, and the residue was azetroped with three times with 10 mL $CHCl_3$ each time. The intermediate Mal-EAC-Cl [N-(6-oxo-6-chlorohexyl)maleimide] (Compound 3) was dissolved in acetone (10 mL) and added to a cold (ice bath) stirred solution of sodium azide (2.23 g; 34.3 mmole) in water (10 mL). The mixture was stirred one hour using an ice bath. The organic layer was set aside in an ice bath, and the aqueous layer was extracted three times with 10 mL $CHCl_3$. All operations of the acylazide were done at ice bath temperatures. The combined organic solutions of the azide reaction were dried for an hour over anhydrous sodium sulfate. The N-(6-oxo-6-azidohexyl) maleimide (Compound 4) solution was further dried by gentle swirling over molecular sieves over night. The cold azide solution was filtered and added to refluxing $CHCl_3$, 5 mL over a 10 minute period. The azide solution was refluxed for 2 hours. The weight of Mal-C5-NCO (Compound 5) solution obtained was 55.5 g, which was protected from moisture. A sample of the isocyanate solution, 136 mg was evaporated and treated with DBB (1,4-dibromobenzene), 7.54 mg and chloroform-d, 0.9 mL: $^1H$ NMR ($CDCl_3$, 400 MHz) δ 6.72 (s, 2H), 3.55 (t, 2H, J=7.2 Hz), 3.32 (t, 2H, J=6.6 Hz), 1.70-1.59 (m, 4H), 1.44-1.35 (m, 2H). The NMR spectra was consistent with desired product. The DBB internal standard 8 at 7.38 (integral value was 2.0, 4H; per mole of product) was used to estimate the moles of Mal-C5-NCO in solution. The calculated amount of product in solution was 23.2 mmole for a yield of 98% of theory. NCO reagent (concentration was 0.42 mmole/g) was used to prepare a macromer in Example 14.

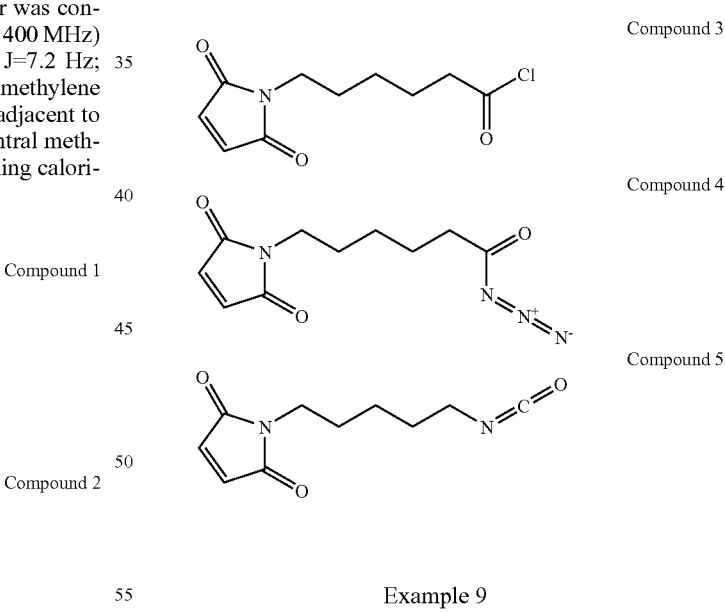

Compound 3

Compound 4

Compound 5

Example 9

Preparation of 3-(acryloyloxy)propanoic acid (2-carboxyethyl acryate; CEA)

Acrylic acid (100 g; 1.39 mole) and phenothiazine (0.1 g) were placed in a 500 mL round bottom flask. The reaction was stirred at 92° C. for 14 hours. The excess acrylic acid was removed on a rotary evaporator at 25° C. using a mechanical vacuum pump. The amount of residue obtained was 51.3 g. The CEA (Compound 6) was used in Example 10 without purification.

Compound 6

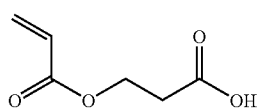

Example 10

Preparation of 3-chloro-3-oxopropyl acrylate (CEA-Cl)

CEA from Example 9 (51 g; ~0.35 mole) and dimethyl formamide (DMF; 0.2 mL; 0.26 mmole) were dissolved in $CH_2Cl_3$ (100 mL). The CEA solution was added slowly (over 2 hours) to a stirred solution of oxalyl chloride (53 mL; 0.61 mole), DMF (0.2 mL; 2.6 mmole), anthraquinone (0.5 g; 2.4 mmole), phenothiazine (0.1 g, 0.5 mmole), and $CH_2Cl_3$ (75 mL) in a 500 mL round bottom flask in an ice bath at 200 mm pressure. A dry ice condenser was used to retain the $CH_2Cl_3$ in the reaction flask. After the addition was complete the reaction was stirred at room temperature overnight. The weight of reaction solution was 369 g. A sample of the CEA-Cl (Compound 7) reaction solution (124 mg) was treated with 1,4-dibromobenzene (DBB, 6.85 mg) evaporated and dissolved in $CDCl_3$: $^1H$ NMR ($CDCl_3$, 400 MHz) δ 7.38 (s, 4H; DBB internal std.), 6.45 (d, 1H, J=17.4 Hz), 6.13 (dd, 1H, J=17.4, 10.4 Hz), 5.90 (d, 1H, J=10.4 Hz), 4.47 (t, 2H, J=5.9 Hz), 3.28 (t, 2H, J=5.9). The spectra was consistent with the desired product. There was 0.394 mole DBB for 1.0 mole CEA-Cl by integration, which gave a calculated yield of 61%. Commercially available CEA (426 g; Aldrich) was reacted with oxalyl chloride (532 mL) in a procedure similar to the one listed above. The residue CEA-Cl (490 g) was distilled using an oil bath at 140° C. at a pressure of 18 mm Hg. The distillate temperature reached 98° C. and 150 g of distillate was collected. The distillate was redistilled at 18 mm Hg at a maximum bath temperature of 120° C. The temperature range for the distillate was 30° C. to 70° C. which gave 11 g of material. The distillate appeared to be 3-chloro-3-oxopropyl 3-chloropropanoate. The residue of the second distillation (125 g; 26% of theory) was used in Example 11.

Compound 7

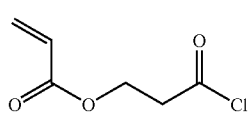

Example 11

Preparation of 3-azido-3-oxopropyl acrylate (CEA-N3)

CEA-Cl from Example 10 (109.2 g; 0.671 mole) was dissolved in acetone (135 mL). Sodium azide (57.2 g; 0.806 mole) was dissolved in water (135 mL) and chilled. The CEA-Cl solution was then added to the chilled azide solution with vigorous stirring in an ice bath for 1.5 hours. The reaction mixture was extracted two times with 150 mL of $CHCl_3$ each extraction. The $CHCl_3$ solution was passed through a silica gel column 40 mm in diameter by 127 mm. The 3-azido-3-oxopropyl acrylate (Compound 8) solution was gently agitated over dried molecular sieves at 4° C. overnight. The dried solution was used in Example 12 without purification.

Compound 8

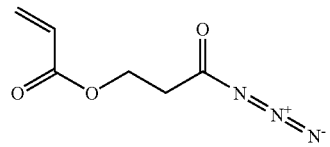

Example 12

Preparation of 2-isocyanatoethyl acrylate (EA-NCO)

The dried azide solution (from Example 11) was slowly added to refluxing $CHCl_3$, 75 mL. After the addition was completed, refluxing was continued 2 hours. The EA-NCO (Compound 9) solution (594.3 g) was protected from moisture. A sample of the EA-NCO solution (283.4 mg) was mixed with DBB (8.6 mg) and evaporated. The residue was dissolved in $CDCl_3$: $^1H$ NMR ($CDCl_3$, 400 MHz) δ 7.38 (s, 4H; DBB internal std.), 6.50 (d, 1H, J=17.3 Hz), 6.19 (dd, 1H, J=17.3, 10.5 Hz), 5.93 (d, 1H, J=10.5 Hz), 4.32 (t, 2H, J=5.3 Hz), 3.59 (t, 2H, J=5.3). The spectra was consistent with the desired EA-NCO. There was 0.165 mole DBB for 1.0 mole EA-NCO by integration, which gave a calculated concentration of 110 mg EA-NCO/g of solution. The EA-NCO solution was used to prepare a macromer in Example 13.

Compound 9

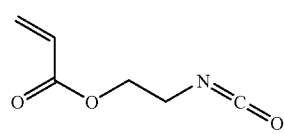

Example 13

Preparation of Maltodextrin-Acrylate Macromer (MD-Acrylate)

Maltodextrin (MD; Aldrich; 9.64 g; ~3.21 mmole; DE (Dextrose Equivalent): 4.0-7.0) was dissolved in dimethylsulfoxide (DMSO) 60 mL. The size of the maltodextrin was calculated to be in the range of 2,000 Da-4,000 Da. A solution of EA-NCO from Example 12 (24.73 g; 19.3 mmole) was evaporated and dissolved in dried DMSO (7.5 mL). The two DMSO solutions were mixed and heated to 55° C. overnight. The DMSO solution was placed in dialysis tubing (1000 MWCO, 45 mm flat width×50 cm long) and dialyzed against water for 3 days. The macromer solution was filtered and lyophilized to give 7.91 g white solid. A sample of the macromer (49 mg), and DBB (4.84 mg) was dissolved in 0.8 mL DMSO-$d_6$: $^1H$ NMR (DMSO-$d_6$, 400 MHz) δ 7.38 (s, 4H; internal std. integral value of 2.7815), 6.50, 6.19, and 5.93 (doublets, 3H; vinyl protons integral value of 3.0696). The calculated acrylate load of macromer was 0.616 μmoles/mg of polymer.

Example 14

Preparation of Maltodextrin-Maleimide Macromer (MD-Mal)

A procedure similar to Example 13 was used to make the MD-Mal macromer. A solution of Mal-C5-NCO from Example 8 (0.412 g; 1.98 mmole) was evaporated and dissolved in dried DMSO (2 mL). MD (0.991 g; 0.33 mmole) was dissolved in DMSO (5 mL). The DMSO solutions were combined and stirred at 55° C. for 16 hours. Dialysis and lyophilization gave 0.566 g product. A sample of the macromer (44 mg), and DBB (2.74 mg) was dissolved in 00.8 mL DMSO-$d_6$: $^1$H NMR (DMSO-$d_6$, 400 MHz) δ 7.38 (s, 4H; internal std. integral value of 2.3832), 6.9 (s, 2H; Maleimide protons integral value of 1.000). The calculated acrylate load of macromer was 0.222 μmoles/mg of polymer. The macromer was tested for its ability to make a matrix (see Example 17)

Example 15

Formation of Maltodextrin-Acrylate Biodegradable Matrix Using MTA-PAAm 250 mg of MD-Acrylate as prepared in Example 13 was placed in an 8 mL amber vial. To the MD-Acrylate was added 3 mg of MTA-PAAm (lyophilized), 2 μL of 2-NVP, and 1 mL of 1× phosphate-buffered saline (1×PBS), providing a composition having MD-Acrylate at 250 mg/mL. The reagents were then mixed for one hour on a shaker at 37° C. The mixture in an amount of 50 μL was placed onto a glass slide and illuminated for 40 seconds with an EFOS 100 SS illumination system equipped with a 400-500 nm filter. After illumination the polymer was found to form a semi-firm gel having elastomeric properties.

Example 16

Formation of MD-Acrylate Biodegradable Matrix Using Camphorquinone 250 mg of MD-acrylate as prepared in Example 13 was placed in an 8 mL amber vial. To the MD-Acrylate was added 14 mg of camphorquinone-10-sulfonic acid hydrate (Toronto Research Chemicals, Inc.), 3 μL of 2-NVP, and 1 mL of distilled water. The reagents were then mixed for one hour on a shaker at 37° C. The mixture in an amount of 50 μL was placed onto a glass slide and illuminated for 40 seconds with a SmartliteIQ™ LED curing light (Dentsply Caulk). After illumination the polymer was found to form a semi-firm gel having with elastomeric properties.

Example 17

Formation of MD-Mal Biodegradable Matrix Using MTA-PAAm 250 mg of MD-Mal as prepared in Example 14 was placed in an 8 mL amber vial. To the MD-Mal was added 3 mg of MTA-PAAm (lyophilized), 2 μL of 2-NVP, and 1 mL of 1× phosphate-buffered saline (1×PBS). The reagents were then mixed for one hour on a shaker at 37° C. The mixture in an amount of 50 μL was placed onto a glass slide and illuminated for 40 seconds with an EFOS 100 SS illumination system equipped with a 400-500 nm filter. After illumination the polymer was found to form a semi-firm gel having elastomeric properties.

Example 18

Coating a PEBAX® Rod with MD-Acrylate 100 mg photo-derivatized poly(vinylpyrrolidone) (photo-PVP) as prepared as described in U.S. Pat. No. 5,637,460, and the photoinitiator tetrakis (4-benzoylbenzyl ether) of pentaerythritol ["tetra-BBE-PET"] (5 mg), prepared as described in U.S. Pat. No. 5,414,075 (Example 1) and commercially available from SurModics, Inc. (Eden Prairie, Minn.) as PR01, were mixed with 10 mL isopropyl alcohol (IPA; Fisher) for 1 minute. The mixture in an amount of 1 mL was placed into a 1.8 mL eppendorf tube (VWR). A 1.2 cm PEBAX® rod (Medical Profiles, Inc) was dipped into the solution for 10 seconds, at a dip rate of 0.1 cm/second, and then removed at the same rate. The rod was allowed to air dry for 5 minutes. The rod was placed into a Dymax Lightweld PC-2 illumination system (Dymax Corp.; light intensity 6.5 mW/cm$^2$), 30 cm from light source, illuminated for 180 seconds, and then removed.

300 mg of MD-Acrylate, as prepared in Example 13, was placed in an 8 mL amber vial. To the MD-Acrylate was added 4,5-bis(4-benzoylphenylmethyleneoxy)benzene-1,3-disulfonic acid (5 mg)(DBDS), prepared as described in U.S. Pat. No. 6,278,018 (Example 1) and commercially available from SurModics, Inc. (Eden Prairie, Minn.) as DBDS, and 1 mL of 1× phosphate-buffered saline (1×PBS). The reagents were then mixed for one hour on a shaker at 37° C. The mixture in an amount of 1 mL was placed into a 1.8 mL eppendorf tube (VWR). The photo-PVP/tetra-BBE-PET coated PEBAX® rod was dipped into the mixture for 30 seconds, at a dip rate of 0.3 cm/s, and then removed at the same rate. The rod was immediately placed into a Dymax Lightweld PC-2 illumination system (Dymax Corp.; light intensity 6.5 mW/cm$^2$), 30 cm from light source, and illuminated for 180 seconds and then removed.

The MD-Acrylate coated rod was examined under Scanning Electron Microscope (SEM; LEO Supra 35 VP); the MD-Acrylate coating thickness varied from 2.1 μm to 2.5 μm, with an average coating thickness of 2.3 μm.

Example 19

Bioactive Agent Incorporation/Release from a MD-Acrylate Matrix 500 mg of MD-Acrylate as prepared in Example 13 was placed in an 8 mL amber vial. To the MD-Acrylate was added 3 mg of MTA-PAAm (lyophilized), 2 μL of 2-NVP, and 1 mL of 1× phosphate-buffered saline (1×PBS). The reagents were then mixed for one hour on a shaker at 37° C. To this mixture was added either 5 mg 70 kD FITC-Dextran or 5 mg 10 kD FITC-Dextran (Sigma) and vortexed for 30 seconds. The mixture in an amount of 200 μL was placed into a Teflon well plate (8 mm diameter, 4 mm deep) and illuminated for 40 seconds with an EFOS 100 SS illumination system equipped with a 400-500 nm filter. The formed matrix was loose, and not as well crosslinked as the formed MD-acrylate matrix in Example 17. After illumination, the matrix was transferred to a 12 well plate (Falcon) and placed in a well containing 0.6 mL PBS. At daily intervals for 6 days, 150 μL of PBS was removed from each well and placed into a 96 well plate. The remaining 850 μL were removed from the samples, and replaced with 1 mL fresh PBS. The 96 well plate was analyzed for FITC-Dextran on a spectrophotometer (Shimadzu) at 490 absorbance. Results showed that at least 70% of the detectable 10 kd or 70 kD FITC-Dextran was released from the matrix after 2 days. Visual observation showed that an unquantified amount of 10 kD or 70 kD FITC-Dextran remained within the matrix after 6 days.

Example 20

Enzyme Degradation of a MD-Acrylate Matrix

A MD-Acrylate-coated PEBAX rod (from Example 18) was placed in 5 mL of 1× phosphate-buffered saline (PBS) containing 24 μg alpha-Amylase (Sigma; catalog #A6814) for 7 days on a rotating plate at 37° C. After 7 days, the rod was removed from the PBS and washed with distilled water. The rod was then examined under a Scanning Electron Microscope (LEO Supra 35 VP); upon examination, no trace of the MD-Acrylate coating was detected. As a control, a MD-Acrylate-coated PEBAX was placed in 1× phosphate-buffered saline (PBS) without alpha-Amylase; upon examination, the MD-Acrylate coating was intact and showed no signs of degradation.

Example 21

Polyalditol-Acrylate Synthesis

Polyalditol (PA; GPC; 9.64 g; ~3.21 mmole) was dissolved in dimethylsulfoxide (DMSO) 60 mL. The size of the polyalditol was calculated to be in the range of 2,000 Da -4,000 Da. A solution of EA-NCO from Example 12 (24.73 g; 19.3 mmole) was evaporated and dissolved in dried DMSO (7.5 mL). The two DMSO solutions were mixed and heated to 55° C. overnight. The DMSO solution was placed in dialysis tubing (1000 MWCO, 45 mm flat width×50 cm long) and dialyzed against water for 3 days. The polyalditol macromer solution was filtered and lyophilized to give 7.91 g white solid. A sample of the macromer (49 mg), and DBB (4.84 mg) was dissolved in 0.8 mL DMSO-$d_6$: $^1$H NMR (DMSO-$d_6$, 400 MHz) δ 7.38 (s, 4H; internal std. integral value of 2.7815), 6.50, 6.19, and 5.93 (doublets, 3H; vinyl protons integral value of 3.0696). The calculated acrylate load of macromer was 0.616 μmoles/mg of polymer.

Example 22

Maltodextrin-Acrylate Filaments 1,100 milligrams of MD-Acrylate as prepared in Example 13 was placed in an 8 mL amber vial. To the MD-Acrylate was added 1 mg of a photoinitiator 4,5-bis(4-benzoylphenyl-methyleneoxy)benzene-1,3-disulfonic acid (5 mg) (DBDS) and 1 mL of 1× phosphate-buffered saline (PBS). The reagents were then mixed for one hour on a shaker at 37° C. The mixture in an amount of 10 uL was injected, using a 23 gauge needle, into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm$^2$), 15 cm from light source, illuminated for 270 seconds, and then removed. After illumination, the filament was removed from the silicone tubing by rolling a pencil over the tubing, starting from the back. The filament was firm, which indicated complete polymerization of the MD-Acrylate. No excess liquid was observed. The filament was manipulated with forceps. Maltodextrin filaments were also made from a MD-acrylate solution having concentration of 200 mg/mL. These are physically firm and same as 1,100 mg/ml.

Example 23

Polyalditol-Acrylate Filaments 1,500 milligrams of polyalditol-acrylate as prepared in Example 21 was placed in an 8 ml amber vial. To the polyalditol-acrylate was added 1 mg of DBDS (lyophilized), 15 mg Bovine Serum Albumin, and 200 uL of 1× phosphate-buffered saline (PBS). The reagents were then mixed for one hour on a shaker at 37° C. The mixture in an amount of 10 uL was injected, using a 23 gauge needle, into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm$^2$), 15 cm from light source, illuminated for 270 seconds, and then removed. After illumination, the filament was removed from the silicone tubing by rolling a pencil over the tubing, starting from the back. The filament was firm, which indicated complete polymerization of the polyalditol-acrylate. No excess liquid was observed. The filament was manipulated with forceps

Example 24

Amylase Degradation of Maltodextrin-Acrylate Filaments

Maltodextrin-acrylate filaments were synthesized using 200 mg/mL and 1100 mg/mL MD-acrylate as described in example 22 and were tested for degradation in Amylase solutions. These filaments were placed in microcentrifuge tubes containing 1 mL of either 1×PBS (control), 1×PBS containing alpha-Amylase at 0.121 μg/mL (Sigma; catalog #A6814), or 1×PBS containing alpha-Amylase at 24 μg/mL. The tubes were then placed in an incubator at 37° C.

After 2 days in the PBS with the 0.121 μg/mL alpha-Amylase solution the 200 mg/mL filament was completely degraded, and no trace of the filament was observable. The 200 mg/mL filament in PBS (control) showed no signs of degradation.

After 33 days in the 1×PBS containing alpha-Amylase at 0.121 μg/mL, the 1100 mg/mL filament had lost some of its initial firmness (as noted by the slightly curled appearance of the filament), but was still completely intact. The 1,100 mg/mL filament in the PBS with 24 ug Amylase had completely degraded after 48 hours. The 1,100 mg/ml filament in the PBS showed no signs of degradation.

Example 25

Maltodextrin-Acrylate Filaments with Bioactive Agent and Release

MD-Acrylate in an amount of 1,100 milligrams of as prepared in Example 13 was placed in an 8 ml amber vial. To the MD-Acrylate was added 1 mg of DBDS (lyophilized), 15 mg Bovine Serum Albumin (representing the bioactive agent; and 1 mL of 1× phosphate-buffered saline (1×PBS). The reagents were then mixed for one hour on a shaker at 37° C. The mixture in an amount of 10 uL was injected, using a 23 gauge needle, into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm$^2$), 15 cm from light source, illuminated for 270 seconds, and then removed. After illumination, the filament was removed from the silicone tubing by rolling a pencil over the tubing, starting from the back. The filament was firm, which indicated complete polymerization of the MD-Acrylate. No excess liquid was observed.

The filament was placed in a 1.7 ml microcentrifuge tube with 1 ml 1×PBS. At daily intervals for 6 days, 150 μL of PBS was removed from each well and placed into a 96 well plate for subsequent analysis. The remaining 850 μL was removed from the sample, and to the tube was added 1 ml of 1×PBS. After 6 days, the filament was placed in a 1.7 ml microcentrifuge tube with 1×PBS containing alpha-Amylase at 0.121 μg/mL. At daily intervals for 35 days, 150 μL of PBS was removed from each well and placed into a 96 well plate for subsequent analysis. The remaining 850 μL was removed from the sample, and to the tube was added 1 ml of fresh 1×PBS containing alpha-Amylase at 0.121 μg/mL. The 96-well plate was analyzed for BSA using the Quanitpro Assay Kit (Sigma). For the first 6 days, there was an initial burst of BSA, followed by a very slow release. After the addition of PBS+Amylase, the rate of BSA release significantly increased, and was relatively constant over the next 35 days. Results are shown in Table 2 and FIG. 1.

TABLE 2

| Timepoint | Cumulative BSA release (% of Total BSA) |
|---|---|
| 1 | 4.8 |
| 2 | 5.35 |
| 3 | 5.7 |
| 4 | 5.98 |
| 5 | 6.19 |
| 6 | 6.36 |
| 7 | 9.46 |
| 8 | 10.7 |
| 9 | 11.82 |
| 10 | 12.94 |
| 11 | 14.01 |
| 12 | 15.06 |
| 13 | 16.11 |
| 14 | 17.23 |
| 15 | 18.11 |
| 16 | 19.04 |
| 17 | 19.92 |
| 18 | 21.26 |
| 19 | 22.15 |
| 20 | 23.04 |
| 21 | 24.06 |
| 22 | 25.35 |
| 23 | 26.31 |
| 24 | 26.91 |
| 25 | 27.51 |
| 26 | 28.63 |
| 27 | 29.19 |
| 28 | 29.75 |
| 29 | 30.44 |
| 30 | 31.11 |
| 31 | 31.43 |
| 32 | 31.63 |
| 33 | 31.83 |
| 34 | 32.07 |
| 35 | 32.31 |
| 36 | 32.72 |
| 37 | 32.95 |
| 38 | 33.27 |
| 39 | 33.83 |
| 40 | 34.15 |
| 41 | 34.43 |
| 42 | 34.71 |

Example 26

Polyalditol-Acrylate Filaments with Bioactive Agent and Release

Polyaldtiol-acrylate in an amount of 1,500 mg of as prepared in Example 21 was placed in an 8 ml amber vial. To the PA-Acrylate was added 1 mg of DBDS (lyophilized), 15 mg Bovine Serum Albumin, and 1 mL of 1× phosphate-buffered saline (1×PBS). The reagents were then mixed for one hour on a shaker at 37° C. The mixture in an amount of 10 uL was injected, using a 23 gauge needle, into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm$^2$), 15 cm from light source, illuminated for 270 seconds, and then removed. After illumination, the filament was removed from the silicone tubing by rolling a pencil over the tubing, starting from the back. The filament was firm, which indicated complete polymerization of the polyalditol-acrylate. No excess liquid was observed. The filament was manipulated with forceps.

The filament was placed in a 1.7 ml microcentrifuge tube with 1 ml PBS containing alpha-Amylase at 0.121 μg/mL. At daily intervals for 15 days, 150 μl of PBS was removed from each well and placed into a 96 well plate for subsequent analysis. The remaining 850 μL was removed from the sample, and to the tube was added 1 ml of fresh PBS containing alpha-Amylase at 0.121 μg/mL. The 96-well plate was analyzed for BSA using the Quanitpro Assay Kit (Sigma).

Example 27

Maltodextrin-Acrylate Filaments with Bioactive Agent and Release

Maltodextrin filaments were synthesized using a 1,100 mg/mL solution as described in example 25 using an anti-horseradish peroxidase antibody (P7899; Sigma) instead of BSA. The filament contained 800 ug of the anti-horseradish peroxidase antibody. The filament was placed in a 1.7 ml microcentrifuge tube containing 1 ml of 1×PBS containing alpha-Amylase at 0.121 μg/mL. At daily intervals for 5 days, 100 μl of PBS was removed from the sample, placed into a 96 well plate and incubated for 60 minutes at 37° C. The remaining 850 μL was removed from the sample, and replaced with 1 ml fresh 1×PBS containing alpha-Amylase at 0.121 μg/mL. After 1 hour, the plate was washed three times with 1 ml PBS/Tween (Sigma). 150 ul StabilCoat™ Immunoassay Stabilizer (SurModics, Eden Prairie, Minn.) was added to the well and incubated for 30 minutes at room temperature. After 30 minutes, the 96-well plate was washed three times with PBS/Tween. A solution of 0.5 mg/ml Horseradish Peroxidase (Sigma) in 1×PBS (100 uL) was added to the well and incubated for 60 minutes. After 60 minutes, the 96-well plate was washed six times with PBS/Tween. A chromogenic assay was then performed. After 15 minutes, the 96 well plate was analyzed for HRP conjugate on a spectrophotometer (Tecan) at 560 nm absorbance. Detectable Antibody was found at each time point.

Example 28

Bioactive Agent Incorporation and Release from a MD-Acrylate/Photo-PVP-Coated PEBAX Rod 100 mg photo-PVP and 5 mg the photoinitiator tetra-BBE-PET were mixed with 10 ml Isopropyl alcohol (IPA; Fisher) for 1 minute. The mixture in an amount of 1 ml was placed into a 1.7 ml eppendorf tube (VWR). A 1.2 cm PEBAX® rod (Medical Profiles, Inc) was dipped into the solution for 10 seconds, at a dip rate of 0.75 cm/second, and then removed at the same rate. The rod was allowed to air dry for 10 minutes. The rod was placed into a Dymax Lightweld PC-2 illumination system (Dymax Corp.; light intensity 6.5 mW/cm$^2$), 30 cm from light source, illuminated for 180 seconds, and then removed.

1000 mg of MD-Acrylate, as prepared in Example 13 was placed in an 8 mL amber vial. To the MD-Acrylate was added 5 mg DBDS, 1 ml of 1× phosphate-buffered saline (PBS), and 100 mg BSA. The reagents were then mixed for one hour on a shaker at 37° C. The mixture in an amount of 1 ml was placed into a 1.8 ml eppendorf tube (VWR). The photo-PVP/tetra-BBE-PET coated PEBAX® rod was dipped into the mixture for 30 seconds, at a dip rate of 0.3 cm/s, and then removed at the same rate. The rod was immediately placed into a Dymax Lightweld PC-2 illumination system (Dymax Corp.; light intensity 6.5 mW/cm$^2$), 30 cm from light source, and illuminated for 180 seconds and then removed.

Figure 2:
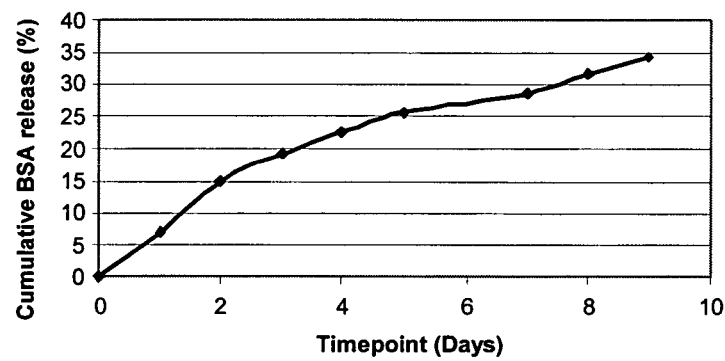
FIG. 2 is a graph of cumulative BSA release from maltodextrin-acrylate/photo-PVP-coated PEBAX rod treated with amylase, over a period of time.

The rod was placed in a 1.7 ml microcentrifuge tube with 1 ml 1×PBS containing alpha-Amylase at 0.121 µg/mL. At intervals for 9 days, 150 µl of PBS was removed from each well and placed into a 96 well plate. The remaining 850 µl were removed from the samples, and replaced with 1 ml fresh 1×PBS containing alpha-Amylase at 0.121 µg/mL. The 96 well-plate was analyzed for BSA release using the Quanitpro Assay Kit (Sigma). BSA was detected at each timepoint. Results are shown in Table 3 and FIG. 2.

TABLE 3

| Timepoint | Cumulative BSA release (% of Total BSA) |
| --- | --- |
| 1 | 7.0 |
| 2 | 15.0 |
| 3 | 19.1 |
| 4 | 22.7 |
| 5 | 25.6 |
| 7 | 28.6 |
| 8 | 31.5 |
| 9 | 34.2 |

Example 29

Degradation of MD-Acrylate Coating

The MD-Acrylate-coated PEBAX rod (as prepared in Example 28) was placed in 5 ml of 1× phosphate-buffered saline (PBS) containing alpha-Amylase at 24 µg/mL for 7 days on a rotating plate at 37° C. After 7 days, the rod was removed from the PBS and washed with distilled water. The rod was then examined under a Scanning Electron Microscope (LEO Supra 35 VP); upon examination, no trace of the MD-Acrylate coating was detected.

Example 30

Degradation of MD-Acrylate Filament in Vitreal Fluid

A circumferential dissection of the anterior segment (cornea, aqueous humour, lens) of porcine eye was performed, and the vitreous was squeezed out from the globe into a 20 mL amber vial; approx 10 mL total was retrieved from a total of four eyes. 200 mg/mL and 1100 mg/mL Maltodextrin filaments, formed in example 21, were placed into 2 mL of the vitreous solution, and placed at 37° C. on a rotator plate. The 200 mg/mL filament had completely dissolved after 24 hours. The 1,100 mg/mL filaments completely degraded after 30 days in the vitreous.

Example 31

Formation of a Maltodextrin-Acrylate Biodegradable Matrix Using REDOX Chemistry

Two solutions were prepared. Solution #1 was prepared as follows: 250 mg of MD-acrylate as prepared in example 13 was placed in an 8 mL vial. To the MD-acrylate was added 15 mg ferrous gluconate hydrate (Sigma), 30 mg Ascorbic Acid (Sigma), 67 uL AMPS (Lubrizol) and 1,000 uL deionized water. Solution #2 was prepared as follows: 250 mg of MD-acrylate as prepared in example 13 was placed in a second 8 mL vial. To this MD-acrylate was added 30 uL AMPS, 80 uL Hydrogen Peroxide (Sigma) and 890 uL 0.1 M Acetate buffer (pH 5.5).

50 uL of Solution #1 was added to a glass slide. 50 uL of solution #2 was added to Solution #1 with slight vortexing. After mixing for 2 seconds, the mixture polymerized and formed a semi-firm gel having elastomeric properties.

Example 32

Formation of Maltodextrin-Acrylate Biodegradable Matrix Using REDOX Chemistry

Two solutions were prepared, similar to Example 31, but in this Example Solution #1 different concentrations of ferrous gluconate hydrate (Sigma) and ascorbic acid were used. Solution #1 was prepared as follows: 250 mg of MD-acrylate (as prepared in example 13) was placed in an 8 mL vial. To the MD-acrylate was added 5 mg ferrous gluconate hydrate (Sigma), 40 mg ascorbic acid (Sigma), 67 uL AMPS (Lubrizol) and 1,000 uL deionized water. Solution #2 was prepared as follows: 250 mg of MD-acrylate as prepared in example 7 was placed in a second 8 mL vial. To this MD-acrylate was added 30 uL AMPS, 80 uL Hydrogen Peroxide (Sigma) and 890 uL 0.1 M Acetate buffer (pH 5.5).

50 uL of Solution #1 was added to a glass slide. 50 uL of solution #2 was added to Solution #1 with slight vortexing. After mixing for 8 seconds, the mixture polymerized and formed a semi-firm gel having elastomeric properties.

Example 33

Formation of Maltodextrin-Acrylate Biodegradable Matrix Using REDOX Chemistry

Two solutions were prepared. Solution #1 was prepared as follows: 250 mg of MD-acrylate (as prepared in example 13) was placed in an 8 mL vial. To the MD-acrylate was added 15 mg Iron (II) L-Ascorbate (Sigma), 30 mg Ascorbic Acid (Sigma), 67 uL AMPS (Lubrizol) and 1,000 uL deionized water. Solution #2 was prepared as follows: 250 mg of MD-acrylate as prepared in example 7 was placed in a second 8 mL vial. To this MD-acrylate was added 30 uL AMPS, 80 uL hydrogen peroxide (Sigma) and 890 uL 0.1 M Acetate buffer (pH 5.5).

50 uL of Solution #1 was added to a glass slide. 50 uL of solution #2 was added to Solution #1 with slight vortexing. After mixing for 2 seconds, the mixture polymerized and formed a semi-firm gel having elastomeric properties.

Example 34

Formation of Polyalditol-Acrylate Biodegradable Matrix Using REDOX Chemistry

Two solutions were prepared. Solution #1 was prepared as follows: 1,000 mg of Polyalditol-acrylate as prepared in Example 21 was placed in an 8 mL vial. To the Polyalditol-acrylate was added 15 mg Ferrous Sulfate Heptahydrate (Sigma), 30 mg Ascorbic Acid (Sigma), 67 uL AMPS (Lubrizol) and 1,000 uL deionized water; Solution #2 was prepared as follows: 1,000 mg of Polyalditol-acrylate as prepared in example was placed in a second 8 mL vial. To this Polyalditol-acrylate was added 30 uL AMPS, 80 uL Hydrogen Peroxide (Sigma) and 890 uL 0.1 M Acetate buffer (pH 5.5).

50 uL of Solution #1 was added to a glass slide. 50 uL of solution #2 was added to Solution #1 with slight vortexing. After mixing for 2 seconds, the mixture polymerized and formed a semi-firm gel having elastomeric properties.

Example 35

Coating a PEBAX® rod with MD-Acrylate Using REDOX

Photo-PVP (100 mg) and the photoinitiator tetra-BBE-PET (5 mg), were mixed with 10 mL isopropyl alcohol (IPA; Fisher) for 1 minute. The mixture in an amount of 1 mL was placed into a 1.8 mL eppendorf tube (VWR). A 1.2 cm PEBAX® rod (Medical Profiles, Inc) was dipped into the solution for 10 seconds, at a dip rate of 0.1 cm/second, and then removed at the same rate. The rod was allowed to air dry for 5 minutes. The rod was placed into a Dymax Lightweld PC-2 illumination system (Dymax Corp.; light intensity 6.5 mW/cm$^2$), 30 cm from light source, illuminated for 180 seconds, and then removed.

Two solutions were prepared. Solution #1 was prepared as follows: 250 mg of MD-acrylate (as prepared in example 13) was placed in an 8 ml vial. To the MD-acrylate was added 15 mg Iron (II) Ascorbate (Sigma), 30 mg Ascorbic Acid (Sigma), 67 ul AMPS (Lubrizol) and 1,000 ul deionized water. Solution #2 was prepared as follows: 250 mg of MD-acrylate was placed in a second 8 ml vial. To this MD-acrylate was added 30 ul AMPS, 80 ul Hydrogen Peroxide (Sigma) and 890 ul 0.1 M Acetate buffer (pH 5.5).

Solution #1 in an amount of 1 mL was placed into a 1.8 mL eppendorf tube (VWR). The photo-PVP/tetra-BBE-PET coated PEBAX® rod was dipped into the mixture for 30 seconds, at a dip rate of 0.5 cm/s, and then removed at the same rate. The PEBAX rod was allowed to air dry for 10 minutes. Solution #2 in an amount of 1 mL was placed into a second 1.8 mL eppendorf tube (VWR). The photo-PVP/tetra-BBE-PET and Solution #1 coated PEBAX® rod was dipped into the mixture for 30 seconds, at a dip rate of 0.5 cm/s, and then removed at the same rate.

The MD-Acrylate coated rod was examined under Scanning Electron Microscope (SEM; LEO Supra 35 VP); the MD-Acrylate coating thickness ranged from 15 to 20 um, with an average thickness of 16.8 um.

Example 36

Bioactive Agent Incorporation into a MD-Acrylate Matrix

Two solutions were prepared. Solution #1 was prepared as follows: 250 mg of MD-acrylate (as prepared in example 13) was placed in an 8 ml vial. To the MD-acrylate was added 15 mg Iron (II) Acetate (Sigma), 30 mg Ascorbic Acid (Sigma), 67 ul AMPS (Lubrizol), 75 mg Bovine Serum Albumin (BSA; representing the bioactive agent) and 1,000 μL deionized water. Solution #1 was prepared as follows: 250 mg of MD-acrylate was placed in a second 8 ml vial. To this MD-acrylate was added 30 μL AMPS, 80 μL Hydrogen Peroxide (Sigma), 75 mg BSA and 890 μL Acetate buffer (pH 5.5).

50 μL of Solution #1 was added to a glass slide. 50 μL of solution #2 was added to Solution #1 with slight vortexing. After mixing for 2 seconds, the mixture polymerized and formed a semi-firm gel having elastomeric properties.

Example 37

Enzyme Degradation of a MD-Acrylate Matrix Formed by REDOX

Maltodextrin-acrylate filaments were prepared using the reagents at concentrations as described in Example 31. These filaments were placed in microcentrifuge tubes containing 1 ml either Phosphate Buffered Saline (PBS) or 1×PBS containing alpha-Amylase at 0.121 μg/mL. The tubes were then placed in an incubator at 37° C.

After 4 days in the 1×PBS containing alpha-Amylase at 0.121 μg/mL, the 250 mg/mL filament had completely degraded, leaving no trace of the matrix. The matrix in PBS showed no signs of degradation.

Example 38

Figure 3:
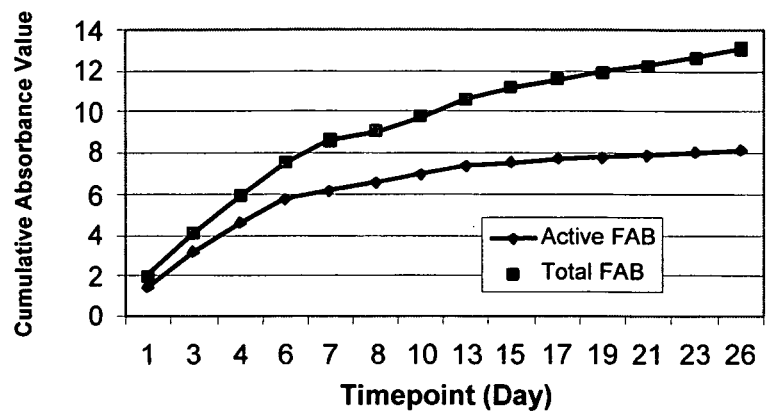
FIG. 3 is a graph of cumulative absorbance values of active and total IgG Fab fragment release from maltodextrin-acrylate filaments treated with amylase, over a period of time.

FAB Fragment Incorporation and Release from a MD-Acrylate Filament 600 milligrams of MD-Acrylate as prepared in Example 13 was placed in an 8 mL amber vial. To the MD-Acrylate was added 5 mg of DBDS (lyophilized), 10 mg Rabbit Anti-Goat Fragment Antibody (catalog #300-007-003; Jackson Immunological Research, West Grove, Pa.) and 1 mL of 1× phosphate-buffered saline (PBS). The reagents were then mixed for one hour on a shaker at 37° C. The mixture in an amount of 10 μL was pipetted into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm$^2$), 15 cm from light source, illuminated for 270 seconds, and then removed. After illumination, the filament was removed from the silicone tubing by rolling a pencil over the tubing, starting from the back. The filament was firm and completely crosslinked, with no excess liquid. The filament was placed in a 1.7 mL microcentrifuge tube with 0.5 ml 1×PBS containing alpha-Amylase at 0.121 μg/mL (eluent solution). At predetermined intervals for 17 days, 200 μL of the eluent solution was removed from each tube, and 100 μL was placed into two 96 well plates. The remaining 300 μL were removed from the samples, and replaced with 0.5 mL fresh 1×PBS containing alpha-Amylase at 0.121 μg/mL. The 96 well plates were analyzed for total FAB molecule release and FAB activity using an Enzyme-Linked Immunosorbent Assay (ELISA). Briefly, the 100 μL eluent solution was incubated at 37° C. for one hour and then washed 3× with 2 ml PBS/Tween 20 (Sigma). The wells were blocked with 100 μL StabilCoat™ for 1 hour at room temperature and then washed 3× with 2 mL PBS/Tween 20. 100 uL of either 0.1 ug/mL (in PBS/Tween) HRP-labeled Goat IgG (Jackson Immunological; catalog #005-030-003) for molecule activity or 0.08 ug/mL (in PBS/Tween) HRP-labeled Goat anti-Rabbit IgG (Jackson Immunological; catalog #111-305-003) was incubated for 1 hour at 37° C. The wells were washed 6× with 2 mL PBS/Tween 20. 100 μL of TMB Microwell Peroxidase Substrate System (KPL, Catalog #50-76-00; Gaithersburg, Md.) as added to each well. After 15 minutes, the 96 well plate was analyzed for HRP conjugate on a spectrophotometer (Tecan) at 650 nm absorbance. Detectable Antibody was found at each time-point. Results are shown in Table 4 and FIG. 3.

TABLE 4

| | Fab Fragment release ABS values | |
|---|---|---|
| Timepoint (Day) | Cumulative Active FAB Abs at 650 nm | Cumulative Total Fab Abs at 650 nm |
| 1 | 1.37 | 1.97 |
| 3 | 3.12 | 4.07 |
| 4 | 4.54 | 5.87 |
| 6 | 5.69 | 7.54 |
| 7 | 6.12 | 8.60 |
| 8 | 6.53 | 9.01 |
| 10 | 6.94 | 9.79 |
| 13 | 7.34 | 10.64 |
| 15 | 7.54 | 11.18 |
| 17 | 7.71 | 11.62 |
| 19 | 7.81 | 11.92 |
| 21 | 7.90 | 12.28 |
| 23 | 8.00 | 12.68 |
| 26 | 8.09 | 13.11 |

Example 39

Rabbit Antibody Incorporation and Release from a MD-Acylate (Redox Polymerization) Coated Stainless Steel Rod 316 V or 304 V stainless steel rods (0.035" diameter; Small Parts, Inc.) were cleaned by wiping the rods with isopropyl alcohol (IPA) soaked Alpha 10 clean-wipes (Texwipe; Kernersville. N.C.) and then sonicating the rods in a solution of 10% Valtron SP2200 detergent (Valtech Corp.) in hot tap water for 10 minutes. The rods were then rinsed 3× with deionized water followed by a 1 minute sonication in hot tap water; the rinse and sonication steps were then repeated.

A 0.5% 1,4-bis(trimethoxysilylethyl)benzene (B2495.6, UCT, Bristol, Pa.) solution in 89.5% IPA and 10% deionized water was prepared (See Example 1 of U.S. Pat. No. 6,706, 408B2-) and the cleaned rods were dipped into the silane solution within 2 minutes of coming out of the deionized rinse. The rods were allowed to dwell in the silane solution for 3 minutes and then pulled out at a rate of 1.0 cm/s. They were allowed to air dry for 2 minutes at room temperature and then placed at 110° C. for 5 minutes.

A solution of photo-PVP (15 mg/mL), DBDS (1 mg/mL), tetra-BBE-PET 0.075 (mg/mL) and PVP K90 (20 mg/ml; BASF) was prepared in 60% IPA/40% water) (see also Example 1 of U.S. Pat. No. 6,706,408B2). The silane treated rods were dip coated into the above solution using the following parameters:

Velocity in =2.0 cm/s; dwell time=60 seconds; velocity out=0.1 cm/s The coated rods were allowed to air dry at room temperature for 5 minutes and then illuminated in a Dymax lamp UV light chamber, with rotation, for 3 minutes. The dipping procedure was then repeated with a dwell time of 120 seconds (all other dipping parameters the same).

Two solutions were prepared. The first solution (#1) was prepared by placing 600 mg of MD-acrylate (as prepared in example 13) into an 8 mL vial and then adding 9 mg iron (II) ascorbate (Sigma), 30 mg ascorbic acid (Sigma), 67 μL AMPS (Lubrizol), 16 mg Rabbit Anti-HRP antibody (Sigma; catalog #P7899), and 1,000 μL deionized water. The second solution (#2) was prepared by placing 600 mg of MD-acrylate in a second 8 mL vial and then adding 30 μL AMPS, 16 mg Rabbit Anti-HRP antibody (Sigma; catalog #P7899), 80 μL hydrogen peroxide (Sigma) and 890 μL 0.1 M Acetate buffer (pH 5.5).

Solution #1 in an amount of 1 mL was placed into a 1.8 mL eppendorf tube (VWR). The (PV01/K90/DBDS/tetra-BBE-PET)-coated stainless steel rod (20 mm in length) was dipped into the mixture for 20 seconds, at a dip rate of 0.75 cm/s, and then removed at the same rate. The rod was allowed to air dry for 10 minutes. Solution #2 in an amount of 1 mL was placed into a second 1.8 mL eppendorf tube (VWR). The (PV01/K90/DBDS/tetra-BBE-PET)-coated and Solution #1 coated rod was dipped into the Solution #2 for 20 seconds, at a dip rate of 0.75 cm/s, and then removed at the same rate. Contact with Solution #2 initiated the redox reaction and caused formation of an MD-Acrylate coated layer on the PV01/K90/DBDS/tetra-BBE-PET coated layer; the MD-Acrylate coating was cured within 10 seconds The coated rod was examined under Optical Inferometer Microscope (Veeco) which revealed that the MD-Acrylate coating layer had a thickness of 70 μm.

The MD-Acrylate coated rod was placed in a 0.6 mL microcentrifuge tube with 0.5 ml 1×PBS containing alpha-Amylase at 0.121 μg/mL (eluent solution) to assess release of the bioactive agent (antibody) from the coating.

Figure 4:
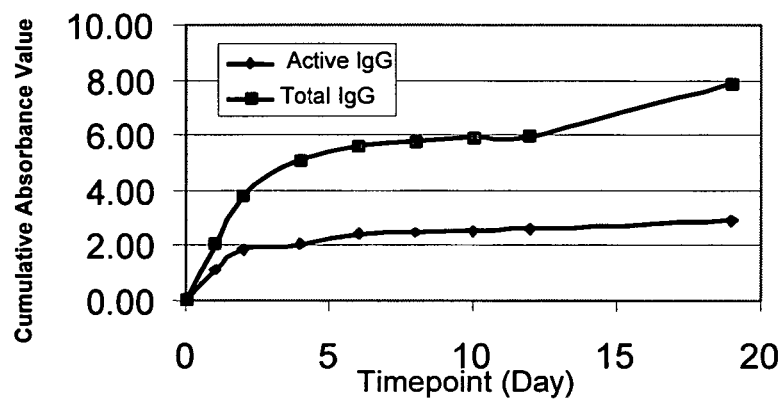
FIG. 4 is a graph of cumulative absorbance values of active and total IgG release from maltodextrin-acrylate(redox)/photo-PVP-coated stainless steel rods treated with amylase, over a period of time.

At predetermined intervals for 19 days, 200 μL of the eluent solution was removed from the tube, which was divided into two 100 μL aliquots and placed into two 96 well plates. The remaining 300 μL was removed from the microcentrifuge tube, and 0.5 mL of fresh eluent solution (1×PBS containing alpha-Amylase at 0.121 μg/mL) was added to the microcentrifuge tube having the MD-Acrylate coated rod. The eluent samples in 96 well plates were analyzed for total Rabbit Antibody molecule release and activity using an Enzyme-Linked Immunosorbent Assay (ELISA). Briefly, the 100 μL of eluent solution was incubated at 37° C. for one hour and then washed 3× with 2 ml PBS/Tween 20 (Sigma). The wells were blocked with 100 μL StabilCoat™ (SurModics, Eden Prairie, Minn.) for 1 hour at room temperature and then washed 3× with 2 ml PBS/Tween 20. 100 μL of either 0.1 μg/mL (in PBS/Tween) HRP (Sigma; catalog #P8375) for molecule activity or 0.08 ug/mL (in PBS/Tween) HRP-labeled Goat anti-Rabbit IgG (Jackson Immunological; catalog #111-305-003) was incubated for 1 hour at 37° C. The wells were washed 6× with 2 ml PBS/Tween 20. 100 μL of TMB Microwell Peroxidase Substrate System (KPL, Catalog #50-76-00; Gaithersburg, Md.) was added to each well. After 15 minutes, the 96 well plate was analyzed for HRP conjugate on a spectrophotometer (Tecan) at 650 nm absorbance. Detectable antibody was found in the eluate samples at each timepoint. Results are shown in Table 5 and FIG. 4.

TABLE 5

| Timepoint (Day) | Cumulative Active IgG Abs at 650 nm | Cumulative Total IgG Abs at 650 nm |
|---|---|---|
| 1 | 1.08 | 2.01 |
| 2 | 1.82 | 3.78 |
| 4 | 2.01 | 5.11 |
| 6 | 2.41 | 5.57 |
| 8 | 2.48 | 5.75 |
| 10 | 2.54 | 5.88 |
| 12 | 2.59 | 5.97 |
| 19 | 2.87 | 7.88 |

Example 40

Rabbit Antibody Incorporation and Release from a MD-Acrylate (Photo-Initiated Polymerization) Coated Stainless Steel Rod 316V or 304V stainless steel rods (0.035" diameter; Small Parts, Inc., Miami Lakes, Fla.) were cleaned by wiping the rods with isopropyl alcohol (IPA)-soaked Alpha 10 cleanwipe (Texwipe) and then sonicating the rods in a solution of 10% Valtron SP2200 detergent in hot tap water for 10 minutes. The rods were then rinsed 3× with deionized water followed by a 1 minute sonication in hot tap water; the rinse and sonication step was then repeated.

The cleaned rods were dipped into a 0.5% 1,4-bis(trimethoxysilylethyl)benzene solution (as described in Example 39) within 2 minutes of coming out of the deionized rinse. The rods were allowed to dwell in the silane solution for 3 minutes and then pulled out at a rate of 1.0 cm/s. The rods were allowed to air dry for 2 minutes at room temperature and then placed at 110° C. for 5 minutes.

A solution of PV01 (15 mg/mL), DBDS (1 mg/mL), tetra-BBE-PET (0.075 mg/ml) and K90 (20 mg/mL; BASF) was prepared in 60% IPA/40% water. The silane treated rods were dip coated into the above solution using the following parameters:

Velocity in =2.0 cm/s; dwell time=60 seconds; velocity out=0.1 cm/s. The coated rods were allowed to air dry at room temperature for 5 minutes and then illuminated in a Dymax lamp UV light chamber, with rotation, for 3 minutes. The dipping procedure was then repeated with a dwell time of 120 seconds (all other dipping parameters the same).

600 milligrams of MD-Acrylate as prepared in Example 13 was placed in an 8 mL amber vial. To the MD-Acrylate was added 5 mg of DBDS (lyophilized), 16 mg Rabbit Anti-HRP antibody (Sigma; catalog #P7899) and 1 ml of 1× phosphate-buffered saline (PBS). The reagents were then mixed for one hour on a shaker at 37° C. The MD-Acrylate solution in an amount of 1 mL was placed into a 1.8 mL eppendorf tube (VWR). The (PV01/K90/DBDS/tetra-BBE-PET)-coated stainless steel rod (20 mm in length) was dipped into the mixture for 20 seconds, at a dip rate of 0.75 cm/s, and then removed at the same rate. The rod was then immediately illuminated in a Dymax lamp UV light chamber, with rotation, for 3 minutes. The rod was allowed to air dry for 5 minutes, and the dipping and illuminating procedures were repeated one more time.

The MD-Acrylate coated rod was examined under Optical Inferometer Microscope (Veeco); the MD-Acrylate coating layer had a coating thickness of 20 μm.

The MD-Acrylate coated rod was placed in a 0.6 mL microcentrifuge tube with 0.5 mL 1×PBS containing alpha-Amylase at 0.121 μg/mL (eluent solution) to assess degradation of the coating and release of the bioactive agent (antibody) from the coating. At predetermined intervals for 25 days, 200 μL of the eluent solution was removed from each tube, which was divided into two 100 μL aliquots and placed into two 96 well plates. The remaining 300 μL was removed from the microcentrifuge tube, and 0.5 mL of fresh eluent solution (1×PBS containing alpha-Amylase at 0.121 μg/mL) was added to the microcentrifuge tube having the MD-Acrylate coated rod.

The 96 well plates were analyzed for total Rabbit Antibody molecule release and activity using an Enzyme-Linked Immunosorbent Assay (ELISA). Briefly, the 100 μL eluent solution was added to the wells and incubated at 37° C. for one hour and then washed 3× with 2 mL PBS/Tween 20 (Sigma). The wells were blocked with 100 μL StabilCoat™ for 1 hour at room temperature and then washed 3× with 2 mL PBS/Tween 20. 100 μL of either 0.1 ug/mL (in PBS/Tween) HRP (Sigma; catalog #P8375) for molecule activity or 0.08 ug/mL (in PBS/Tween) HRP-labeled Goat anti-Rabbit IgG (Jackson Immunological; catalog #111-305-003) was incubated for 1 hour at 37° C. The wells were washed 6× with 2 mL PBS/Tween 20. 100 μL of TMB Microwell Peroxidase Substrate System (KPL, Catalog #50-76-00; Gaithersburg, Md.) was added to each well. After 15 minutes, the 96 well plate was analyzed for HRP conjugate on a spectrophotometer (Tecan) at 650 nm absorbance. Detectable antibody was found in the eluate samples at each time point.

Figure 5:
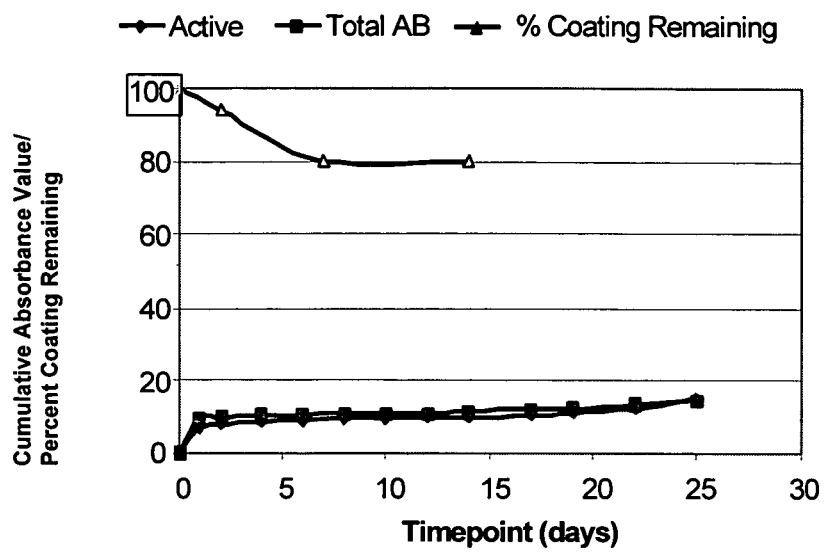
FIG. 5 is a graph of cumulative absorbance values of active and total IgG release from maltodextrin-acrylate(photoinitiation)/photo-PVP-coated stainless steel rods treated with amylase and percent degradation of the maltodextrin-acrylate coating, over a period of time.

Based on the initial weight of the coating before degradation, a theoretical maximum concentration of the antibody was calculated. In addition to measurements performed by ELISA, the MD-Acrylate coated rod was weighed at various time points to determine the amount of material of the MD-Acrylate coated layer lost from the rods due to amylase digestion. Results are shown in Table 6 and FIG. 5.

TABLE 6

| Timepoint (Day) | Cumulative Active IgG release (%) (ELISA) | Cumulative Total IgG release (%) (ELISA) | MD-acrylate coating remaining (%) | Maximum theoretical total IgG release (%) |
|---|---|---|---|---|
| 1 | 7.14 | 9.29 | | |
| 2 | 8.14 | 10.14 | 83 | 17 |
| 4 | 8.49 | 10.29 | | |
| 6 | 8.93 | 10.49 | | |
| 7 | | | 80 | 20 |
| 8 | 9.27 | 10.76 | | |
| 10 | 9.63 | 10.90 | | |
| 12 | 10.06 | 11.19 | | |
| 14 | 10.19 | 11.36 | 80 | 20 |
| 17 | 10.65 | 11.91 | | |
| 19 | 11.19 | 12.68 | | |
| 22 | 12.62 | 13.38 | | |
| 25 | 14.76 | 14.35 | | |

Example 41

Rabbit Antibody Incorporation and Release from a MD-Acrylate Filament 600 milligrams of MD-Acrylate as prepared in Example 13 was placed in an 8 ml amber vial. To the MD-Acrylate was added 5 mg of DBDS (lyophilized), 16 mg Rabbit Antibody Anti-HRP (Sigma; catalog #P7899) and 1 ml of 1× phosphate-buffered saline (PBS). The reagents were then mixed for one hour on a shaker at 37° C. The mixture in an amount of 10 μL was pipetted into a 22 mm length opaque silicone tube (P/N 10-447-01; Helix Medical, Carpinteria, Calif.). The tubing was placed into a Dymax Lightweld PC-2 illumination system (Dymax Corp.; light intensity 6.5 mW/cm²), 15 cm from light source, illuminated for 270 seconds, and then removed. After illumination, the filament was removed from the silicone tubing by rolling a pencil over the tubing, starting from the back. The filament was firm and completely crosslinked, with no excess liquid.

Figure 6:
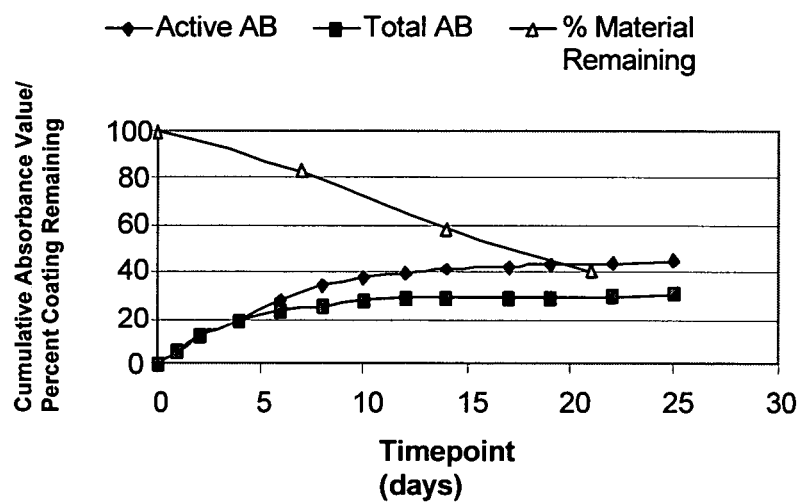
FIG. 6 is a graph of cumulative absorbance values of active and total IgG release from a maltodextrin-acrylate filament treated with amylase and percent degradation of the filament, over a period of time.

The filament was placed in a 1.7 ml microcentrifuge tube with 0.5 ml 1×PBS containing alpha-Amylase at 0.121 μg/mL (eluent solution). At predetermined intervals for 25 days, 200 μl of the eluent solution was removed from each tube, and 100 μL was placed into two 96 well plates. The remaining 300 μl were removed from the samples, and replaced with 0.5 ml fresh 1×PBS containing alpha-Amylase at 0.121 μg/mL. The 96 wellplates were analyzed for total Rabbit Antibody molecule release and activity using an Enzyme-Linked Immunosorbent Assay (ELISA). Briefly, the 100 μL eluent solution was added to the wells and incubated at 37 degrees C. for one hour and then washed 3× with 2 ml PBS/Tween 20 (Sigma). The wells were blocked with 100 μL StabilCoa™ (SurModics) for 1 hour at room temperature and then washed 3× with 2 ml PBS/Tween 20. 100 µL of either 0.1 ug/ml (in PBS/Tween) HRP (Sigma; catalog #P8375) for molecule activity or 0.08 ug/ml (in PBS/Tween) HRP-labeled Goat anti-Rabbit IgG (Jackson Immunological; catalog #111-305-003) was incubated for 1 hour at 37 degrees C. The wells were washed 6× with 2 ml PBS/Tween 20. 100 µL of TMB Microwell Peroxidase Substrate System (KPL, Catalog #50-76-00; Gaithersburg, Md.) was added to each well. After 15 minutes, the 96 well plate was analyzed for HRP conjugate on a spectrophotometer (Tecan) at 650 nm absorbance. Detectable Antibody was found at each time point. Results are shown in Table 7 and FIG. 6.

TABLE 7

| Timepoint (Day) | Cumulative Active IgG release (%) (ELISA) | Cumulative Total IgG release (%) (ELISA) | MD-acrylate coating remaining (%) | Maximum theoretical total IgG release (%) |
|---|---|---|---|---|
| 1 | 5.56 | 5.31 | | |
| 2 | 12.13 | 11.94 | | |
| 4 | 18.38 | 19.13 | | |
| 6 | 27.75 | 22.88 | | |
| 7 | | | 83 | 17 |
| 8 | 33.50 | 25.44 | | |
| 10 | 37.63 | 27.44 | | |
| 12 | 39.50 | 28.31 | | |
| 14 | 40.75 | 28.57 | 59 | 31 |
| 17 | 41.75 | 28.76 | | |
| 19 | 42.75 | 28.98 | | |
| 21 | | | 40 | 60 |
| 22 | 43.44 | 29.67 | | |
| 25 | 44.31 | 30.67 | | |

Example 42

Mechanical Testing of MD-Acrylate Discs Formed Via Redox Polymerization

MD-acrylate discs formed via redox polymerization of MD-acrylate coating solutions were tested for mechanical properties.

A first solution (#1) was prepared by placing 300 mg of MD-acrylate as prepared in Example 13 into an 8 ml vial and then adding 9 mg iron (II) ascorbate (Sigma), 30 mg ascorbic acid (Sigma), 67 µL AMPS (Lubrizol), and 1,000 µL deionized water. Solution #2 was prepared by placing 300 mg of MD-acrylate into a second 8 ml vial and then adding 30 µL AMPS, 80 µL if hydrogen peroxide (Sigma) and 890 µL of 0.1 M Acetate buffer (pH 5.5).

Viscosity of the first and second solutions were determined on a Brookfield Viscometer. The average viscosity for both solutions was 10.9 cP.

Figure 7:
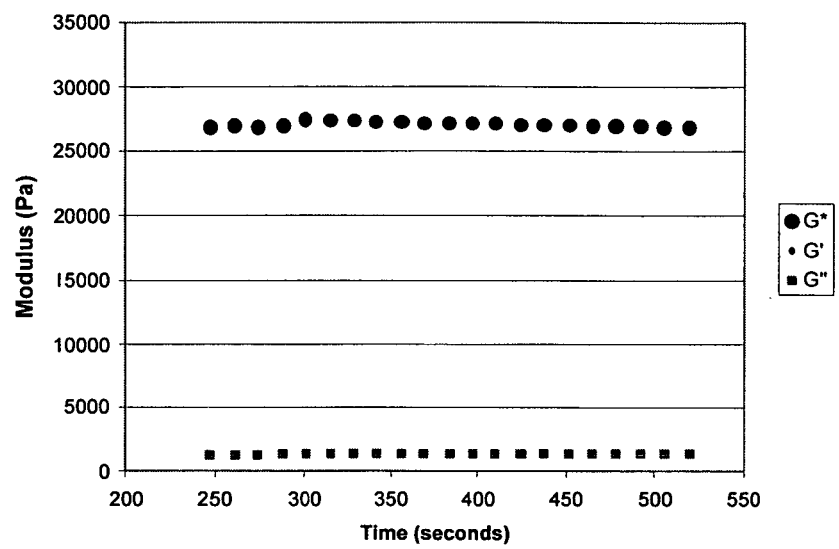
FIG. 7 is a graph of modulus of a maltodextrin-acrylate matrix formed via REDOX polymerization, over a period of time.

The modulus of the formed matrix was determined by rheological measurements. In order to perform rheological measurements, the first and second solutions were combined on the testing plate in the Rheometer (Rheometric Scientific; model #SR-2000) and the mixture was allowed to polymerize to form a matrix. Data recording began before sample was cured in plates. Briefly, 100 µL of solution #1 and 100 µL of solution #2 were mixed on the lower testing plate. As the matrix formed, the upper testing plate was lowered to fully contact the mixture of the first and second solutions as the mixture polymerized into a matrix. The sample was cured within 15 seconds. This curing method ensured maximum contact between the two testing plates resulting in more accurate testing compared to pre-formed matrices being placed between the testing plates. The resulting MD-acrylate matrix had properties of an elastic solid with an elastic (storage) modules ranging from 27 kPa to 30 kPa, and a viscous (loss) modulus of only about 1 kPa. Results are shown in Table 8 and FIG. 7.

TABLE 8

(Testing Conditions: Stress: 433 Pa; strain 1.6%; frequency: 1 radian/sec)

| Time (seconds) | G' (Elastic Modulus; Pa) | G" (Storage Modulus; Pa) | G* (Loss Modulus; Pa) |
|---|---|---|---|
| 247 | 26820.2 | 1300.5 | 26851.7 |
| 261 | 26908.5 | 1294.55 | 26939.6 |
| 274 | 26872 | 1299.28 | 26903.4 |
| 288 | 26943.8 | 1343.69 | 26977.3 |
| 301 | 27376.6 | 1380.43 | 27411.4 |
| 315 | 27327.7 | 1373.31 | 27362.2 |
| 329 | 27319.8 | 1376.27 | 27354.5 |
| 342 | 27274.8 | 1362.35 | 27308.8 |
| 356 | 27246.6 | 1369.38 | 27281 |
| 369 | 27180.6 | 1373.6 | 27215.3 |
| 383 | 27174.4 | 1371.61 | 27209 |
| 397 | 27119.4 | 1366.76 | 27153.9 |
| 410 | 27105.4 | 1360.49 | 27139.5 |
| 424 | 27064.1 | 1358.45 | 27098.2 |
| 437 | 27019.9 | 1355.9 | 27053.9 |
| 451 | 27019.8 | 1355.39 | 27053.8 |
| 465 | 26972.3 | 1355.85 | 27006.4 |
| 478 | 26956.2 | 1361.11 | 26990.5 |
| 492 | 26918.2 | 1352.58 | 26952.2 |
| 505 | 26880.7 | 1355.85 | 26914.9 |
| 519 | 26840.4 | 1360.47 | 26874.9 |

Example 43

Durability Testing of MD-Acrylate Coated PEBAX Rods

To assess lubricity and tenacity of MD-acrylate coated parts, frictional force testing was performed.

Frictional testing over the last 40 cycles of a 50 cycle test was evaluated. Coated rods were evaluated by a horizontal sled style friction test method (modified ASTM D-1894, as described below). Silicone Pads (7 mm diameter) were hydrated and then wrapped around a 200 gram stainless steel sled. The silicone pad was clipped together tightly on the opposite side of the sled. The sled with rotatable arm was then attached to a 500 gram Chatillon Digital Force Gauge (DG-GHS, 500×0.1) with computer interface. The testing surface was mounted on a 22.5 inch positioning rail table with microstepper motor control (Compumotor SX6 Indexer/Drive).

MD-coated rods (from example 18) were hydrated in deionized water and clamped onto the test surface 1 inch (or approximately 2.5 cm) apart. The hydrated Silicone pad (jaw force set at 500 g) moved at 0.5 cm/sec over a 5 cm section for 50 push/pull cycles, and the final force measurements were taken over the last 40 push/pull cycles.

Figure 8:
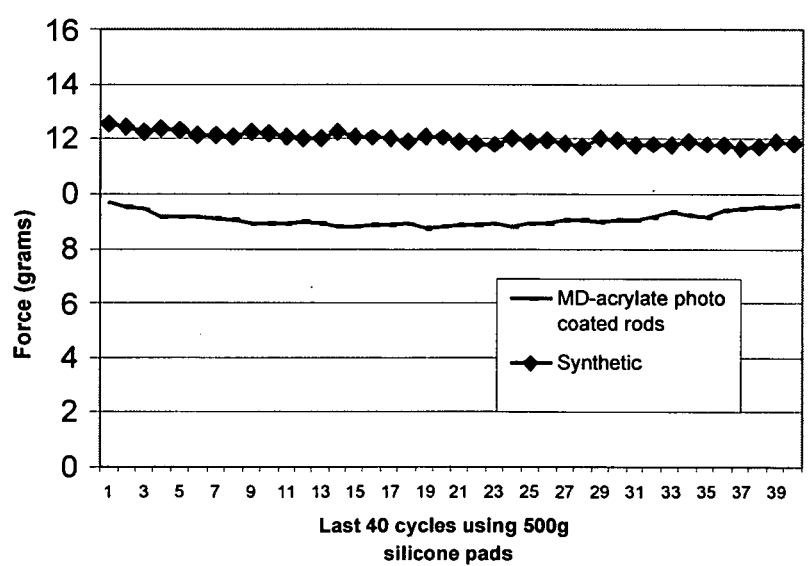
FIG. 8 is a graph of repetitive force testing of maltodextrin-acrylate coated PEBAX rods versus synthetic polymer-coated PEBAX rods.

As shown in Table 9 and FIG. 8, compared to the benchmark synthetic coating (see example 1 of U.S. Pat. No. 6,706, 408B2) the MD-acrylate coated rod provided a coating having excellent lubricity and durability; the rods coated with a MD-acrylate formulation containing a photoinitiator, the grams of force remained relatively constant for the last 40 cycles, indicating a durable coating.

TABLE 9

| | MD-acrylate photo coated rod | Synthetic |
|---|---|---|
| 1 | 9.67 | 12.53 |
| 2 | 9.53 | 12.43 |
| 3 | 9.45 | 12.26 |
| 4 | 9.18 | 12.40 |
| 5 | 9.12 | 12.33 |
| 6 | 9.13 | 12.17 |
| 7 | 9.11 | 12.15 |
| 8 | 9.06 | 12.12 |
| 9 | 8.92 | 12.25 |
| 10 | 8.96 | 12.19 |
| 11 | 8.91 | 12.11 |
| 12 | 8.98 | 12.02 |
| 13 | 8.95 | 12.02 |
| 14 | 8.82 | 12.25 |
| 15 | 8.79 | 12.10 |
| 16 | 8.84 | 12.08 |
| 17 | 8.85 | 12.02 |
| 18 | 8.89 | 11.92 |
| 19 | 8.76 | 12.10 |
| 20 | 8.81 | 12.08 |
| 21 | 8.85 | 11.93 |
| 22 | 8.85 | 11.86 |
| 23 | 8.88 | 11.83 |
| 24 | 8.81 | 12.01 |
| 25 | 8.90 | 11.94 |
| 26 | 8.96 | 11.94 |
| 27 | 9.04 | 11.87 |
| 28 | 9.04 | 11.71 |
| 29 | 8.97 | 12.00 |
| 30 | 9.03 | 11.94 |
| 31 | 9.05 | 11.79 |
| 32 | 9.20 | 11.83 |
| 33 | 9.32 | 11.75 |
| 34 | 9.23 | 11.90 |
| 35 | 9.22 | 11.82 |
| 36 | 9.39 | 11.79 |
| 37 | 9.46 | 11.68 |
| 38 | 9.52 | 11.74 |
| 39 | 9.53 | 11.91 |
| 40 | 9.56 | 11.87 |

Example 44

Preparation of Acylated Maltodextrin (Butyrylated-MD)

Maltodextrin having pendent butyryl groups were prepared by coupling butyric anhydride at varying molar ratios.

To provide butyrylated-MD (1 butyl/4 glucose units, 1:4 B/GU) the following procedure was performed. Maltodextrin (MD; Aldrich; 1.0 g; 3.67 mmole; DE (Dextrose Equivalent): 4.0-7.0) was dissolved in dimethylsulfoxide (DMSO) 600 mL with stirring. The size of the maltodextrin was calculated to be in the range of 2,000 Da-4,000 Da. Once the reaction solution was complete, 1-methylimidazole (Aldrich; 2.0 g, 1.9 mls) and butyric anhydride (Aldrich; 5.0 g, 5.2 mls) was added with stirring. The reaction mixture was stirred for four hours at room temperature. After this time, the reaction mixture was quenched with water and dialyzed against DI water using 1,000 MWCO dialysis tubing. The butyrylated starch was isolated via lyophilization to give 9.315 g (85% yield). NMR confirmed a butyrylation of 1:3 B/GU (1.99 mmoles butyl/g sample).

To provide butyrylated-MD (1:8 B/GU), 2.5 g (2.6 mL) butyric anhydride was substituted for the amount of butyric anhydride described above. A yield of 79% (8.741 g) was obtained. NMR confirmed a butyrylation of 1:5 B/GU (1.31 mmoles butyl/g sample).

To provide butyrylated-MD (1:2B/GU), 10.0 g (10.4 mL) butyric anhydride was substituted for the amount of butyric anhydride described above. A yield of 96% (10.536 g) was obtained. NMR confirmed a butyrylation of 1:2 B/GU (3.42 mmoles butyl/g sample).

Example 45

Preparation of Acrylated Acylated Maltodextrin (Butyrylated-MD-Acrylate)

Preparation of an acylated maltodextrin macromer having pendent butyryl and acrylate groups prepared by coupling butyric anhydride at varying molar ratios.

To provide butyrylated-MD-acrylate (1 butyl/4 glucose units, 1:4 B/GU) the following procedure was performed. MD-Acrylate (Example 13; 1.1 g; 0.367 mmoles) was dissolved in dimethylsulfoxide (DMSO) 60 mL with stirring. Once the reaction solution was complete, 1-methylimidazole (0.20 g, 0.19 mls) and butyric anhydride (0.50 g, 0.52 mls) was added with stirring. The reaction mixture was stirred for four hours at room temperature. After this time, the reaction mixture was quenched with water and dialyzed against DI water using 1,000 MWCO dialysis tubing. The butyrylated starch acrylate was isolated via lyophylization to give 821 mg (75% yield, material lost during isolation). NMR confirmed a butyrylation of 1:3 B/GU (2.38 mmoles butyl/g sample).

Example 46

Preparation of Acrylated Acylated Maltodextrin (Butyrylated-MD-Acrylate)

Maltodextrin having pendent butyryl and acrylate groups prepared by coupling butyric anhydride at varying molar ratios.

To provide butyrylated-MD-acrylate the following procedure is performed. Butyrylated-MD (Example 43; 1.0 g; 0.333 mmole) is dissolved in dimethylsulfoxide (DMSO) 60 mL with stirring. Once the reaction solution is complete, a solution of EA-NCO from Example 12 (353 mg; 2.50 mmole) is evaporated and dissolved in dried DMSO 1.0 mL). The two DMSO solutions are mixed and heated to 55° C. overnight. The DMSO solution is placed in dialysis tubing (1000 MWCO) and dialyzed against water for 3 days. The macromer solution is filtered and lyophilized to give a white solid.

What is claimed is:

1. An implantable medical article having a biodegradable coating comprising polymeric matrix formed from natural biodegradable polysaccharides associated via polymerized groups, wherein the polysaccharides are selected from the group consisting of amylose, polyalditol, cyclodextrin, and maltodextrin, and the polymerized groups are selected from the group consisting of polymerized vinyl, acrylate, methacrylate, ethacrylate, 2-phenyl acrylate, acrylamide, methacrylamide, itaconate, and styrene groups, wherein the polysaccharides further comprise pendent hydrophobic moieties selected from the group consisting of esters of fatty acids and esters of $C_2$-$C_{18}$ alkyl groups.

2. The implantable medical article of claim 1 wherein the natural biodegradable polysaccharides have a molecular weight of 500,000 Da or less.

3. The implantable medical article of claim 1 wherein the natural biodegradable polysaccharides have a molecular weight in the range of 1000 Da to 10,000 Da.

4. The implantable medical article of claim 1 wherein the non-reducing polysaccharide is selected from polyalditol.

5. The implantable medical article of claim 1 wherein the coating further comprises a bioactive agent.

6. The implantable medical article of claim 5 wherein the bioactive agent is selected from the group consisting of polypeptides, nucleic acids, and polysaccharides.

7. The implantable medical article of claim 5 wherein the bioactive agent has a molecular weight of 10,000 Da or greater.

8. The implantable medical article of claim 1 wherein the polymerized group is present on the natural biodegradable polysaccharides in an amount of 0.7 µmoles or less of polymerized group per milligram of natural biodegradable polysaccharide.

9. The implantable medical article of claim 1 wherein the polymerized group is present on the natural biodegradable polysaccharides in an amount in the range of 0.3 to 0.7 µmoles of polymerized group per milligram of natural biodegradable polysaccharide.

10. The implantable medical article of claim 1 being an implantable intraocular medical article.

11. The implantable medical article of claim 1 wherein the coating comprises a coated layer of polymerized natural biodegradable polysaccharides having a thickness in the range of 1 µm to 200 µm.

12. The implantable medical article of claim 1 wherein the pendent hydrophobic moieties comprise butyryl groups.

13. The implantable medical article of claim 12 wherein the butyryl groups are pendent from the polysaccharides, the polysaccharides comprising repeating glucose units, in an amount in the range of 1 butyryl group per 8 glucose units to 1 butyryl group per 2 glucose units.

14. The implantable medical article of claim 13 wherein the butyryl groups are pendent from the polysaccharides in an amount of about 1 butyryl group per 8 glucose units.

15. The implantable medical article of claim 13 wherein the butyryl groups are pendent from the polysaccharides in an amount of about 1 butyryl group per 4 glucose units.

16. The implantable medical article of claim 13 wherein the butyryl groups are pendent from the polysaccharides in an amount of about 1 butyryl group per 2 glucose units.

17. The implantable medical article of claim 1 wherein the polymerized groups are selected from polymerized acrylate or methacrylate.

18. The implantable medical article of claim 1 wherein biodegradable coating is formed comprising using an aqueous composition comprising natural biodegradable polysaccharides comprising pendent polymerizable groups and pendent hydrophobic moieties.

19. An implantable medical article comprising a biodegradable bioactive agent-releasing coating comprising a polymeric matrix of polysaccharides crosslinked via polymerized groups, wherein the polysaccharides are selected from the group consisting of maltodextrin, polyalditol, cyclodextrin, and amylose, and the polymerized groups are selected from the group consisting of polymerized vinyl, acrylate, methacrylate, ethacrylate, 2-phenyl acrylate, acrylamide, methacrylamide, itaconate, and styrene groups, and the polysaccharides further comprise pendent hydrophobic groups selected from the group consisting of esters of fatty acids and esters of C2-C18 alkyl groups, wherein the polymeric matrix further comprises a bioactive agent in the polymeric matrix, and the bioactive agent is capable of being released from the implantable medical article following implantation.

20. A method for delivering a bioactive agent to a subject comprising a step of
implanting in a subject the implantable medical article of claim 19, wherein the bioactive agent is capable of being released from the implantable medical article following implanting.

\* \* \* \* \*